United States Patent
Hayase

(10) Patent No.: US 11,284,805 B2
(45) Date of Patent: Mar. 29, 2022

(54) BLOOD PRESSURE ESTIMATING APPARATUS, METHOD FOR ESTIMATING BLOOD PRESSURE, AND NON-TRANSITORY COMPUTER-READABLE RECORDING MEDIUM HAVING STORED THEREIN PROGRAM FOR ESTIMATING BLOOD PRESSURE

(71) Applicant: TOHOKU UNIVERSITY, Sendai (JP)

(72) Inventor: Toshiyuki Hayase, Sendai (JP)

(73) Assignee: TOHOKU UNIVERSITY, Sendai (JP)

( * ) Notice: Subject to any disclaimer, the term of this patent is extended or adjusted under 35 U.S.C. 154(b) by 349 days.

(21) Appl. No.: 15/981,075

(22) Filed: May 16, 2018

(65) Prior Publication Data

US 2018/0263514 A1    Sep. 20, 2018

Related U.S. Application Data

(63) Continuation of application No. PCT/JP2016/083770, filed on Nov. 15, 2016.

(30) Foreign Application Priority Data

Nov. 17, 2015   (JP) ................................ 2015-224729

(51) Int. Cl.
*A61B 5/021*    (2006.01)
*A61B 5/00*    (2006.01)
(Continued)

(52) U.S. Cl.
CPC ........ *A61B 5/02116* (2013.01); *A61B 5/7278* (2013.01); *A61B 5/0245* (2013.01);
(Continued)

(58) Field of Classification Search
None
See application file for complete search history.

(56) References Cited

U.S. PATENT DOCUMENTS 3,893,452 A * 7/1975 Birnbaum ............ A61B 5/0215
600/486
5,423,322 A * 6/1995 Clark ................. A61B 5/02007
600/480
(Continued)

FOREIGN PATENT DOCUMENTS

EP         2 730 302 A1    5/2014
JP         2003-500148 A   1/2003
(Continued)

OTHER PUBLICATIONS

International Search Report issued for corresponding International Patent Application No. PCT/JP2016/083770, dated Feb. 7, 2017, with an English translation.
(Continued)

*Primary Examiner* — Jacqueline Cheng
*Assistant Examiner* — Jairo H Portillo
(74) *Attorney, Agent, or Firm* — Myers Wolin, LLC

(57) ABSTRACT

A blood pressure estimating apparatus includes: a detecting unit that detects a first parameter representing a period length being a length of a period of a heartbeat of a living body; a processing unit that determines, using the detected first parameter, a change of a volume of at least one vessel among a plurality of vessels that resiliently deform in a mathematical model with respect to time, the mathematical model expressing blood flowing in a circulatory system of the living body with fluid flowing through a flow path formed by annularly coupling the plurality of vessels, and estimates blood pressure of the blood using the determined change and the mathematical model.

10 Claims, 41 Drawing Sheets

(51) Int. Cl.
*A61B 5/024* (2006.01)
*A61B 5/0245* (2006.01)
*A61B 5/0295* (2006.01)

(52) U.S. Cl.
CPC ......... *A61B 5/0295* (2013.01); *A61B 5/02416* (2013.01); *A61B 5/681* (2013.01)

(56) References Cited

U.S. PATENT DOCUMENTS

| | | | | |
|---|---|---|---|---|
| 6,011,989 | A * | 1/2000 | Sugo | A61B 5/0468 600/513 |
| 6,413,223 | B1 | 7/2002 | Yang et al. | |
| 7,413,545 | B2 * | 8/2008 | Muramatsu | A61B 5/02241 600/301 |
| 7,654,964 | B1 * | 2/2010 | Kroll | A61B 5/02028 600/481 |
| 2002/0188205 | A1 * | 12/2002 | Mills | A61B 5/02125 600/481 |
| 2008/0287812 | A1 * | 11/2008 | Parlikar | A61B 5/029 600/485 |
| 2009/0082684 | A1 | 3/2009 | Sornmo et al. | |
| 2011/0098767 | A1 * | 4/2011 | Sugimachi | A61B 5/0215 607/17 |
| 2011/0245691 | A1 * | 10/2011 | Silber | A61B 5/682 600/485 |
| 2013/0324814 | A1 * | 12/2013 | Maarek | A61B 5/14551 600/324 |
| 2015/0080746 | A1 * | 3/2015 | Bleich | A63B 24/0075 600/479 |

FOREIGN PATENT DOCUMENTS

| | | |
|---|---|---|
| JP | 2007-029137 A | 2/2007 |
| JP | 2008-512177 A | 4/2008 |
| JP | 2013-132407 A | 7/2013 |
| WO | 2013/005320 A1 | 1/2013 |

OTHER PUBLICATIONS

Written Opinion of the International Searching Authority issued for corresponding International Patent Application No. PCT/JP2016/083770, dated Feb. 7, 2017, with an English translation.

* cited by examiner

FIG. 8

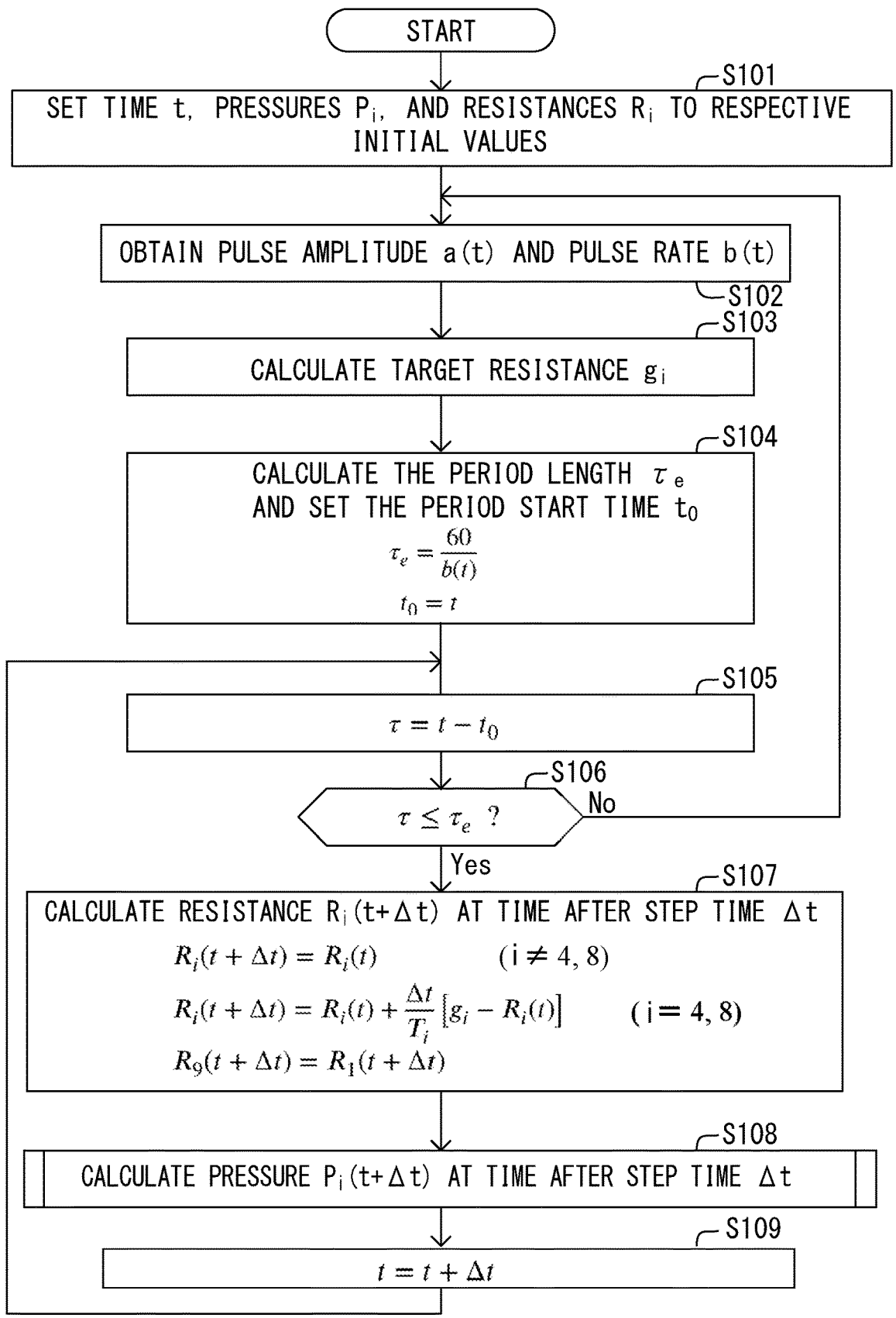

```
START
   ↓
S101: SET TIME t, PRESSURES P_i, AND RESISTANCES R_i TO RESPECTIVE INITIAL VALUES
   ↓
S102: OBTAIN PULSE AMPLITUDE a(t) AND PULSE RATE b(t)
   ↓
S103: CALCULATE TARGET RESISTANCE g_i
   ↓
S104: CALCULATE THE PERIOD LENGTH τ_e AND SET THE PERIOD START TIME t_0
```

$$\tau_e = \frac{60}{b(t)}$$
$$t_0 = t$$

S105: $\tau = t - t_0$

S106: $\tau \leq \tau_e$ ? — No → (back to S102)

Yes ↓

S107: CALCULATE RESISTANCE $R_i(t+\Delta t)$ AT TIME AFTER STEP TIME $\Delta t$ $$R_i(t + \Delta t) = R_i(t) \quad (i \neq 4, 8)$$
$$R_i(t + \Delta t) = R_i(t) + \frac{\Delta t}{T_i}\left[g_i - R_i(t)\right] \quad (i = 4, 8)$$
$$R_9(t + \Delta t) = R_1(t + \Delta t)$$

S108: CALCULATE PRESSURE $P_i(t+\Delta t)$ AT TIME AFTER STEP TIME $\Delta t$

S109: $t = t + \Delta t$

BLOOD PRESSURE ESTIMATING APPARATUS, METHOD FOR ESTIMATING BLOOD PRESSURE, AND NON-TRANSITORY COMPUTER-READABLE RECORDING MEDIUM HAVING STORED THEREIN PROGRAM FOR ESTIMATING BLOOD PRESSURE

CROSS-REFERENCE TO RELATED APPLICATION

This application is a continuation application of International Application PCT/JP2016/083770, filed on Nov. 15, 2016 and designated the U.S., and this application is based upon and claims the benefit of priority of the prior Japanese Patent application No. 2015-224729, filed on Nov. 17, 2015, the entire contents of which are incorporated herein by references.

FIELD

The embodiments discussed herein are related to a blood pressure estimating apparatus, a method for estimating blood pressure, and a non-transitory computer-readable recording medium having stored therein a program for estimating blood pressure.

BACKGROUND

A blood pressure estimating apparatus has been known which estimates pressure of the blood flowing the circulatory system of a living body (i.e., blood pressure) (e.g., see Patent Document 1). A blood pressure estimating apparatus detects the artery diameter at two positions on the surface of a finger and detects the electric impedance of the living body between the two positions. Further, the blood pressure estimator estimates the blood pressure based on the detected artery diameters and electrical impedance, and the Kalman filter.

LIST OF RELATED ART DOCUMENTS

[Patent Document 1] Japanese National Publication of International Patent Application No. 2003-500148

Incidentally, it is difficult to precisely detect an artery diameter and an electrical impedance. For this reason, the above blood pressure estimating apparatus sometimes fails to precisely estimate blood pressure.

SUMMARY

As an aspect of the invention, a blood pressure estimating apparatus including: a detecting unit that detects a first parameter representing a period length being a length of a period of a heartbeat of a living body; a processing unit that determines, using the detected first parameter, a change of a volume of at least one vessel among a plurality of vessels that resiliently deform in a mathematical model with respect to time, the mathematical model expressing blood flowing in a circulatory system of the living body with fluid flowing through a flow path formed by annularly coupling the plurality of vessels, and estimates pressure of the blood using the determined change and the mathematical model.

As an additional aspect of the invention, a method for estimating blood pressure including: determining, using a first parameter that is detected and that represents a period length being a length of a period of a heartbeat of a living body, a change of a volume of at least one vessel among a plurality of vessels that resiliently deform in a mathematical model with respect to time, the mathematical mode expressing blood flowing in a circulatory system of the living body with fluid flowing through a flow path formed by annularly coupling the plurality of vessels; and estimating pressure of the blood using the determined change and the mathematical model.

As a further aspect of the invention, a non-transitory computer-readable recording medium having stored therein a program for estimating blood pressure, the program causing a computer to execute a process including: determining, using a first parameter that is detected and that represents a period length being a length of a period of a heartbeat of a living body, a change of a volume of at least one vessel among a plurality of vessels that resiliently deform in a mathematical model with respect to time, the mathematical model expressing blood flowing in a circulatory system of the living body with fluid flowing through a flow path formed by annularly coupling the plurality of vessels; and estimating pressure of the blood using the determined change and the mathematical model.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 8 is a flow diagram denoting a process performed by a processing unit of FIG. 1.

DESCRIPTION OF EMBODIMENTS

Hereinafter, description will now be made in relation to each embodiment related to a blood pressure estimating apparatus, a method for estimating blood pressure, and a non-transitory computer-readable recording medium having stored therein a program for estimating blood pressure with reference to FIGS. 1-41.

First Embodiment (Configuration)

Figure 1:
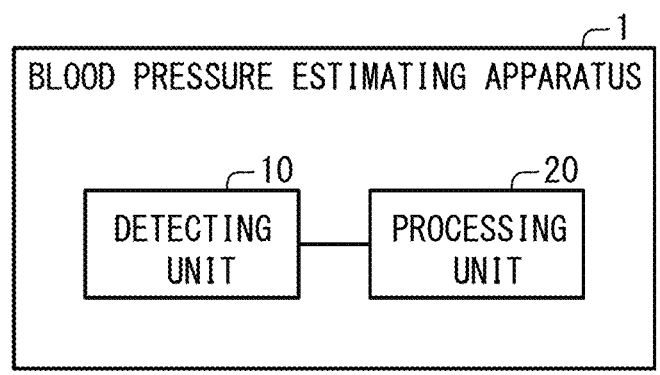
FIG. 1 is a block diagram illustrating the configuration of a blood pressure estimating apparatus according to a first embodiment.

As illustrated in FIG. 1, a blood pressure estimating apparatus 1 of a first embodiment includes a detecting unit 10 and a processing unit 20. In the present embodiment, the blood pressure estimating apparatus 1 is a wristwatch type. Alternatively, the blood pressure estimating apparatus 1 may be of a different type of a wristwatch (e.g., an adhesive plaster type).

The detecting unit 10 detects a first parameter representing a period length corresponding to the length of a period of a heartbeat (i.e., a pulse) of a living body. In the present embodiment, living body is a human living body. Alternatively, the living body may be that of an animal except for human.

In the present embodiment, the first parameter is a pulse rate. A pulse rate is the number of pulse of the living body per predetermined unit time (in the present embodiment, one minute). In the present embodiment, a pulse rate is calculated by dividing the unit time by a period length of a single pulse. Alternatively, the period length may be calculated by dividing the unit time by a pulse rate. Alternatively, a first parameter may be a period length.

Further, the detecting unit 10 detects a second parameter representing a magnitude of a heartbeat of the living body. In the present embodiment, the second parameter is the difference between the minimum value and the maximum value of a signal representing an amount of blood in an artery within a single pulse. Alternatively, the second parameter may be the width of an artery, a cross sectional area of an artery, an amount of blood in artery, a flow amount of blood in artery, a flow rate of blood in artery, and the difference between the minimum value and the maximum value of a signal representing at least one of the above factors within a single pulse. The second parameter may also be referred to as a pulse amplitude.

In the present embodiment, the detecting unit 10 irradiates an artery of the living body with light, detects intensity of the light reflected on the living body, and detects a pulse rate and a pulse amplitude on the basis of a change of the detected intensity with respect to time. For example, the detecting unit 10 detects a pulse rate on the basis of a time between two continuous peaks in the change of the detected intensity. For example, the detecting unit 10 detects a pulse amplitude on the basis of the difference between the minimum value and the maximum value between two continuous peaks in the change of the detected intensity.

Alternatively, the detecting unit 10 may include an element that depresses the surface of the living body near to an artery (e.g., the wrist) and detect a pulse rate and a pulse amplitude through detecting pressure that the element receives from the surface. In this case, the detecting unit 10 may detect the pressure, using a piezoelectric device.

The detecting unit 10 may include electrodes attached to the surface of the living body near to the heart and detect a first parameter and a second parameter through detecting an electric potential of the surface via the electrodes. In this case, the detecting unit 10 may be an adhesive plaster type.

Figure 2:
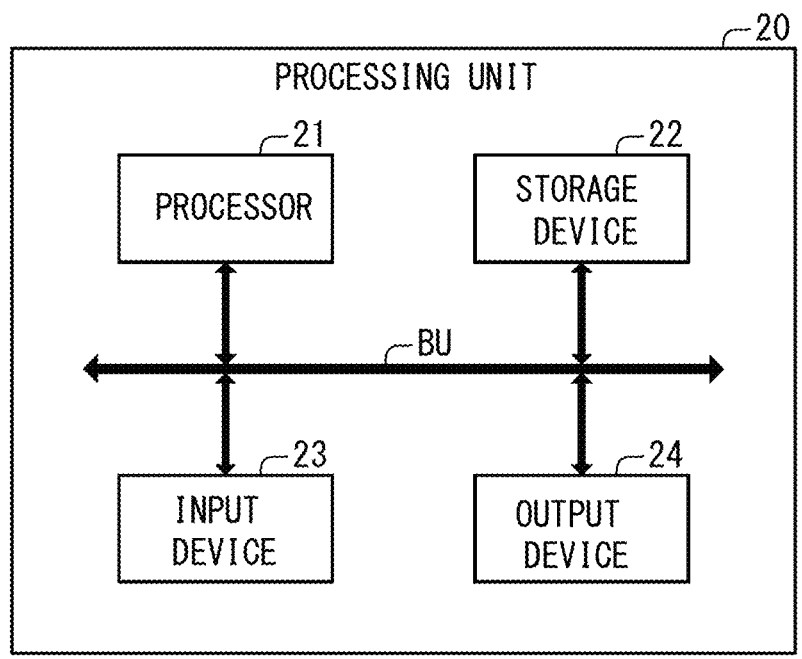
FIG. 2 is a block diagram illustrating the configuration of a processing unit of FIG. 1.

As illustrated in FIG. 2, the processing unit 20 includes a processor 21, a storage device 22, an input device 23, and an output device 24 that are connected to one another via a bus BU. The processing unit 20 is an example of an information processing apparatus.

The processor 21 controls the devices constituting the processing unit 20 by executing a program stored in the storage device 22. Thereby, the processing unit 20 achieves the functions to be described below. In the present embodiment, the processor 21 includes a Central Processing Unit (CPU). Alternatively, the processor 21 may include a Micro Processing Unit (MPU) or a Digital Signal Processor (DSP) in place of or in addition to the CPU. Further alternatively, the processor 21 may be configured by a Large Scale Integration (LSI).

The storage device 22 writably and readably stores information. In the present embodiment, the storage device 22 includes at least one of a Random Access Memory (RAM), a semiconductor memory, and an organic memory. The storage device 22 may include at least one of a Hard Disk Drive (HDD) and a Solid State Drive (SSD). The storage device 22 may include a recording medium such as a flexible disk, an optical disk, a magneto-optical disk, or a semiconductor memory, and a reading device that is able to read information from the recording medium.

The input device 23 inputs information from the outside of the blood pressure estimating apparatus 1. In the present embodiment, the input device 23 includes a key-type button. The input device 23 may include a microphone.

The output device 24 outputs information to the outside of the blood pressure estimating apparatus 1. In the present embodiment, the output device 24 includes a monitor display. The output device 24 may include a speaker.

The processing unit 20 may include a touch-panel display serving as both the input device 23 and the output device 24.

(Function)

The processing unit 20 estimates pressure of the blood flowing in the circulatory system of the living body (i.e., blood pressure) on the basis of the pulse rate and the pulse amplitude detected by the detecting unit 10, and a mathematical model.

Here, description will now be made in relation to a mathematical model. In the present embodiment, a mathematical model expresses blood flowing in the circulatory system of a living body with fluid flowing through a flow path formed by annularly coupling multiple vessels that resiliently deform.

Figure 3:
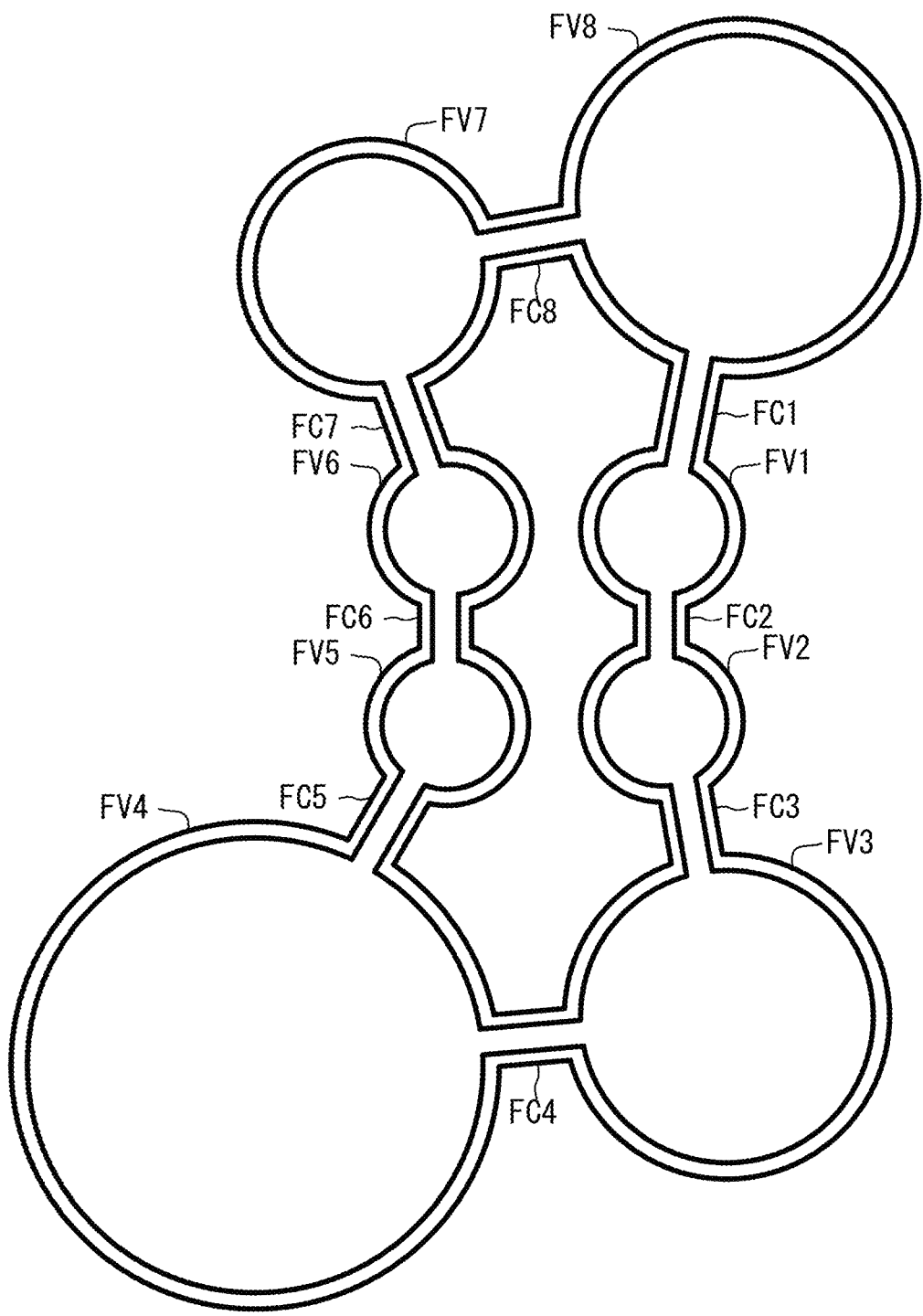
FIG. 3 is an explanatory diagram illustrating a mathematical model used by a processing unit of FIG. 1.
Figure 4:
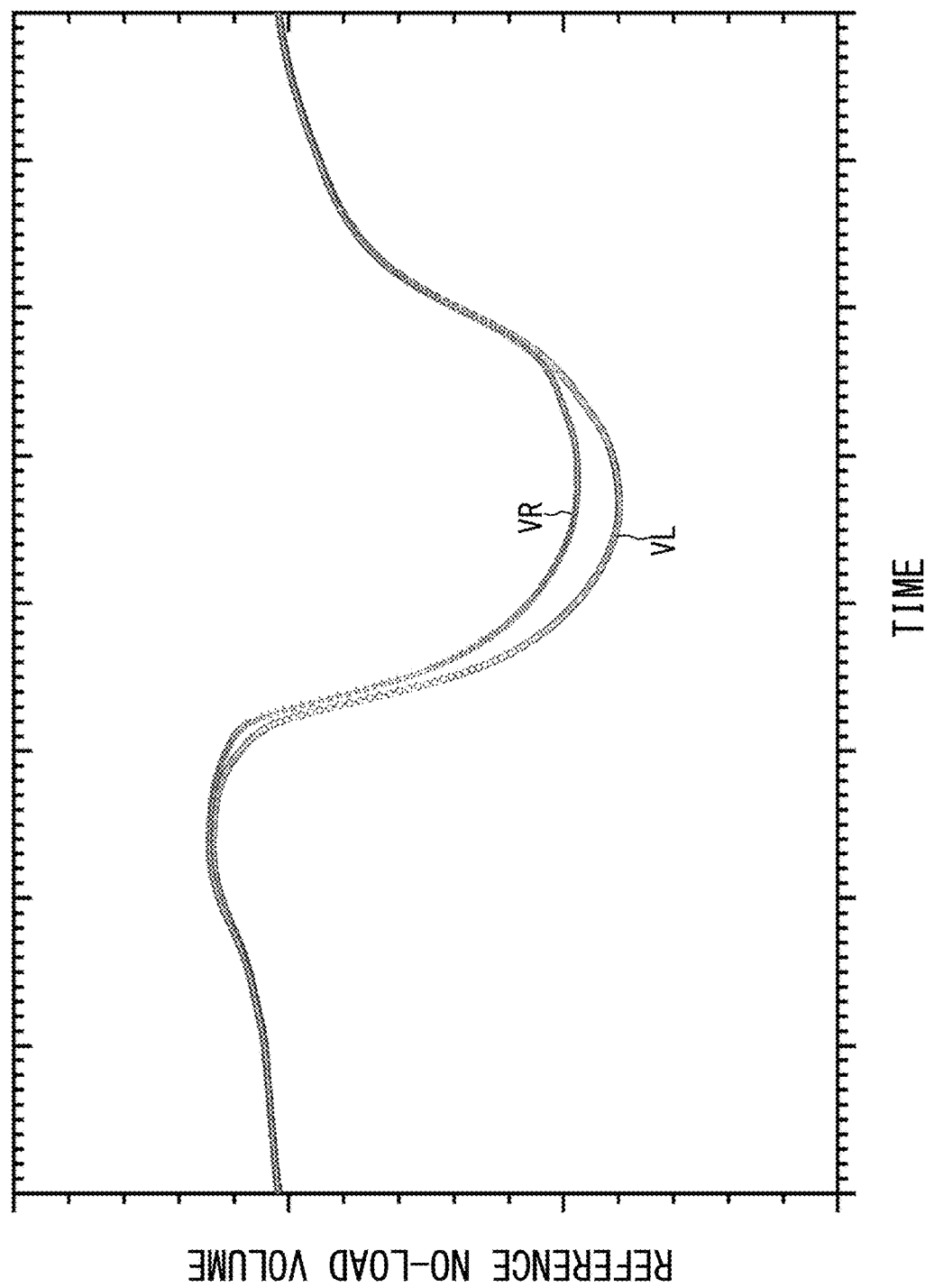
FIG. 4 is a graph illustrating a change of a reference no-load volume stored in a processing unit of FIG. 1 with respect to time.

As illustrated in FIG. 3, the flow path in the mathematical model consists of the first to the eighth vessels FV1-FV8 and the first to the eighth communication pipes FC1 to FC8. Alternatively, the flow path may be formed of nine or more vessels. For example, the flow path may consist of nine or more vessels and communication pipes the same as the number of vessels.

The first to the eighth vessels FV1-FV8 are annularly coupled. In the present embodiment, the first to the seventh vessels FV1-FV7 are coupled to the second to the eighth vessels FV2 to FV8, respectively, via the second to the eighth communication pipes FC2 to FC8, respectively. The eighth vessel FV8 and the first vessel FV1 are coupled to each other via the first communication pipe FC1.

In the flow path, fluid flows from the first to the seventh vessels FV1-FV7 to the second to the eighth vessels FV2 to FV8, respectively, and further flows from the eighth vessel FV8 to the first vessel FV1.

In the present embodiment, the first to the eighth vessels FV1-FV8 represent the left atrium, the left ventricle, the aorta and the artery on the downstream side of the aorta, the vena cava and the vein on the upstream side of the vena cava, the right atrium, the right ventricle, the pulmonary artery, and the pulmonary vein, respectively.

Each of the vessels FV1-FV8 is a spherical shell that resiliently deforms. The differential $dP_i/dt$ of pressure $P_i$ of the fluid in the i-th vessel FVi among the first to the eighth vessels FV1-FV8 8 with respect to time t is given by Expression 1. The symbol i represents integers of one to eight.

$$\frac{dP_i(t)}{dt} = E_i\left\{Q_i(t) - Q_{i+1}(t) - \frac{dV_i(t)}{dt}\right\}, \quad \text{[Expression 1]}$$
where $i = 1, \ldots, 8$ The term $Q_i$ represents a flow amount flowing into the i-th vessel FVi; the term $Q_{i+1}$ represents a flow amount flowing out from the i-th vessel FVi; the term $V_i$ represents a volume of the i-th vessel FVi when the pressure Pi of the fluid in the i-th vessel FVi is zero (i.e., Vi represents a no-load volume). The term $E_i$ represents a predetermined coefficient associated with the i-th vessel FVi. The coefficient $E_i$ may be regarded as a parameter representing a ratio of a change of the pressure Pi of the fluid in the i-th vessel FVi with respect to time to a change of the volume of the i-th vessel FVi with respect to time. The coefficient $E_i$ may be regarded as a parameter representing a ratio of a change of the pressure $P_i$ of the fluid in the i-th vessel FVi with respect to time to an amount obtained by subtracting an amount of the fluid flowing out from the i-th vessel FVi per unit time and a change of the no-load volume Vi of the i-th vessel FVi with respect to time from an amount of the fluid flowing into the i-th vessel FVi per unit time.

Among the first to the eighth vessels FV1-FV8, the no-load volumes $V_1$, $V_3$-$V_5$, $V_7$, and $V_8$ of the vessels FV1, FV3-FV5, FV7, and FV8 except for the second and the sixth vessels FV2 and FV6 do not change with respect to time. On the other hand, the no-loaded volumes $V_2$ and $V_6$ of the second and the sixth vessels FV2 and FV6 change with respect to time as indicated by Expression 2. The changes of the no-loaded volumes $V_2$ and $V_6$ of the second and the sixth vessels FV2 and FV6 with respect to time can be regarded as pulsation of the left ventricle and the right ventricle, respectively.

$$V_i(t)=f_i(a(t),b(t),\tau(t)), \text{ where } i=2,6 \quad \text{[Expression 2]}$$

The term a represents a pulse amplitude detected by the detecting unit 10; the term b represents a pulse rate detected by the detecting unit 10; and the term τ represents a time from a time point of start a period in a period of a single pulse (i.e., τ represents an intra-period time).

The term $f_i$ represents a no-loaded volume $V_i$, which has a predetermined value depending on the pulse amplitude a, the pulse rate b, and the time τ. In the present embodiment, the no-load volume $f_i$ is given by Expression 3. As in the present embodiment, the no-loaded volumes $f_2$ and $f_6$ of the second and the sixth vessels FV2 and FV6 are determined on the basis of the pulse amplitude a and the pulse rate b.

$$f_i(a(t), b(t), \tau(t)) = \frac{a(t)}{a_0} f_{i,0}\left(\frac{b(t)}{b_0}\tau(t)\right), \quad \text{[Expression 3]}$$
$$\text{where } i = 2, 6$$

The term $f_{i,0}$ represents a reference value of a no-load volume $f_i$ when the pulse amplitude a is a reference value $a_0$ (i.e., a reference no-load volume). The reference no-load volume $f_{i,0}$ has a value predetermined on the basis of a time τ from a time point when the period of a single pulse starts and a ratio of the pulse rate b to the reference value $b_0$ (i.e., pulse rate ratio $b/b_0$). In the present embodiment, the reference no-load volumes $f_{2,0}$ and $f_{6,0}$ of the second and the sixth vessels FV2 FV6 are expressed by curves VL and VR of FIG. 4, respectively.

As indicated by Expression 4, a flow amount $Q_9$ flowing out from the eighth vessel FV8 equals a flow amount $Q_1$ flowing into the first vessel FV1. Here, the flow amounts $Q_i$ into the first to the eighth vessels FV1-FV8 can be regarded as the flow amounts of the first to the eighth communication pipes FC1 to FC8, respectively.

$$Q_9(t)=Q_1(t) \quad \text{[Expression 4]}$$

The flow amount $Q_i$ each of the first to the eighth communication pipes FC1 to FC8 is given by Expression 5.

$$Q_i(t) = C(P_{i-1}(t), P_i(t))\left\{\frac{P_{i-1}(t) - P_i(t)}{R_i(t)}\right\}, \quad \text{[Expression 5]}$$
$$\text{where } i = 1, \ldots, 8$$

As indicated by Expression 6, the function C expresses zero when the pressure $P_{i-1}$ of the upstream vessel connected to the i-th communication pipe FCi is smaller than the pressure $P_i$ of the downstream vessel connected to the i-th connection pipe FCi. Furthermore, as indicated by Expression 6, the function C expresses one when the pressure $P_{i-1}$ of the upstream vessel connected to the i-th communication pipe FCi is equal to or higher than the pressure $P_i$ of the downstream vessel connected to the i-th connection pipe FCi. The function C can regarded as a valve that prevents backflow of the fluid (i.e., a check valve).

$$C(x, y) = \begin{cases} 0, & \text{if } x < y \\ 1, & \text{if } x \geq y \end{cases} \quad \text{[Expression 6]}$$

As indicated by Expression 7, the pressure $P_0$ of the upstream vessel connected to the first communication pipe FC1 equals to the pressure $P_8$ of the downstream vessel connected to the eighth communication pipe FC8.

$$P_0(t)=P_8(t) \quad \text{[Expression 7]}$$

The term $R_i$ represents a resistance against a flow of a fluid from the upstream vessel connected to the i-th communication pipe FCi to the downstream vessel connected to the i-th communication pipe FCi. A resistance Ri can be regarded as a ratio of a difference of pressure of the fluid in a vessel between two vessels connected to one another among the multiple vessels FV1-FV8 to the flow amount of the fluid between the two vessels.

Among the first to the eighth communication pipes FC1 to FC8, the resistances $R_1$-$R_3$ and $R_5$-$R_7$ against the communication pipes FC1-FC3 and FC5-FC7 except for the fourth and the eighth communication pipes FC4 and FC8 do not change with respect to time. In contrast, as indicated by Expression 8, the resistances $R_4$ and $R_8$ against the fourth and the eighth communication pipes FC4 and FC8 change with respect to time. The resistances $R_4$ and $R_8$ against the fourth and eighth communication pipes FC4 and FC8 can be regarded as peripheral vascular resistances.

$$\frac{dR_i(t)}{dt} = \frac{1}{T_i}[g_i(a(t), b(t)) - R_i(t)], \quad \text{[Expression 8]}$$
$$\text{where } i = 4, 8$$

The term $g_i$ represent a target value of a resistance $R_i$ (i.e., the target resistance). As indicated by Expression 8, a resistance $R_i$ may be considered to approach the target resistance $g_i$ with a delay. A target resistance $g_i$ has a value predetermined in accordance with a pulse amplitude a and a pulse rate b. In the present embodiment, a target resistance $g_i$ is given by Expression 9.

$$g_i(a(t), b(t)) = \gamma_i\left(\frac{a(t)}{a_0}\right)g_{i,0}\left(\frac{b(t)}{b_0}\right), \quad \text{[Expression 9]}$$
$$\text{where } i = 4, 8$$

Figure 5:
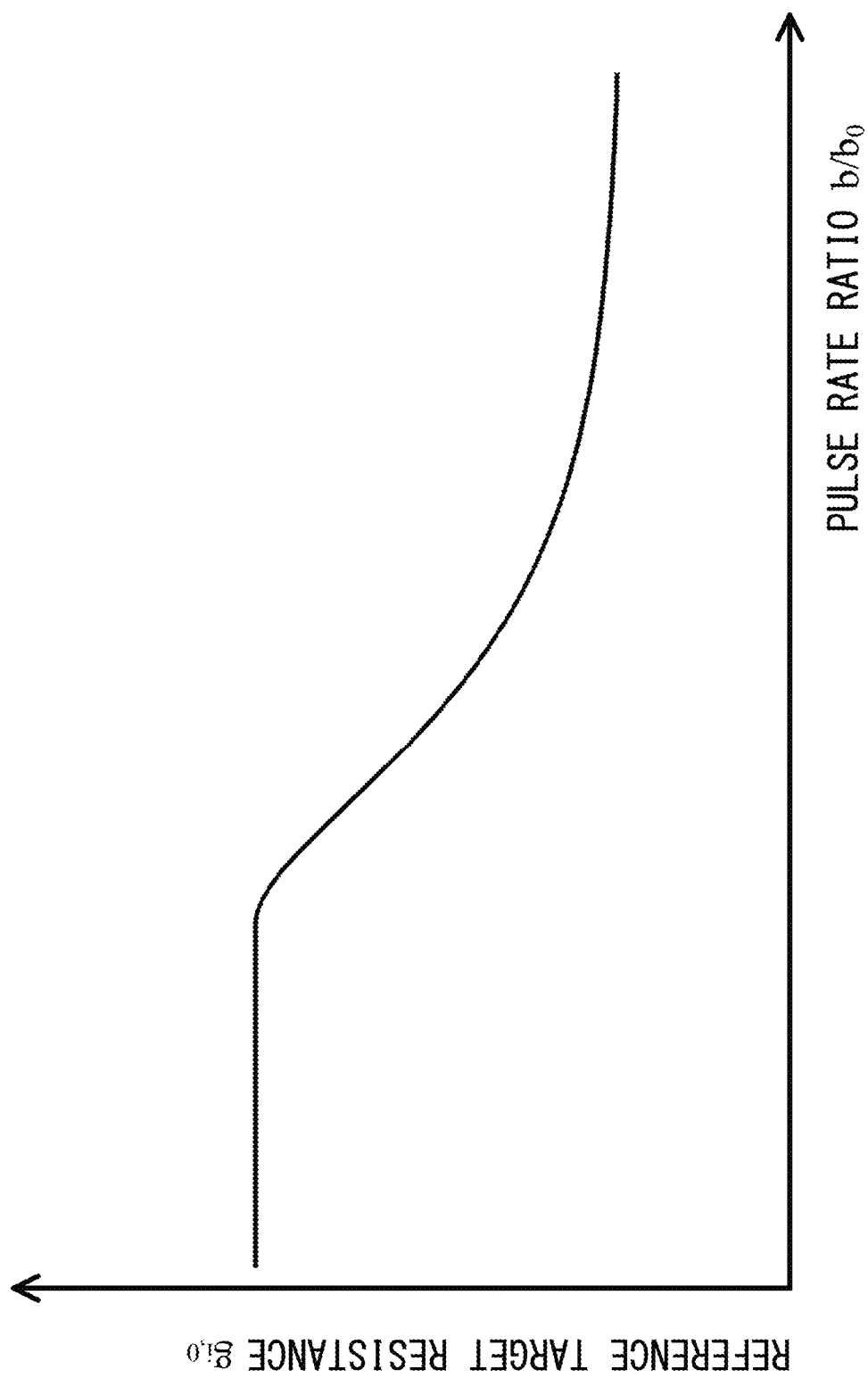
FIG. 5 is a graph illustrating a change of a reference target resistance stored in a processing unit of FIG. 1 with respect to a pulse rate ratio.

The term $g_{i,0}$ represents a reference value of a target resistance $g_i$ (i.e., a reference target resistance) in cases where the pulse amplitude a is the reference value $a_0$. The reference target resistance $g_{i,0}$ has a value predetermined in accordance with the pulse rate ratio $b/b_0$. In the present embodiment, as indicated by FIG. 5, the reference target resistance $g_{i,0}$ decreases as the pulse rate ratio $b/b_0$ increases.

Figure 6:
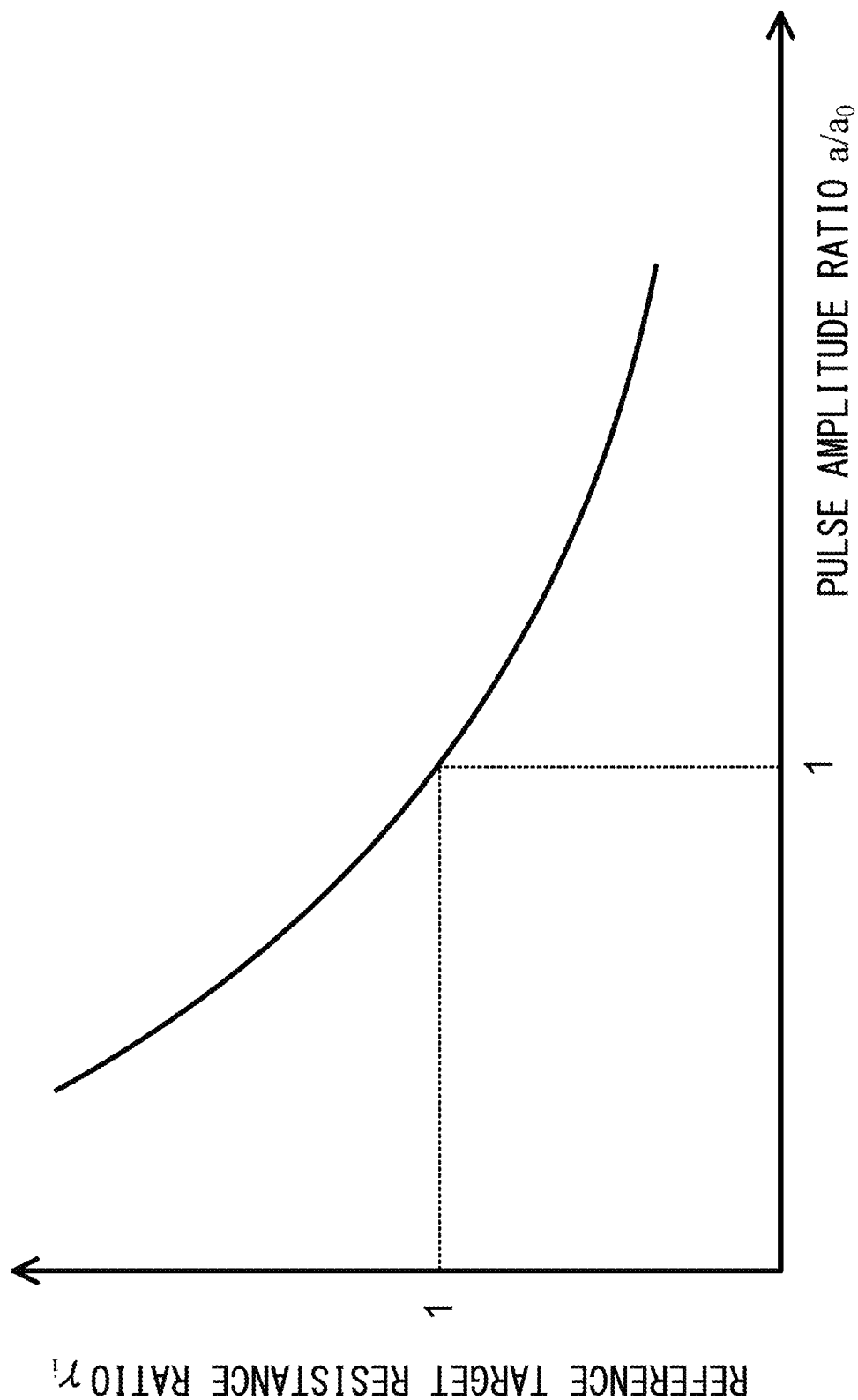
FIG. 6 is a graph illustrating a change of a reference target resistance ratio stored in a processing unit of FIG. 1 with respect to a pulse rate ratio.

The term $\gamma_i$ represents a ratio (i.e., reference target resistance ratio) of a target resistance $g_i$ to the reference target resistance $g_{i,0}$. The reference target resistance ratio $\gamma_i$ has a value predetermined in accordance with a ratio (i.e., a pulse amplitude ratio) $a/a_0$ of the pulse amplitude a to the reference value $a_0$. In the present embodiment, as indicated by FIG. 6, the reference target resistance ratio $\gamma_i$ decreases as the pulse amplitude ratio $a/a_0$ increases and becomes one in cases where the pulse amplitude ratio $a/a_0$ is one.

The term $T_i$ represents a time constant of a change of a resistance $R_i$. The time constant $T_i$ may be considered to express an extent of a delay of a change of a resistance $R_i$ from a change of a target resistance $g_i$.

As described above, the resistances $R_4$ and $R_8$ against the fourth and the eighth communication pipes FC4 and FC8 are determined on the basis of a pulse amplitude a and a pulse rate b.

Figure 7:
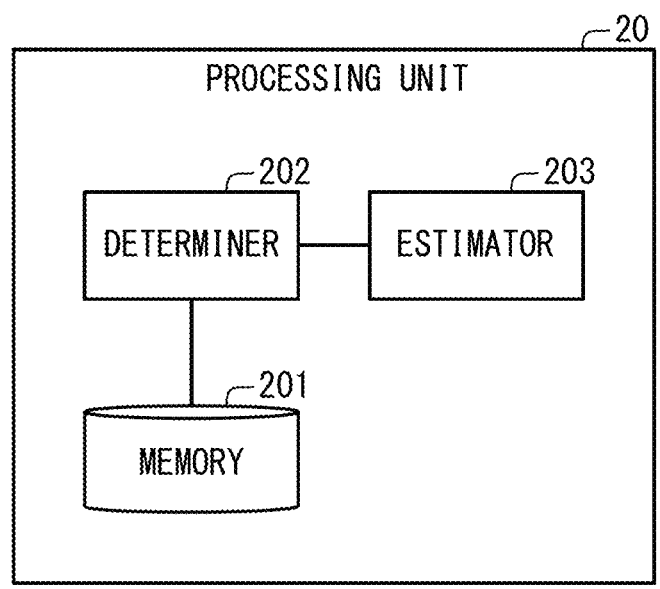
FIG. 7 is a block diagram illustrating the function of a processing unit of FIG. 1.

As illustrated in FIG. 7, the function of the processing unit 20 includes a memory 201, a determiner 202, and an estimator 203.

The processing unit 20 repeats a process of estimating pressures $P_1(t+\Delta t)$ to $P_8(t+\Delta t)$ of the fluid in the first to the eighth vessels FV1-FV8 after time $t+\Delta t$ when a predetermined step time $\Delta t$ has passed since the time t, using the pressures $P_1(t)$ to $P_8(t)$ of the fluid of the first to the eighth vessels FV1-FV8 at the time (i.e., a time point) t on the basis of the above Expressions 1-9.

The memory 201 stores a reference no-load volume $f_{i,0}$ and a reference target resistance $g_{i,0}$ in advance. Alternatively, the processing unit 20 may store a function to calculate a reference no-load volume $f_{i,0}$ in place of storing a reference no-load volume $f_{i,0}$. Likewise, the processing unit 20 may store a function to calculate a reference target resistance $g_{i,0}$ in place of storing a reference target resistance $g_{i,0}$.

In the present embodiment, the memory 201 stores a reference target resistance ratio $\gamma_i$ in advance. Alternatively, the processing unit 20 may store a function to calculate a reference target resistance ratio $\gamma_i$ in place of storing a reference target resistance ratio $\gamma_i$.

The estimator 203 sets the time t, the pressures $P_1$ to $P_8$, and the resistances $R_1$ to $R_8$ to the respective initial values $t_{ini}$, $P_{1,ini}$ to $P_{8,ini}$, and $R_{1,ini}$ to $R_{8,ini}$.

The estimator 203 obtains the pulse rate b(t) and the pulse amplitude a(t) at a time t on the basis of the pulse rate and the pulse amplitude detected by detecting unit 10. In the present embodiment, the estimator 203 obtains the pulse rate b(t) and the pulse amplitude a(t) at time t through interpolation (e.g., linear interpolation) on the basis of the time when the detecting unit 10 detects the pulse rate and the pulse amplitude, the time t, and the pulse rate and the pulse amplitude detected by the detecting unit 10.

Alternatively, the estimator 203 may obtain, not through interpolation, the pulse rate and the pulse amplitude detected by the detecting unit 10 at time closest to the time t to be the pulse rate b(t) and the pulse amplitude a(t) at time t.

The determiner 202 calculates a target resistance $g_i$ on the basis of a reference target resistance $g_{i,0}$ stored in the memory 201, Expression 9, and the pulse rate b(t) and the pulse amplitude a(t) obtained by the estimator 203. In the present embodiment, the determiner 202 calculates a target resistance $g_i$ on the basis of a reference target resistance $g_{i,0}$ stored in the memory 201, a reference target resistance ratio $\gamma_i$ stored in the memory 201, Expression 9, and the pulse rate b(t) and the pulse amplitude a(t) obtained by the estimator 203. Calculating of a target resistance $g_i$ is an example of determining of a target resistance $g_i$.

The estimator 203 calculates a period length $\tau_e$ at the time t on the basis of the obtained pulse rate b(t) and Expression 10.

$$\tau_e = \frac{60}{b(t)} \quad \text{[Expression 10]}$$

The estimator 203 sets the period starting time $t_0$ to the time t. The period starting time $t_0$ is the time when the period of each pulse starts.

The estimator 203 calculates intra-period time $\tau$ by subtracting the period starting time $t_0$ from the time t.

The estimator 203 calculates the resistances $R_4(t+\Delta t)$ and $R_8(t+\Delta t)$ against the forth and the eighth communication pipes FC4 and FC8 at the time $t+\Delta t$ when the step time $\Delta t$ has passed since the time t on the basis of Expression 11, which is the difference equation of Expression 8, and a target resistance $g_i$ calculated by the determiner 202. Calculating of a resistance $R_i$ is an example of determining of a resistance $R_i$.

$$R_i(t+\Delta t) = R_i(t) + \frac{\Delta t}{T_i}[g_i(a(t), b(t)) - R_i(t)], \quad \text{[Expression 11]}$$

where $i = 4, 8$

The determiner 202 calculates time derivatives $\phi_2(\tau)$ and $\phi_6(\tau)$ of the no-load volumes $V_2$ and $V_6$ of the second and the sixth vessels FV2 and FV6 at the time t on the basis of the reference no-load volume $f_{i,0}$ stored in the memory 201, Expression 3, Expression 12, the pulse rate b(t) and the pulse amplitude a (t) obtained by the estimator 203, and the intra-period time $\tau(t)$ calculated by the estimator 203. A time derivative $\Phi_i$ of a no-load volume $V_i$ is an example of a change of the no-load volume $V_i$ with respect to time. Calculating of a time derivative $\Phi_i$ is an example of determining of the time derivative $\Phi_i$.

$$\Phi_i(\tau) = \frac{d}{dt}f_i(a(t), b(t), \tau(t)), \quad \text{[Expression 12]}$$

where $i = 2, 6$

The memory 201 may store a time derivative of a reference no-load volume $f_{i,0}$ in place of or in addition to the reference no-load volume $f_{i,0}$. In this case, the determiner 202 may calculate time derivatives $\phi_2(\tau)$ and $\phi_6(\tau)$ of the non-load volumes $V_2$ and $V_6$ of the second and the sixth vessels FV2 and FV6 at the time t, on the basis of the time derivative of the reference no-load volume $f_{i,0}$ stored in the memory 201, the pulse rate b(t) and the pulse amplitude a(t) obtained bun the estimator 203, and the intra-period time $\tau(t)$ calculated by the estimator 203. In this case, the processing unit 20 may store a function to calculate a time derivative of a reference no-load volume $f_{i,0}$ in place of storing a time derivative of a reference no-load volume $f_{i,0}$.

As described above, in the present embodiment, among the first to the eighth vessels FV1-FV8, the no-load volumes $V_1$, $V_3$-$V_5$, $V_7$, and $V_8$ of the vessels FV1, FV3-FV5, FV7, and FV8 except for the second and the sixth vessels FV2 and FV6 do not change with respect to time. Accordingly, the time derivatives $\Phi_1(\tau)$, $\Phi_3(\tau)$ to $\Phi_5(\tau)$, $\Phi_7(\tau)$, and $\Phi_8(\tau)$ of the no-load volumes $V_1$, $V_3$ to $V_5$, $V_7$, and $V_8$ except for the second and the sixth vessels FV2 and FV6 among the first to the eighth vessels FV1-FV8 are zero.

The estimator 203 calculates the pressures $P_1(t+\Delta t)$ to $P_8(t+\Delta t)$ of the fluid in the first to the eighth vessels FV1-FV8 at the time $t+\Delta t$ when the step time $\Delta t$ has passed since the time t on the basis of Expressions 13-21 obtained through applying the Runge-Kutta fourth-order method to the differential equation indicated by Expression 1. Calculating the pressures $P_1(t+\Delta t)$ to $P_8(t+\Delta t)$ is an example of estimating of the pressures $P_1(t+\Delta t)$ to $P_8(t+\Delta t)$.

$$P_i(t+\Delta t) = P_i(t) + \frac{\Delta t}{6}(K_{i,1} + 2K_{i,2} + 2K_{i,3} + K_{i,4}),$$
where $i = 1, \ldots, 8$ [Expression 13]

$$P_{i,0} = P_i(t), \text{ where } i = 1, \ldots, 8$$ [Expression 14]

$$K_{i,1} = E_i\left[C(P_{i-1,0}, P_{i,0})\left\{\frac{P_{i-1,0} - P_{i,0}}{R_i(t+\Delta t)}\right\} - C(P_{i,0}, P_{i+10})\left\{\frac{P_{i,0} - P_{i+1,0}}{R_{i+1}(t+\Delta t)}\right\} - \Phi_i(\tau)\right],$$
where $i = 1, \ldots, 8$ [Expression 15]

$$P_{i,1} = P_i(t) + \frac{\Delta t}{2}K_{i,1}, \text{ where } i = 1, \ldots, 8$$ [Expression 16]

$$K_{i,2} = E_i\left[C(P_{i-1,1}, P_{i,1})\left\{\frac{P_{i-1,1} - P_{i,1}}{R_i(t+\Delta t)}\right\} - C(P_{i,1}, P_{i+1,1})\left\{\frac{P_{i,1} - P_{i+1,1}}{R_{i+1}(t+\Delta t)}\right\} - \Phi_i\left(\tau + \frac{\Delta t}{2}\right)\right],$$
where $i = 1, \ldots, 8$ [Expression 17]

$$P_{i,2} = P_i(t) + \frac{\Delta t}{2}K_{i,2}, \text{ where } i = 1, \ldots, 8$$ [Expression 18]

$$K_{i,3} = E_i\left[C(P_{i-1,2}, P_{i,2})\left\{\frac{P_{i-1,2} - P_{i,2}}{R_i(t+\Delta t)}\right\} - C(P_{i,2}, P_{i+1,2})\left\{\frac{P_{i,2} - P_{i+1,2}}{R_{i+1}(t+\Delta t)}\right\} - \Phi_i\left(\tau + \frac{\Delta t}{2}\right)\right],$$
where $i = 1, \ldots, 8$ [Expression 19]

$$P_{i,3} = P_i(t) + \Delta t K_{i,3}, \text{ where } i = 1, \ldots, 8$$ [Expression 20]

$$K_{i,4} = E_i\left[C(P_{i-1,3}, P_{i,3})\left\{\frac{P_{i-1,3} - P_{i,3}}{R_i(t+\Delta t)}\right\} - C(P_{i,3}, P_{i+1,3})\left\{\frac{P_{i,3} - P_{i+1,3}}{R_{i+1}(t+\Delta t)}\right\} - \Phi_i(\tau + \Delta t)\right],$$
where $i = 1, \ldots, 8$ [Expression 21]

After estimating the pressures $P_1(t+\Delta t)$ to $P_8(t+\Delta t)$, the estimator 203 updates the time t to the time $t+\Delta t$ when the step time $\Delta t$ has passed since the time t.

The estimator 203 repeats an intra-period process including calculating an intra-period time $\tau$, the resistances $R_4(t+\Delta t)$ and $R_8(t+\Delta t)$, the time derivatives $\Phi_2(\tau)$ and $\Phi_6(\tau)$ of the no-load volumes $V_2$ and $V_6$, and the pressures $P_1(t+\Delta t)$ to $P_8(t+\Delta t)$ and updating the time t as long as the intra-period time $\tau$ is equal to or less than the period length $\tau_e$.

In cases where the intra-period time $\tau$ comes to be longer than the period length $\tau_e$, the estimator 203 again obtains the pulse rate b(t) and the pulse amplitude a(t), calculates a target resistance $g_i$ and the period length $\tau_e$, and sets the period starting time $t_0$, and then carries out the intra-period process again.

In the present embodiment, the processing unit 20 stores the time t and the pressures $P_1(t)$ to $P_8(t)$ at the time t in association with each other each time the time t is updated. Furthermore, in the present embodiment, the processing unit 20 outputs (e.g., displaying on the monitor display) the latest calculated blood pressure via the output device 24 each time a predetermined displaying period (e.g., five minutes) passes. In the present embodiment, the processing unit 20 outputs the pressure $P_3$ of the fluid in the third vessel FV3 as the blood pressure.

Here, the estimator 203 may use constant values (e.g., time derivatives $\Phi_i(\tau)$ in the intra-period time $\tau$) as the time derivatives of the no-load volumes $V_2$ and $V_6$ of the second and the sixth vessels FV2 and FV6 with respect to a time period between the intra-period time $\tau$ and the time $t+\Delta t$ when the step time $\Delta t$ has passed since the intra-period time $\tau$.

Alternatively, the estimator 203 may use Expressions 22-25 in place of Expressions 15, 17, 19, and 21, respectively. In this case, the estimator 203 may calculate, on the basis of Expression 26, the resistances $R_4(t+\Delta t/2)$ and $R_8(t+\Delta t/2)$ against the fourth and the eighth communication pipes FC4 and FC8 at the time $t+\Delta t/2$ when the half $\Delta t/2$ of the step time $\Delta t$ has passed since the time t.

$$K_{i,1} = E_i\left[C(P_{i-1,0}, P_{i,0})\left\{\frac{P_{i-1,0} - P_{i,0}}{R_i(t)}\right\} - C(P_{i,0}, P_{i+10})\left\{\frac{P_{i,0} - P_{i+1,0}}{R_{i+1}(t)}\right\} - \Phi_i(\tau)\right],$$
where $i = 1, \ldots, 8$ [Expression 22]

$$K_{i,2} = E_i\left[C(P_{i-1,1}, P_{i,1})\left\{\frac{P_{i-1,1} - P_{i,1}}{R_i\left(t+\frac{\Delta t}{2}\right)}\right\} - C(P_{i,1}, P_{i+1,1})\left\{\frac{P_{i,1} - P_{i+1,1}}{R_{i+1}\left(t+\frac{\Delta t}{2}\right)}\right\} - \Phi_i\left(\tau + \frac{\Delta t}{2}\right)\right],$$
where $i = 1, \ldots, 8$ [Expression 23]

$$K_{i,3} = E_i\left[C(P_{i-1,2}, P_{i,2})\left\{\frac{P_{i-1,2} - P_{i,2}}{R_i\left(t+\frac{\Delta t}{2}\right)}\right\} - C(P_{i,2}, P_{i+1,2})\left\{\frac{P_{i,2} - P_{i+1,2}}{R_{i+1}\left(t+\frac{\Delta t}{2}\right)}\right\} - \Phi_i\left(\tau + \frac{\Delta t}{2}\right)\right],$$
where $i = 1, \ldots, 8$ [Expression 24]

$$K_{i,4} = E_i\left[C(P_{i-1,3}, P_{i,3})\left\{\frac{P_{i-1,3} - P_{i,3}}{R_i(t+\Delta t)}\right\} - C(P_{i,3}, P_{i+1,3})\left\{\frac{P_{i,3} - P_{i+1,3}}{R_{i+1}(t+\Delta t)}\right\} - \Phi_i(\tau + \Delta t)\right],$$
where $i = 1, \ldots, 8$ [Expression 25]

$$R_i\left(t+\frac{\Delta t}{2}\right) = R_i(t) + \frac{\Delta t}{2T_i}[g_i(a(t), b(t)) - R_i(t)],$$
where $i = 4, 8$ [Expression 26]

(Operation)

Next, description will now be made in relation to operation of the blood pressure estimating apparatus 1.

The detecting unit 10 detects the pulse rate and the pulse amplitude each time when a predetermined detecting period (e.g., one second) passes.

Specifically, the processing unit 20 carries out the process of FIG. 8. Hereinafter, description will now be made in relation to the process of FIG. 8.

The processing unit 20 sets the time t, the pressures $P_1$ to $P_8$, and the resistances $R_1$ to $R_8$ to the respective initial values $t_{ini}$, $P_{1,\ ini}$ to $P_{8,\ ini}$, and $R_{1,\ ini}$ to $R_{8,\ ini}$ (Step S101 of FIG. 8).

Next, the processing unit 20 obtains the pulse rate b(t) and the pulse amplitude a(t) at the time t on the basis of the pulse rate and the pulse amplitude detected by the detecting unit 10 (Step S102 of FIG. 8).

The processing unit 20 calculates the target resistance $g_i$ on the basis of the reference target resistance $g_{i,\ 0}$ stored in the memory 201 and the pulse rate b(t) and the pulse amplitude a(t) obtained in Step S102 (Step S103 of FIG. 8). In the present embodiment, the processing unit 20 calculates the target resistance $g_i$ on the basis of the reference target resistance $g_{i,\ 0}$ stored in the memory 201, the reference target resistance ratio $\gamma_i$ stored in the memory 201, and the pulse rate b(t) and the pulse amplitude a(t) obtained in Step S102.

Next, the processing unit 20 calculates the period length $\tau_e$ at the time t on the basis of the pulse rate b(t) obtained in Step S102, and also sets the period start time $t_0$ to the time t (Step S104 of FIG. 8).

Then the processing unit 20 calculates the value obtained by subtracting the period start time $t_0$ set in Step S104 from the time t to be the intra-period time $\tau$ (Step S105 of FIG. 8). Next, the processor 20 determines whether the intra-period time $\tau$ calculated in Step S105 is equal to or less than the period length $\tau_e$ calculated in Step S104 (Step S106 of FIG. 8).

First, description will now be made in relation to a case where the intra-period time $\tau$ is equal to or less than the period length $\tau_e$. In this case, the processing unit 20 makes a "Yes" determination and proceeds to Step S107 of FIG. 8. Then, the processing unit 20 sets the resistances $R_1(t+\Delta t)$ to $R_3(t+\Delta t)$, and $R_5(t+\Delta t)$ to $R_7(t+\Delta t)$ against the communicating pipes FC1 to FC3 and FC5 to FC7 except for the fourth and the eighth communication pipes FC4 and FC8 among the first to the eighth communication pipes FC1 to FC8 at the time $t+\Delta t$ when the step time $\Delta t$ has passed since the time t to the resistances $R_1(t)$ to $R_3(t)$, and $R_5(t)$ to $R_7(t)$ at the time t, respectively.

Furthermore, the processing unit 20 calculates the resistances $R_4(t+\Delta t)$ and $R_8(t+\Delta t)$ against the fourth and the eighth communication pipes FC4 and FC8 at the time $t+\Delta t$ when the step time $\Delta t$ has passed since the time t on the basis of the target resistance $g_i$ calculated in Step S103. In addition, the processing unit 20 sets, for convenience, the resistance $R_9(t+\Delta t)$ to be used to the resistance $R_1(t+\Delta t)$ against the first communication pipe FC1 in Step S108.

Next, the processing unit 20 calculates the pressures $P_1(t+\Delta t)$ to $P_8(t+\Delta t)$ of the fluid of the first to the eighth vessels FV1-FV8 at the time $t+\Delta t$ when the step time $\Delta t$ has passed since the time t (Step S108 of FIG. 8). The process of Step S108 will be detailed below.

After that, the processing unit 20 updates the time t to the time $t+\Delta t$ when the step time $\Delta t$ has passed since the time t (Step S109 of FIG. 8). Then the processing unit 20 returns to Step S105 and repeats the process of from Step S105 to Step S109 until the intra-period time $\tau$ comes to be larger than the period length $\tau_e$.

When the intra-period time $\tau$ comes to be larger than the period length $\tau_e$, the processing unit 20 makes a "No" determination in Step S106 and returns to Step S102 of FIG. 8. After that, the processing unit 20 again carries out a process of and subsequent to Step S102 on the time t updated in Step S109. In the present embodiment, when the procedure proceeds to Step S102 of FIG. 8, the processing unit 20 waits until the latest time among the times at which a pulse rate and a pulse amplitude are detected by the detecting unit 10 comes to be later than (future of) the time t updated to in Step S109.

Further description will be made in relation to the process of Step S108 of FIG. 8.

Figure 9:
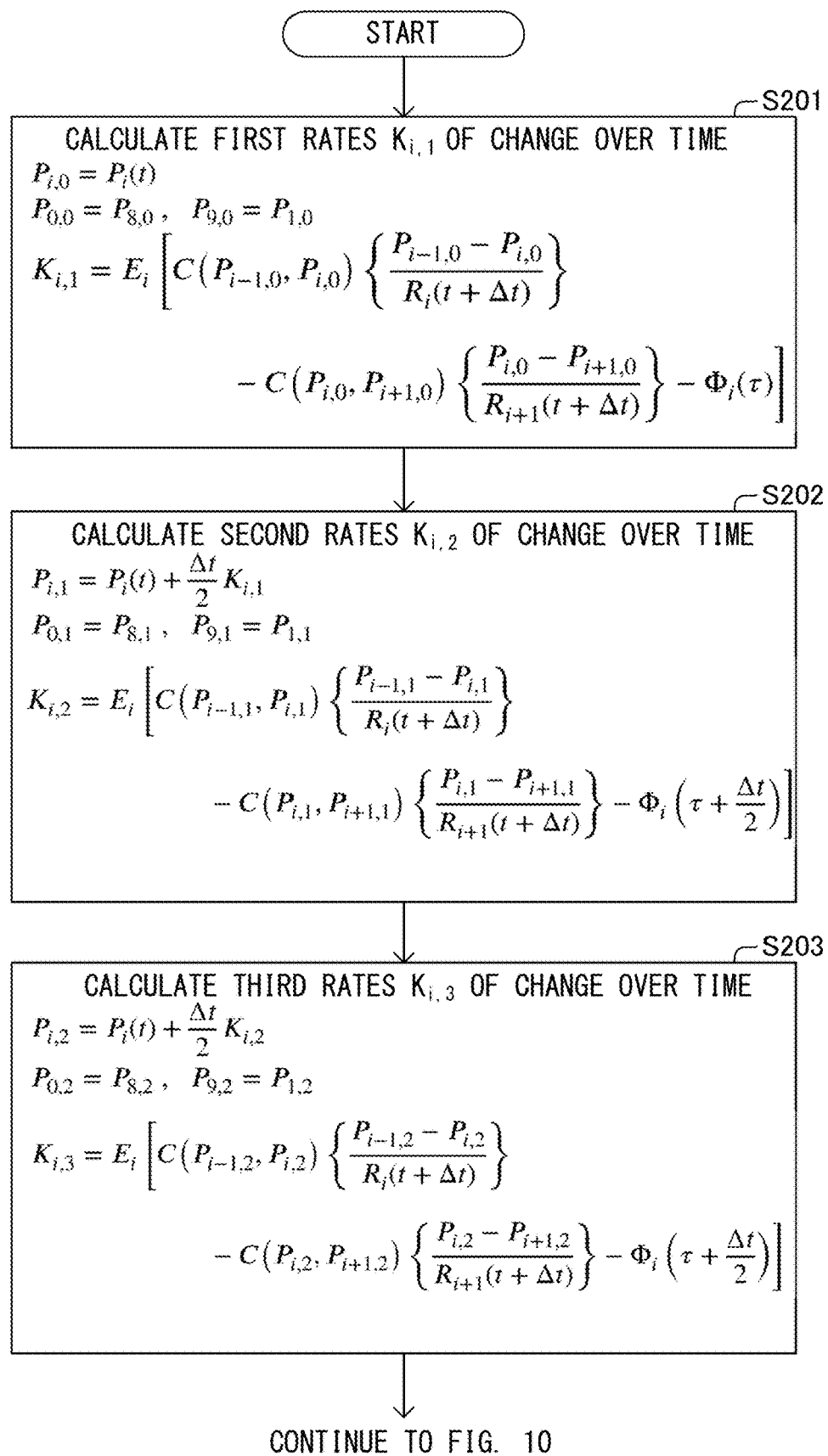
FIG. 9 is a flow diagram denoting a process performed by a processing unit of FIG. 1.
Figure 10:
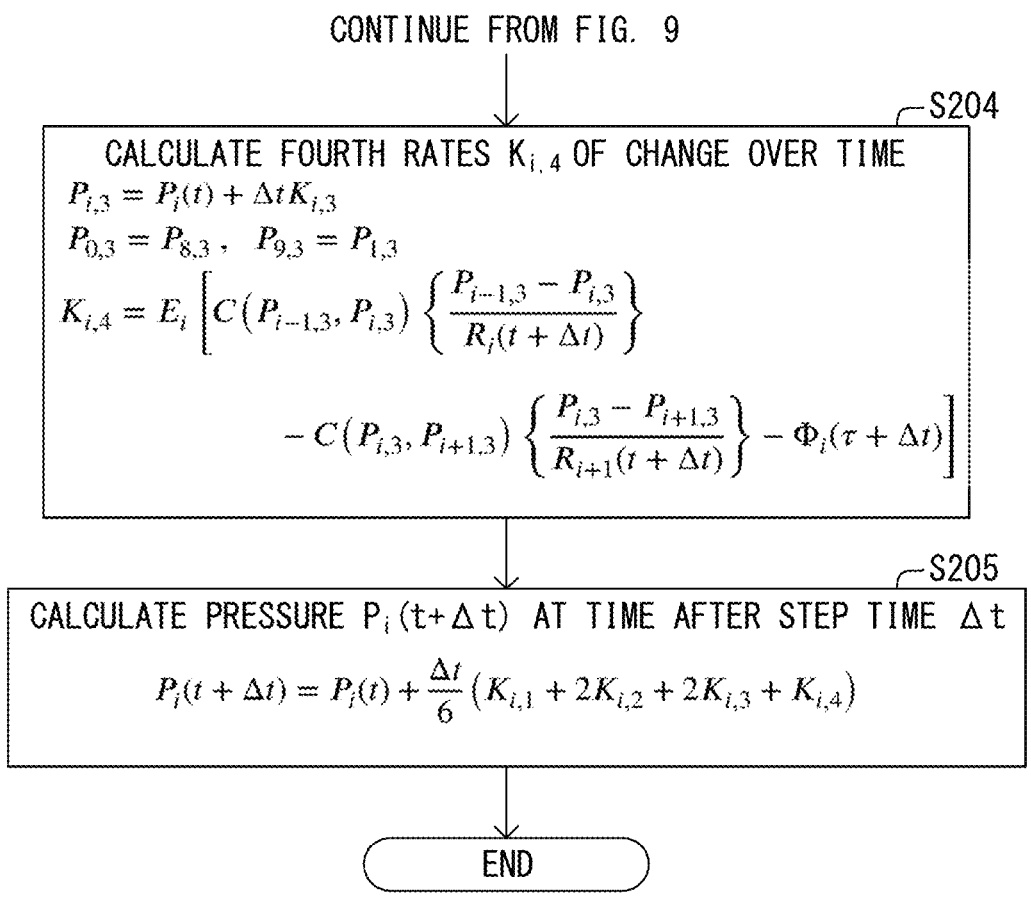
FIG. 10 is a flow diagram denoting a process performed by a processing unit of FIG. 1.

The processing unit 20 carries out the process of FIGS. 9 and 10 for the process of Step S108 of FIG. 8. Hereinafter, further description will be made in relation to the process of FIGS. 9 and 10.

The processing unit 20 sets first provisional pressures $P_{1,\ 0}$ to $P_{8,\ 0}$, which are provisional values of the pressures of the fluid in the first to the eighth vessels FV1-FV8, respectively, to the pressures $P_1(t)$ to $P_8(t)$ of the fluid in the first to the eighth vessels FV1-FV8 at the time t.

Furthermore, the processing unit 20 sets, for convenience, the first provisional pressures $P_{0,\ 0}$, $P_{9,\ 0}$ that are to be used to the first provisional pressures $P_{8,\ 0}$, $P_{1,\ 0}$, respectively. In addition, the processing unit 20 calculates first rates $K_{1,\ 1}$ to $K_{8,\ 1}$ of change over time on the basis of the first provisional pressures $P_{0,\ 0}$ to $P_{9,\ 0}$, the resistances $R_1(t+\Delta t)$ to $R_9(t+\Delta t)$ calculated in Step S107 of FIG. 8, and the time derivatives $\Phi_1(\tau)$-$\Phi_8(\tau)$ at the intra-period time $\tau$ (step S201 of FIG. 9).

Next, the processing unit 20 sets second provisional pressures $P_{1,\ 1}$ to $P_{8,\ 1}$, which are provisional values of the pressures of the fluid in the first to the eighth vessels FV1-FV8, to sums of the pressures $P_1(t)$-$P_8(t)$ of the fluid in the first to the eighth vessels FV1-FV8 at the time t and the products of the first rates $K_{1,\ 1}$ to $K_{8,\ 1}$ of change over time calculated in Step S201 of FIG. 9 and the value obtained by dividing the step time $\Delta t$ by two, respectively.

Furthermore, the processing unit 20 sets, for convenience, the second provisional pressures $P_{0,\ 1}$, $P_{9,\ 1}$ that are to be used to the second provisional pressures $P_{8,\ 1}$, $P_{1,\ 1}$, respectively. In addition, the processing unit 20 calculates second rates $K_{1,\ 2}$ to $K_{8,\ 2}$ of change over time on the basis of the second provisional pressures $P_{0,\ 1}$ to $P_{9,\ 1}$, resistances $R_1(t+\Delta t)$ to $R_9(t+\Delta t)$ calculated in Step S107 of FIG. 8, and time derivatives $\Phi_1(\tau+\Delta t/2)$ to $\Phi_8(\tau+\Delta t/2)$ at the time $\tau+\Delta t/2$ after the half of the step time $\Delta t$ from the intra-period time $\tau$ (Step S202 of FIG. 9).

Next, the processing unit 20 sets third provisional pressures $P_{1,\ 2}$ to $P_{8,\ 2}$, which are provisional values of the pressures of the fluid in the first to the eighth vessels FV1-FV8, to sums of the pressures $P_1(t)$-$P_8(t)$ of the fluid in the first to the eighth vessels FV1-FV8 at the time t and the products of the second rates $K_{1,\ 2}$ to $K_{8,\ 2}$ of change over time calculated in Step S202 of FIG. 9 and the value obtained by dividing the step time $\Delta t$ by two, respectively.

Furthermore, the processing unit 20 sets, for convenience, the third provisional pressures $P_{0,\ 2}$, $P_{9,\ 2}$ that are to be used to the third provisional pressures $P_{8,\ 2}$, $P_{1,\ 2}$, respectively. In addition, the processing unit 20 calculates third rates $K_{1,\ 3}$ to $K_{8,\ 3}$ of change over time on the basis of the third provisional pressures $P_{0,\ 2}$ and $P_{9,\ 2}$, resistances $R_1(t+\Delta t)$ to $R_9(t+\Delta t)$ calculated in Step S107 of FIG. 8, and time derivatives $\Phi_1(\tau+\Delta t/2)$ to $\Phi_8(\tau+\Delta t/2)$ at the time $\tau+\Delta t/2$ after the half of the step time $\Delta t$ from the intra-period time $\tau$ (Step S203 of FIG. 9).

Then the processing unit 20 sets fourth provisional pressures $P_{1,\ 3}$ to $P_{8,\ 3}$ that are provisional values of the pressures of the fluid in the first to the eighth vessels FV1-FV8 to sums of the pressures $P_1(t)$ to $P_8(t)$ of the fluid in the first to the eighth vessels FV1-FV8 at time t and the product of the third rates $K_{1,\ 3}$ to $K_{8,\ 3}$ of change over time calculated in Step S203 of FIG. 9, and the step time $\Delta t$, respectively.

Furthermore, the processing unit 20 sets the fourth provisional pressures $P_{0,\ 3}$, $P_{9,\ 3}$ that are to be used in the fourth provisional pressures $P_{8,3}$, $P_{1,3}$, respectively, for convenience. In addition, the processing unit 20 calculates fourth rates $K_{1,4}$ to $K_{8,4}$ of change over time on the basis of the fourth provisional pressures $P_{0,3}$, $P_{9,3}$, resistances $R_1(t+\Delta t)$ to $R_9(t+\Delta t)$ calculated in Step S107 of FIG. 8, and time derivatives $\Phi_1(\tau+\Delta t)$ to $\Phi_8(\tau+\Delta t)$ at the time $\tau+\Delta t$ after the step time $\Delta t$ from the intra-period time $\tau$ (Step S204 of FIG. 10).

Then the processing unit 20 calculates the pressures $P_1(t+\Delta t)$ to $P_8(t+\Delta t)$ of the fluid in the first to the eighth vessels FV1-FV8 at the time $t+\Delta t$ when the step time $\Delta t$ has passed since the time t on the basis of the pressures $P_1(t)$ to $P_8(t)$ of the fluid in the first to the eighth vessels FV1-FV8 at the time t and the first to the fourth rates $K_{1,1}$ to $K_{8,1}$, $K_{1,2}$ to $K_{8,2}$, $K_{1,3}$ to $K_{8,3}$, and $K_{1,4}$ to $K_{8,4}$ of change over time calculated in Steps S201 to S204 (Step S205 of FIG. 10).

Then the processing unit 20 ends the process of FIGS. 9 and 10.

As described above, the blood pressure estimating apparatus 1 of the first embodiment detects a first parameter (in the present embodiment, the pulse rate b) expressing the period length of a period of a heartbeat of the living body. Furthermore, the blood pressure estimating apparatus 1 determines, on the basis of the detected first parameter, a change (in the illustrated embodiment, the time derivatives $\Phi_2$ and $\Phi_6$ of the no-load volumes $V_2$ and $V_6$ of the second and the sixth vessels FV2 and FV6) of a no-load volume of at least one of the multiple vessels FV1-FV8 with respect to time in a mathematical model that expresses blood flowing in the circulatory system of a living body by fluid flowing through a flow path formed by annularly coupling multiple vessels FV1-FV8 that resiliently deform. Besides, the blood pressure estimating apparatus 1 estimates the blood pressure of the blood flowing in the circulatory system of a living body on the basis of the determined change and the mathematical model.

The first parameter representing a period length can be more precisely detected with ease than the artery diameter. Furthermore, using changes of the no-load volumes $V_2$ and $V_6$ of the second and the sixth vessels FV2 and FV6 with respect to time which changes are determined on the basis of the first parameter, the above mathematical model can precisely express behavior of the left ventricle and the right ventricle of the living body. Consequently, the above mathematical model can precisely express the behavior of the blood flowing in the circulatory system of a living body, so that the blood pressure estimating apparatus 1 can precisely estimate the pressure $P_i$ of the blood.

Furthermore, the blood pressure estimating apparatus 1 of the first embodiment determines, on the basis of the detected first parameter, a resistance (in the present embodiment, the resistances $R_4$ and $R_8$ against the fourth and the eighth communication pipes FC4 and FC8) which is a ratio of a difference of pressure of the fluid in a vessel between two vessels connected to each another among the multiple vessels FV1-FV8 to the flow amount of the fluid between the two vessels. In addition, the blood pressure estimating apparatus 1 estimates the pressure of the blood flowing in the circulatory system of a living body on the basis of the determined resistance.

This allows the mathematical model to more precisely express the behavior of a peripheral vascular of a living body as compared with cases where the resistances $R_4$ and $R_8$ are kept to be constant. Accordingly, the mathematical mode can precisely express the behavior of the blood flowing in the circulatory system of a living body. Consequently, the blood pressure estimating apparatus 1 can precisely estimate the pressure $P_i$ of the blood.

Furthermore, the blood pressure estimating apparatus 1 of the first embodiment determines the target value (in the present embodiment, the target resistances $g_4$ and $g_8$) of the resistance (in the present embodiment, the resistances $R_4$ and $R_8$ against the fourth and the eighth communication pipes FC4 and FC8) on the basis of the detected first parameter. In addition, the blood pressure estimating apparatus 1 determines the resistance such that the resistance approaches the determined target value with a delay.

This allows the mathematical model to further more precisely express the behavior of a peripheral vascular of a living body. Accordingly, the mathematical mode can precisely express the behavior of the blood flowing in the circulatory system of a living body. Consequently, the blood pressure estimating apparatus 1 can precisely estimate the pressure $P_i$ of the blood flowing in the circulatory system of a living body.

Furthermore, the blood pressure estimating apparatus 1 of the first embodiment detects the second parameter (in the present embodiment, the pulse amplitude a) expressing the magnitude of a heartbeat. In addition, the blood pressure estimating apparatus 1 determines the target value (in the present embodiment, the target resistances $g_4$ and $g_8$) of the resistance (in the present embodiment, the resistances $R_4$ and $R_8$ against the fourth and the eighth communication pipes FC4 and FC8) on the basis of the detected second parameter.

Here, the magnitude of a heartbeat has a strong correlation with the resistance of a peripheral vascular. This allows the blood pressure estimating apparatus 1 to further more precisely express the behavior of a peripheral vascular of a living body. Accordingly, the mathematical mode can precisely express the behavior of the blood flowing in the circulatory system of a living body. Consequently, the blood pressure estimating apparatus 1 can precisely estimate the pressure $P_i$ of the blood flowing in the circulatory system of a living body.

Furthermore, the blood pressure estimating apparatus 1 of the first embodiment determines a change (in the present embodiment, the time derivatives $\Phi_2$ and $\Phi_6$ of no-loaded volumes $V_2$ and $V_6$ of the second and the sixth vessels FV2 and FV6) of a no-load volume of at least one of the multiple vessels FV1-FV8 with respect to time on the basis of the detected second parameter.

Here, the magnitude of a heartbeat has a strong correlation with the volume of the left ventricle and the right ventricle. Along with the blood pressure estimating apparatus 1, the mathematical model can further more precisely express the behavior of the left ventricle and the right ventricle of a living body. Accordingly, the mathematical mode can precisely express the behavior of the blood flowing in the circulatory system of a living body. Consequently, the blood pressure estimating apparatus 1 can precisely estimate the pressure $P_i$ of the blood flowing in the circulatory system of a living body.

Furthermore, in the blood pressure estimating apparatus 1 of the first embodiment, the multiple vessels FV1-FV8 represent the left atrium, the left ventricle, the aorta and the artery on the downstream side of the aorta, the vena cava and the vein on the upstream side of the vena cava, the right atrium, the right ventricle, pulmonary artery, and pulmonary vein, respectively.

Accordingly, the mathematical mode can precisely express the behavior of the blood flowing in the circulatory system of a living body. Consequently, the blood pressure estimating apparatus 1 can precisely estimate the pressure $P_i$ of the blood flowing in the circulatory system of a living body.

Figure 11:
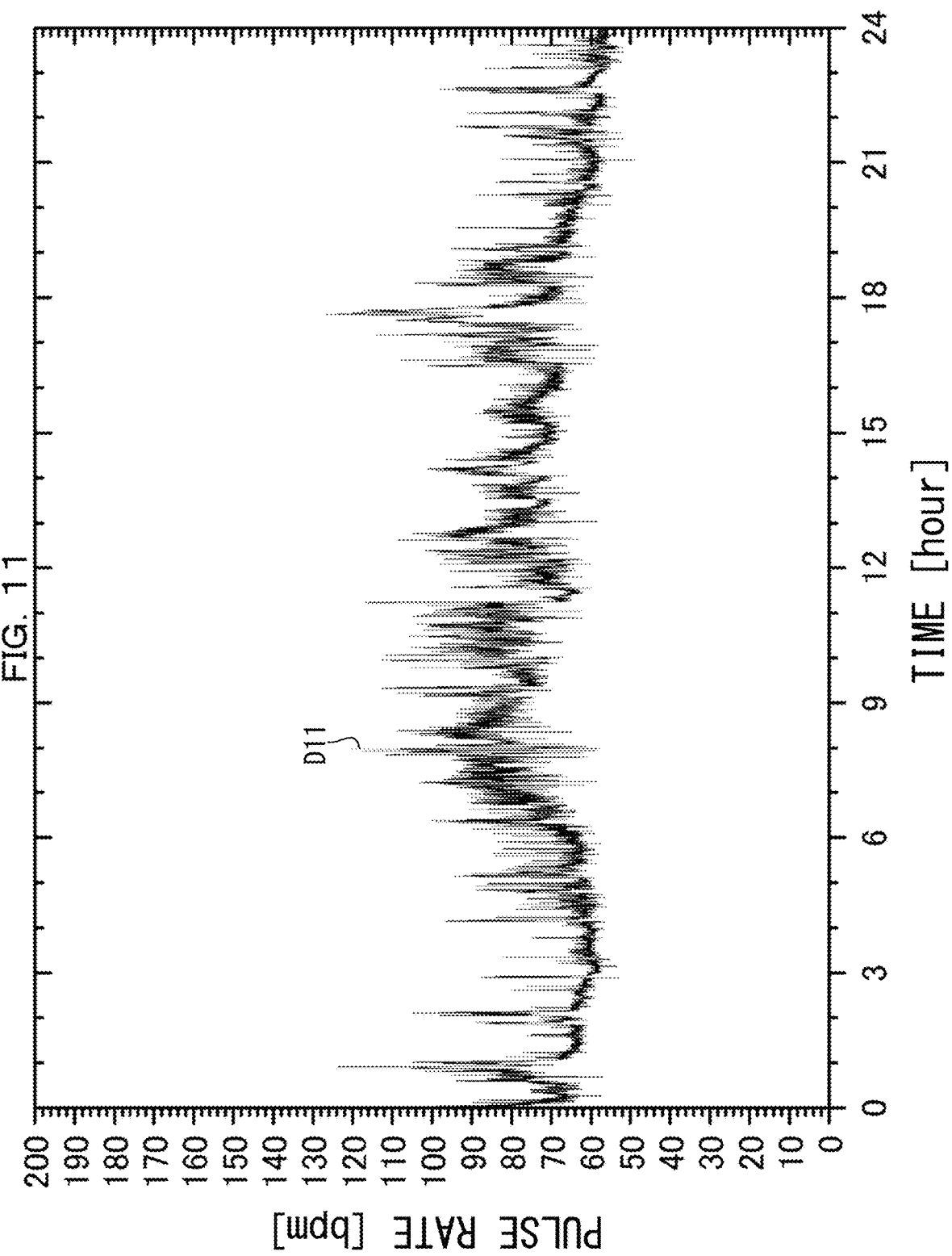
FIG. 11 is a graph illustrating an example of a change of a pulse rate detected by a detecting unit of FIG. 1 with respect to time.
Figure 12:
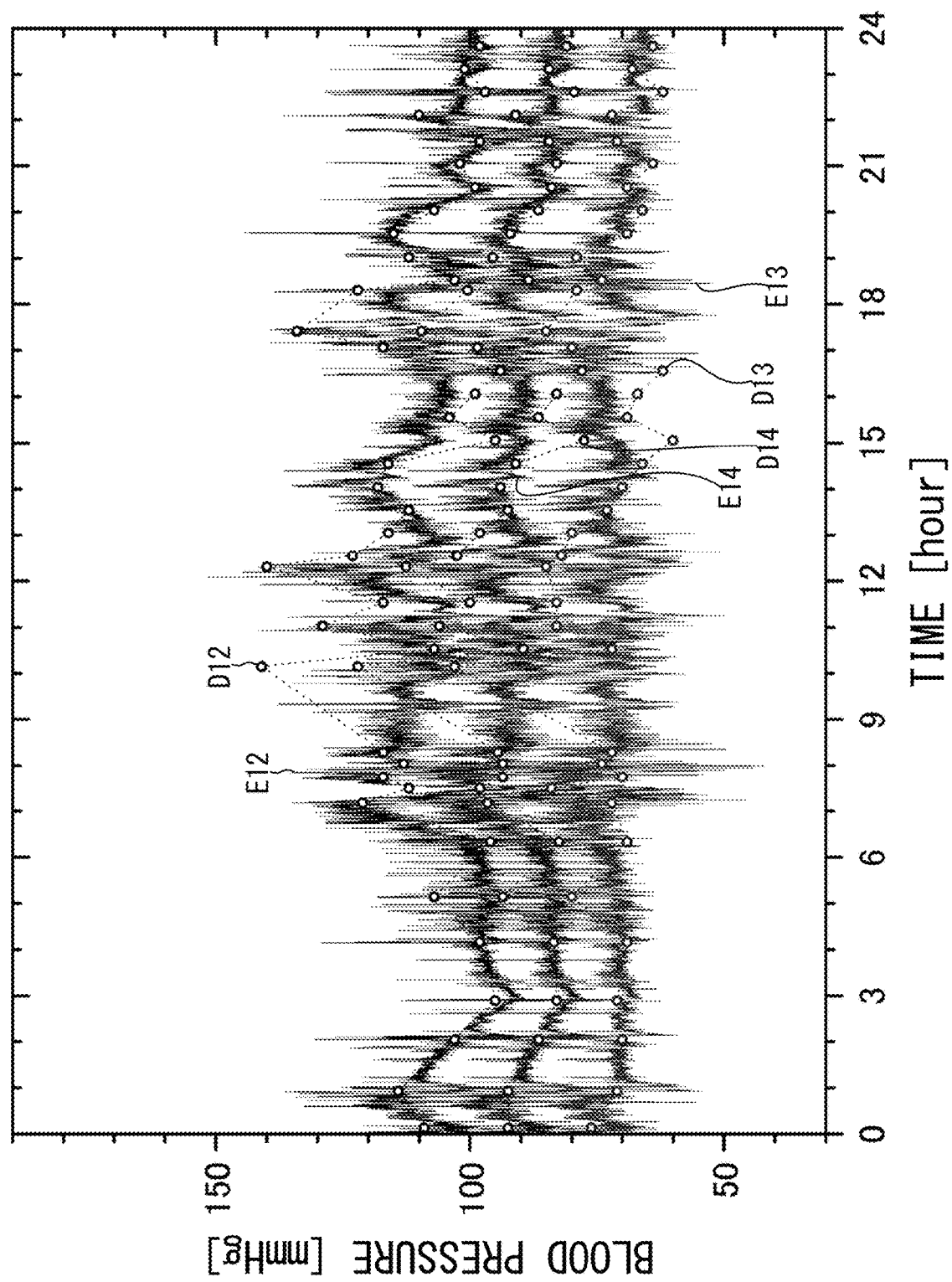
FIG. 12 is a graph illustrating an example of a change of blood pressure estimated by a processing unit of FIG. 1 with respect to time.
Figure 13:
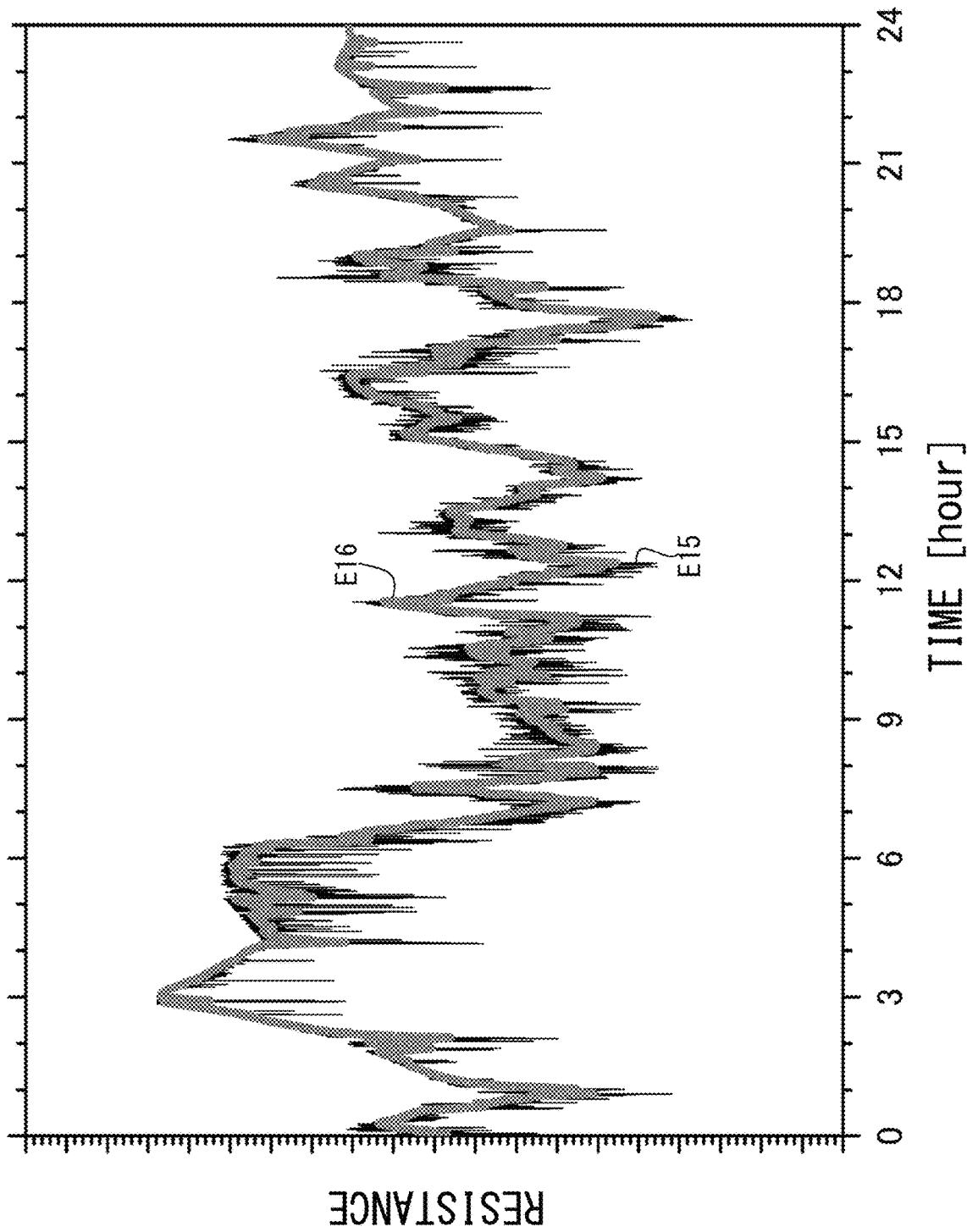
FIG. 13 is a graph illustrating an example of a change of a resistance determined by a processing unit of FIG. 1 with respect to time.
Figure 14:
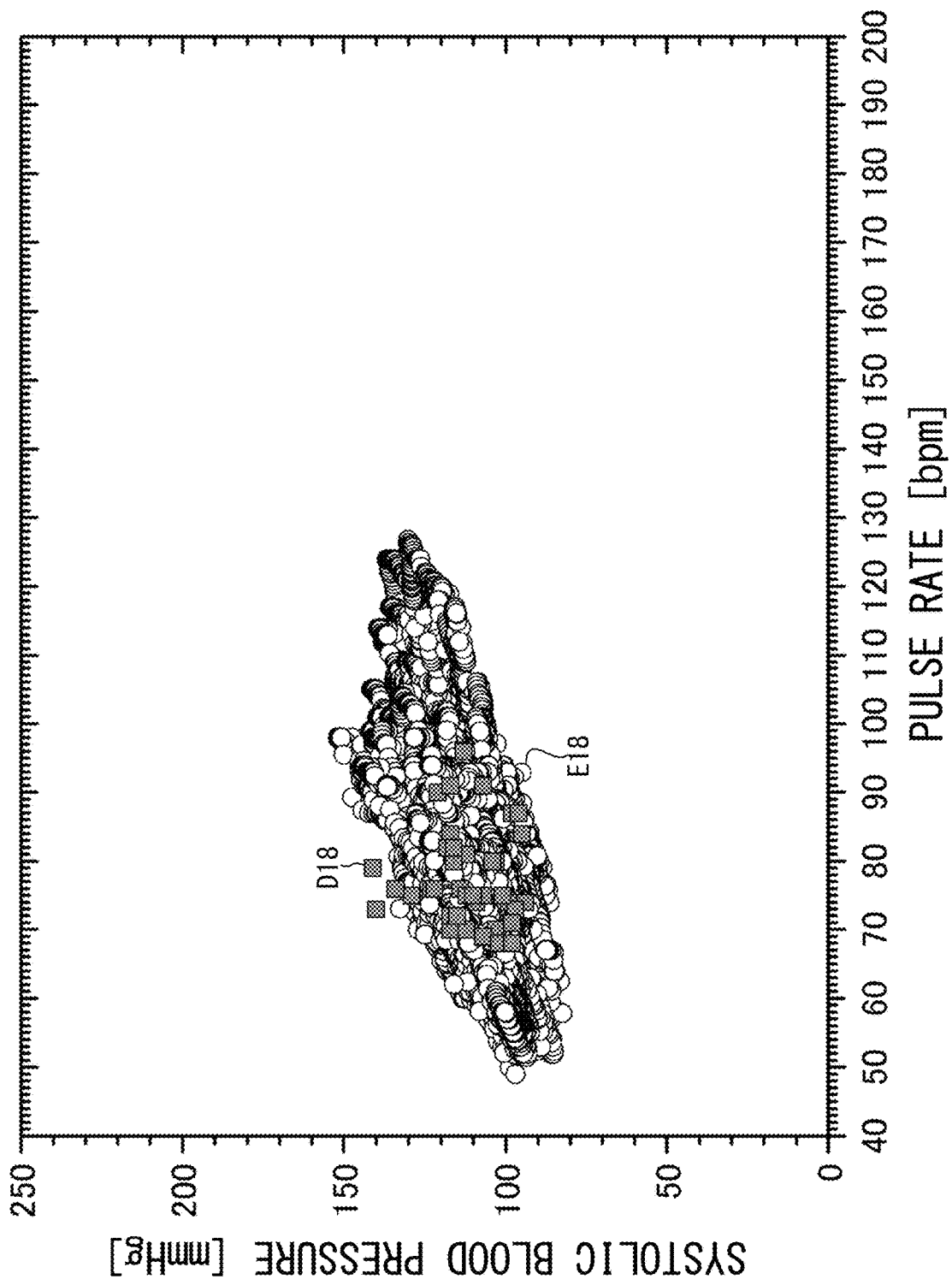
FIG. 14 is a graph illustrating an example of a relationship between a systolic blood pressure estimated by a processing unit of FIG. 1 and a pulse rate detected by a detecting unit of FIG. 1.

A curve D11 of FIG. 11 is an example of a pulse rate detected by the blood pressure estimating apparatus 1 when the living body is resting. FIGS. 12-14 are examples of results of estimating by the blood pressure estimating apparatus 1 in a case where the pulse rate detected by the blood pressure estimation apparatus 1 changes as shown in FIG. 11.

The circles D12, D13, and D14 in FIG. 12 express the systolic blood pressure (i.e., the maximum value of the blood pressure), the diastolic blood pressure (i.e., the minimum value of the blood pressure), and the average blood pressure (i.e., an average of the blood pressure) measured by a blood pressure measuring apparatus serving as a comparative example, respectively. In the present embodiment, the blood pressure measuring apparatus measures a blood pressure using a cuff. The average blood pressure has a value averaging the systolic blood pressure and the diastolic blood pressure.

The curves E12, E13, and E14 in FIG. 12 represent the systolic blood pressure, the diastolic blood pressure, and the average blood pressure estimated by the blood pressure estimating apparatus 1, respectively. As exhibited in FIG. 12, the blood pressure estimating apparatus 1 of the first embodiment can precisely estimate the blood pressure.

The curves E15 and E16 of FIG. 13 represent the target value $g_4$ of the resistance R+ against the fourth communication pipe FC4, and the resistance R+ against the fourth communication pipe FC4, respectively.

The square D18 in FIG. 14 represents the systolic blood pressure measured by a blood pressure measuring apparatus serving as a comparative example. The circle E18 in FIG. 14 represents the systolic blood pressure estimated by the blood pressure measuring apparatus. As exhibited in FIG. 14, the blood pressure estimating apparatus 1 of the first embodiment can precisely estimate the relationship between a systolic blood pressure and a pulse rate.

Figure 15:
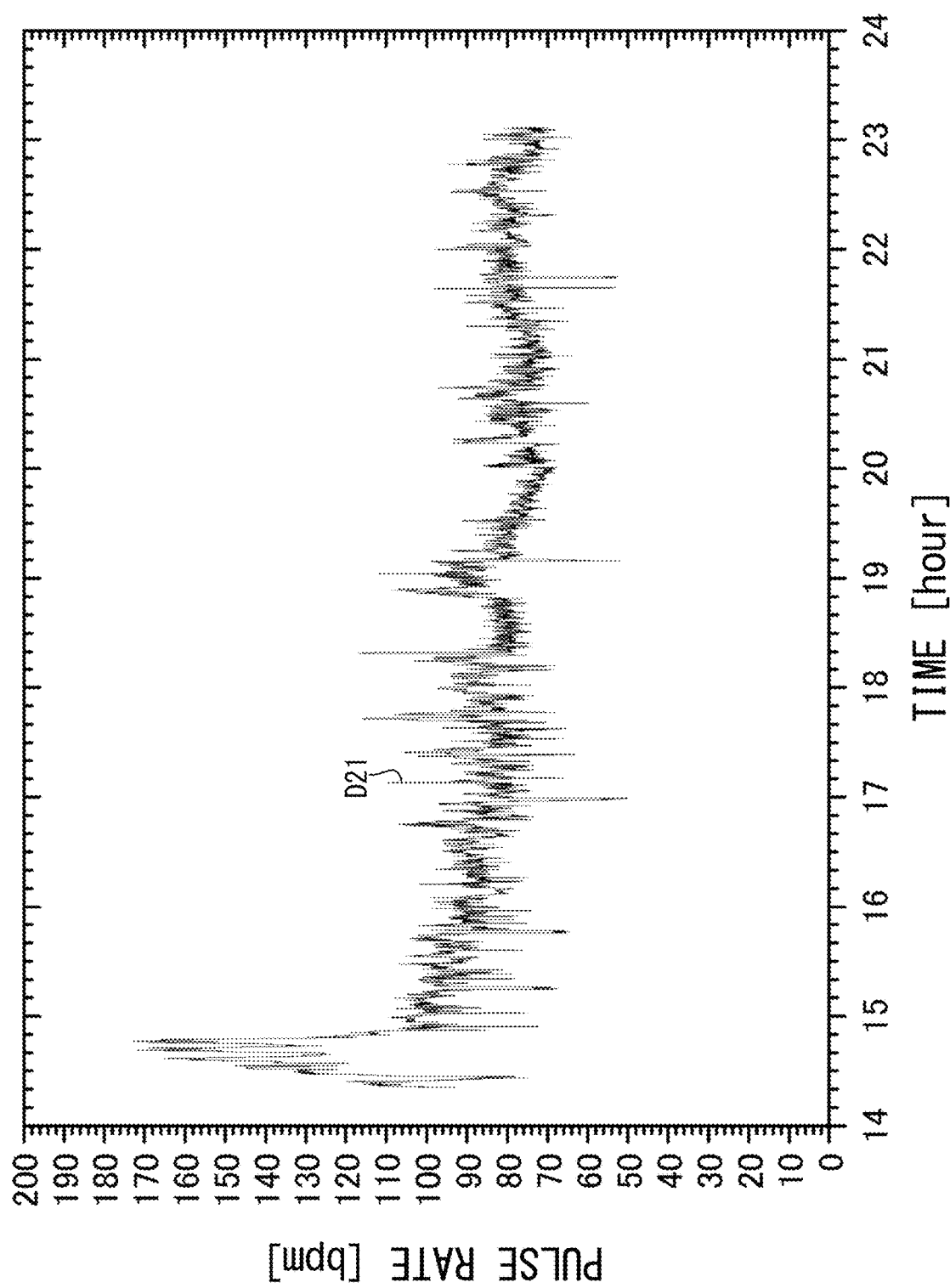
FIG. 15 is a graph illustrating an example of a change of a pulse rate detected by a detecting unit of FIG. 1 with respect to time.
Figure 16:
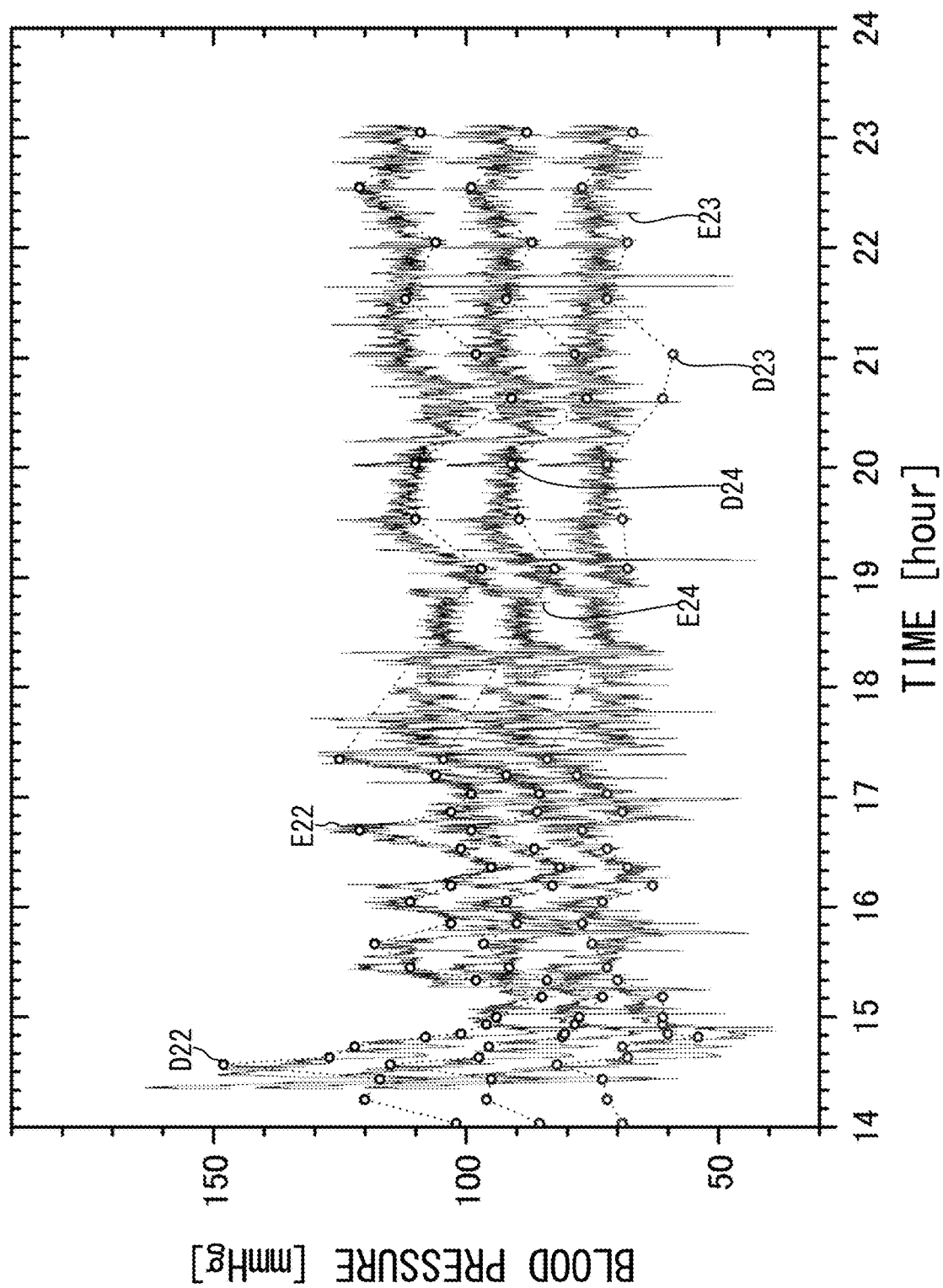
FIG. 16 is a graph illustrating an example of a change of blood pressure estimated by a processing unit of FIG. 1 with respect to time.
Figure 17:
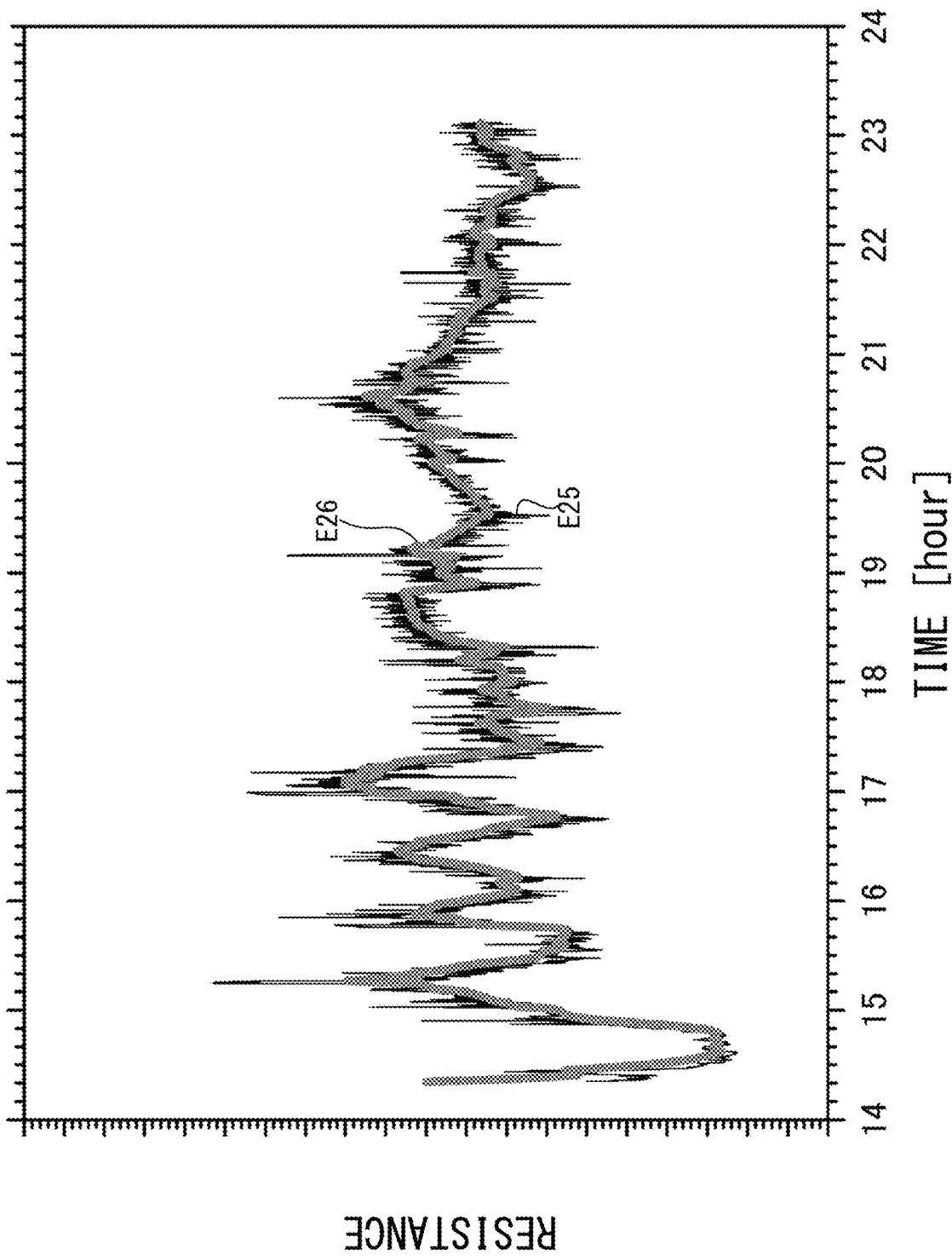
FIG. 17 is a graph illustrating a change of a resistance determined by a processing unit of FIG. 1 with respect to time.
Figure 18:
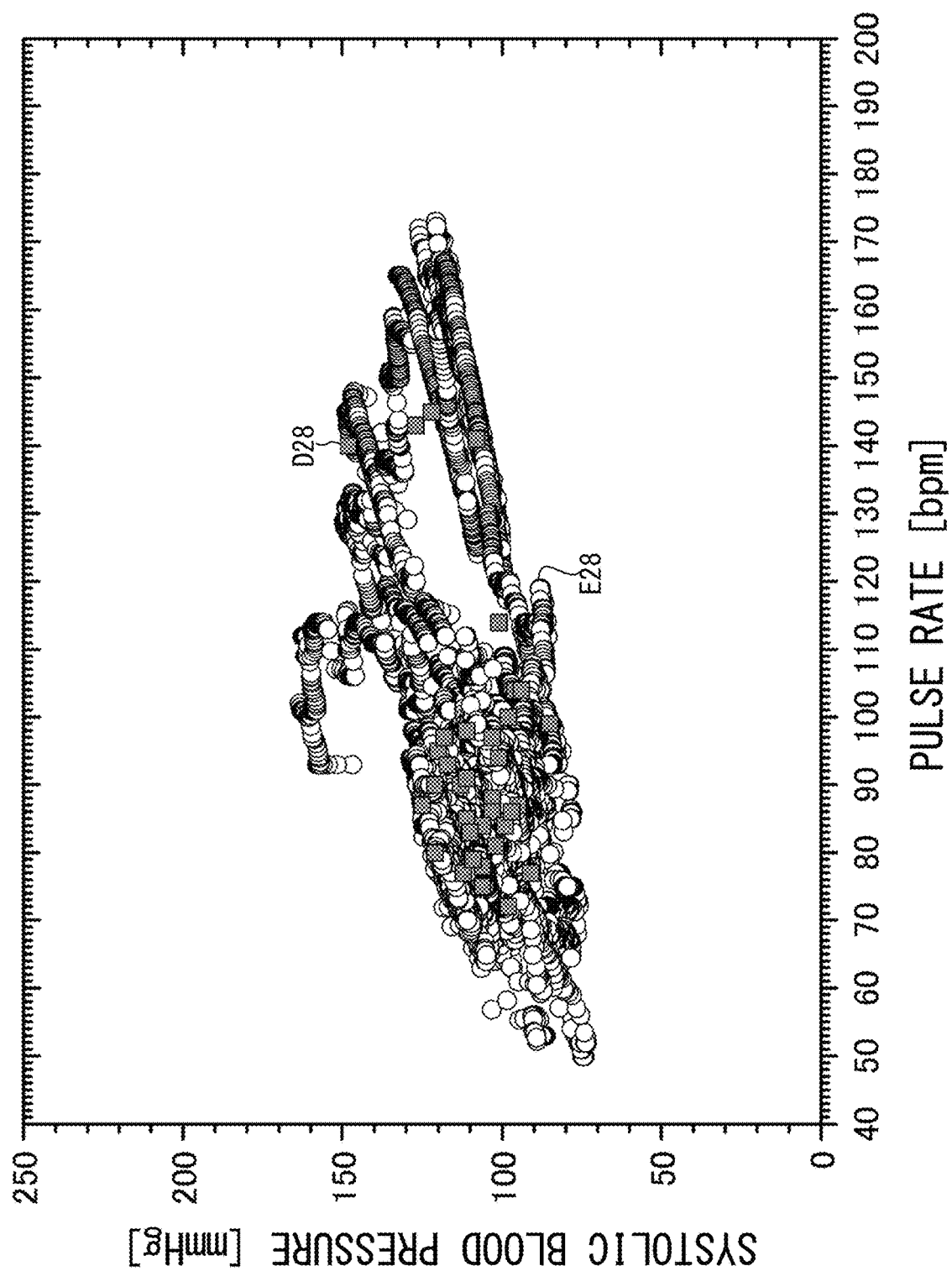
FIG. 18 is a graph illustrating an example of a relationship between a systolic blood pressure estimated by a processing unit of FIG. 1 and a pulse rate detected by a detecting unit of FIG. 1.

The curve D21 in FIG. 15 represents an example of the pulse rate detected by the blood pressure estimating apparatus 1 when the living body is on the move. FIGS. 16-18 exhibit examples of results of estimating by the blood pressure estimating apparatus 1 when the pulse rate detected by the blood pressure estimation apparatus 1 changes as shown in FIG. 15.

The circles D22, D23, and D24 in FIG. 16 express the systolic blood pressure, the diastolic blood pressure, and the average blood pressure, respectively, measured by a blood pressure measuring apparatus serving as a comparative example. In the present embodiment, the blood pressure measuring apparatus measures a blood pressure using a cuff.

The circles E22, E23, and E24 in FIG. 16 express the systolic blood pressure the diastolic blood pressure, and the average blood pressure, respectively, measured by the blood pressure estimating apparatus 1. As exhibited in FIG. 16, the blood pressure estimating apparatus 1 of the first embodiment can precisely estimate the blood pressure.

The curves E25 and E26 in FIG. 17 represent the target value $g_4$ of the resistance R+ against the fourth communication pipe FC4, and the resistance R+ against the fourth communication pipe FC4, respectively.

The square D28 in FIG. 18 represents the systolic blood pressure measured by a blood pressure measuring apparatus serving as a comparative example. The circle E28 in FIG. 18 represents the systolic blood pressure estimated by the blood pressure estimating apparatus 1. As exhibited in FIG. 18, the blood pressure estimating apparatus 1 of the first embodiment can precisely estimate the relationship between a systolic blood pressure and a pulse rate.

The blood pressure estimating apparatus 1 may include a first device serving as the detecting unit 10 and a second device serving as the processing unit 20. In this case, the first device and the second device are communicably connected to each other. In this case, the second device may be a mobile phone, a smartphone, a personal computer, and a server device.

As described above, the blood pressure estimating apparatus 1 detects the pulse rate and estimate the blood pressure at the time when the pulse rate is detected in parallel with each other. Alternatively, the blood pressure estimating apparatus 1 may estimate the blood pressure after the detection of the pulse rate has been completed, within the predetermined time length.

As described above, the blood pressure estimating apparatus 1 stores multiple different times and the respective pressures at the multiple times in association with each other. Here, the blood pressure estimating apparatus 1 may output multiple times stored therein and the respective pressures at the multiple times stored therein in association with each other. For example, the blood pressure estimating apparatus 1 may output a graph representing a change of pressure with respect to time.

The processing unit 20 may set the resistance $R_4$ and $R_8$ against the fourth and the eighth communication pipes FC4 and FC8 to the respective initial values $R_{4,\ ini}$ and $R_{8,\ ini}$, and also estimate the blood pressure without changing the resistances with respect to time.

The blood pressure estimating apparatus 1 may input information representing the pulse rate and the blood pressure of the living body measured in advance, and determine at least one of the reference target resistance $g_{i,\ 0}$, the initial value $R_{i,\ ini}$ of the resistance, and the coefficient $E_i$ on the basis of the input information.

First Modification to First Embodiment

Description will now be made in relation to a blood pressure estimating apparatus according to a first modification to the first embodiment. The blood pressure estimating apparatus according to the first modification to the first embodiment is different from the blood pressure estimating apparatus according of the first embodiment in the point that the second parameter representing the magnitude of a heartbeat is estimated on the basis of the first parameter. The following description will focus on the difference. Like reference numbers used in the first embodiment designate the same or substantially similar elements also in the first modification to the first modification.

In the present modification, the processing unit 20 estimates a pulse amplitude a on the basis of the pulse rate b detected by the detecting unit 10 and Expression 27. Furthermore, on the basis of the estimated pulse amplitude a, the processing unit 20 determines the no-load volumes $f_2$ and $f_6$ of the second and the sixth vessels FV2 and FV6, and calculates the target resistances $g_4$ and $g_8$ of the fourth and the eighth communication pipes FC4 and FC8.

$$\frac{da(t)}{dt} = \frac{1}{T_a}\left[h\left(\frac{b(t)}{b_0}\right) - a(t)\right] \qquad \text{[Expression 27]}$$

Figure 19:
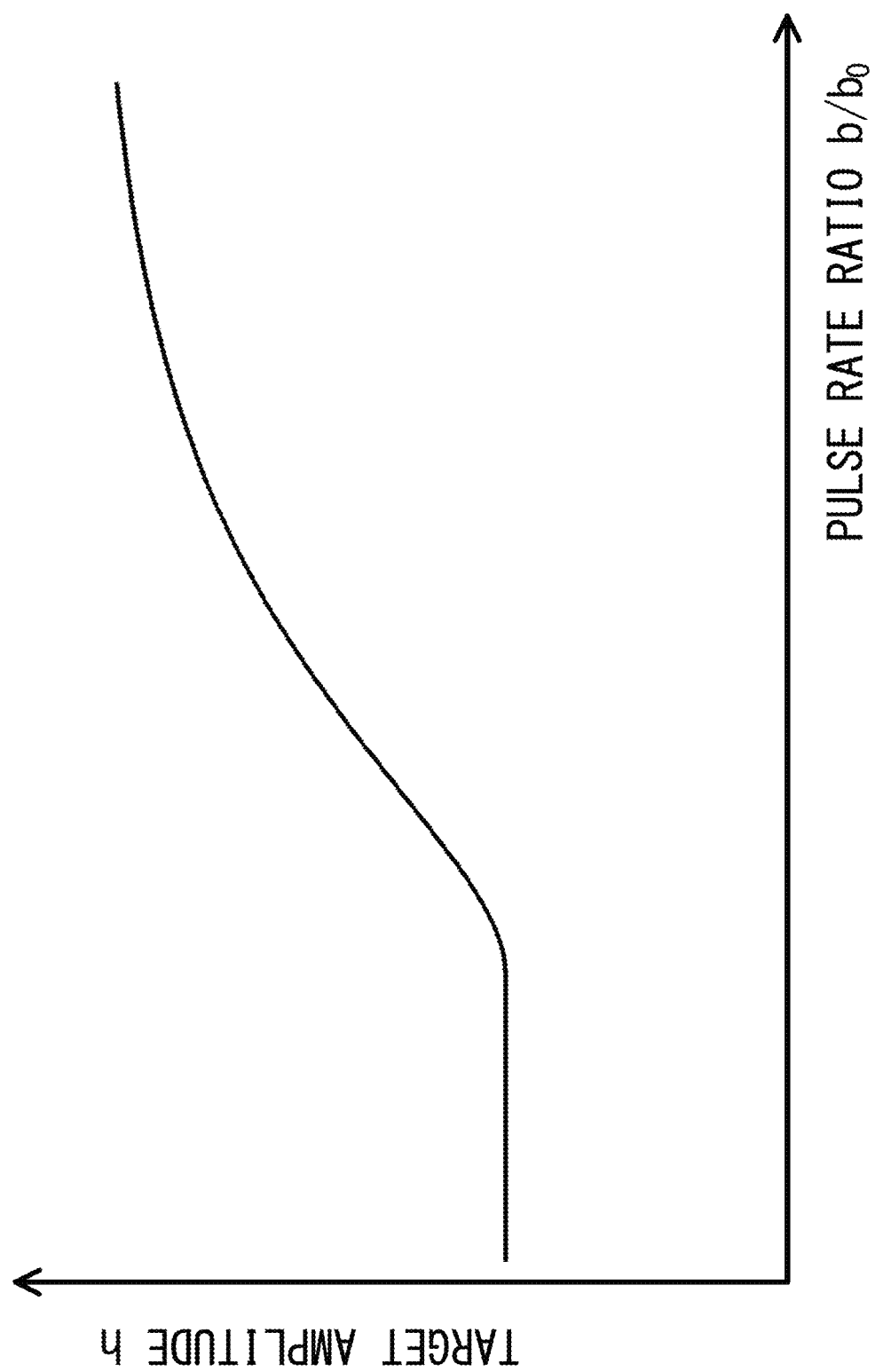
FIG. 19 is a graph illustrating an example of a change of a target amplitude stored in a processing unit of a first modification to the first embodiment with respect to a pulse rate ratio.

The term h represents the target value (i.e., target amplitude) of the pulse amplitude a. The term $T_a$ represents a time constant of a change of the pulse amplitude a. The time constant $T_a$ may be considered to express an extent of a delay of a change of the pulse amplitude a from a change of the target amplitude h. As indicated by Expression 27, the pulse amplitude a may be considered to approach the target amplitude h with a delay. The target amplitude h has a value predetermined depending on a pulse rate ration $b/b_0$. In the present modification, as indicated in FIG. 19, the target amplitude h increases as the pulse rate ration $b/b_0$ increases.

The blood pressure estimating apparatus 1 may input information representing a pulse rate and a blood pressure of the living body previously measured and determine the target amplitude h on the basis of the input information.

The estimator 203 obtains the pulse rate b(t) at a time t on the basis of the pulse rate detected by the detecting unit 10. Furthermore, the estimator 203 calculate the pulse amplitude $a(t+\Delta t)$ at time $t+\Delta t$ when the step time $\Delta t$ has passed since the time t on the basis of Expression 28, which is a difference equation of Expression 27, and obtained the pulse rate b(t). Calculating of a pulse amplitude a is an example of a estimating of a pulse amplitude a.

$$a(t + \Delta t) = a(t) + \frac{\Delta t}{T_a}\left[h\left(\frac{b(t)}{b_0}\right) - a(t)\right] \qquad \text{[Expression 28]}$$

In the present modification, the detecting unit 10 does not have to detect a second parameter that represents the magnitude of a heartbeat of the living body. The blood pressure estimating apparatus 1 of the first modification to the first embodiment brings the same effects and advantages as those of the blood pressure estimating apparatus 1 of the first embodiment.

Figure 20:
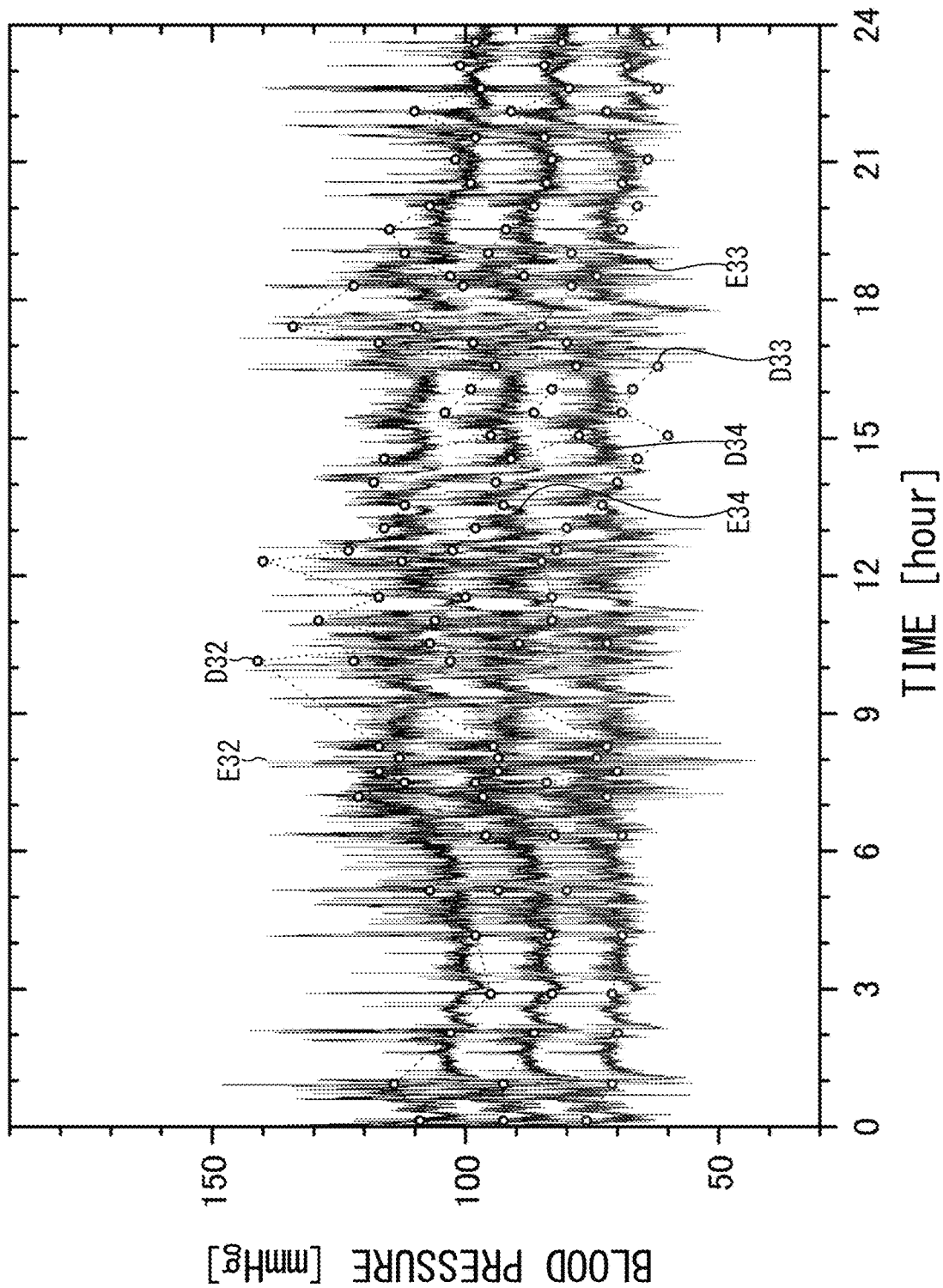
FIG. 20 is a graph illustrating an example of a change of blood pressure estimated by a processing unit of the first modification to the first embodiment with respect to time.
Figure 21:
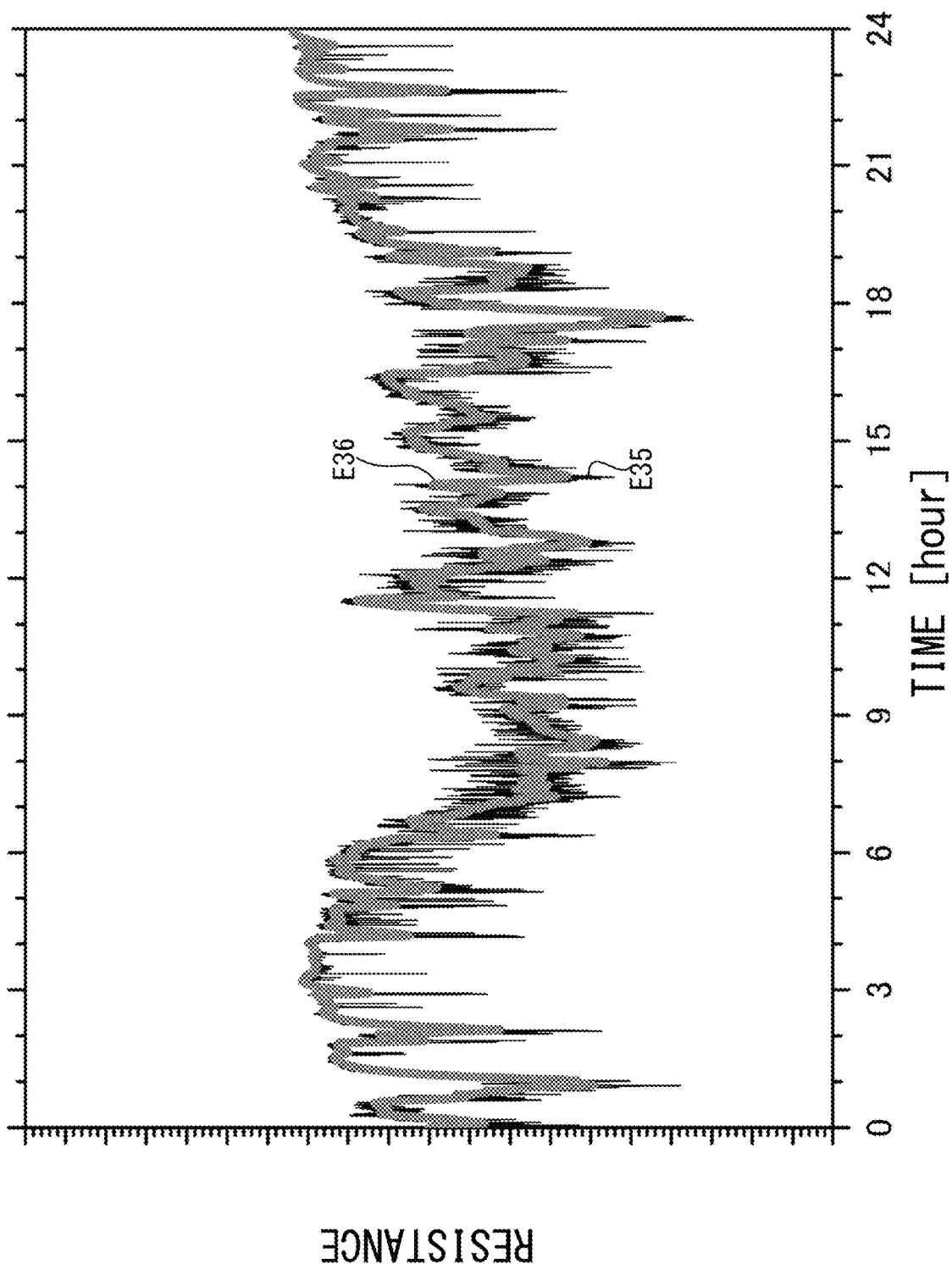
FIG. 21 is a graph illustrating a change of a resistance determined by a processing unit of the first modification to the first embodiment with respect to time.
Figure 22:
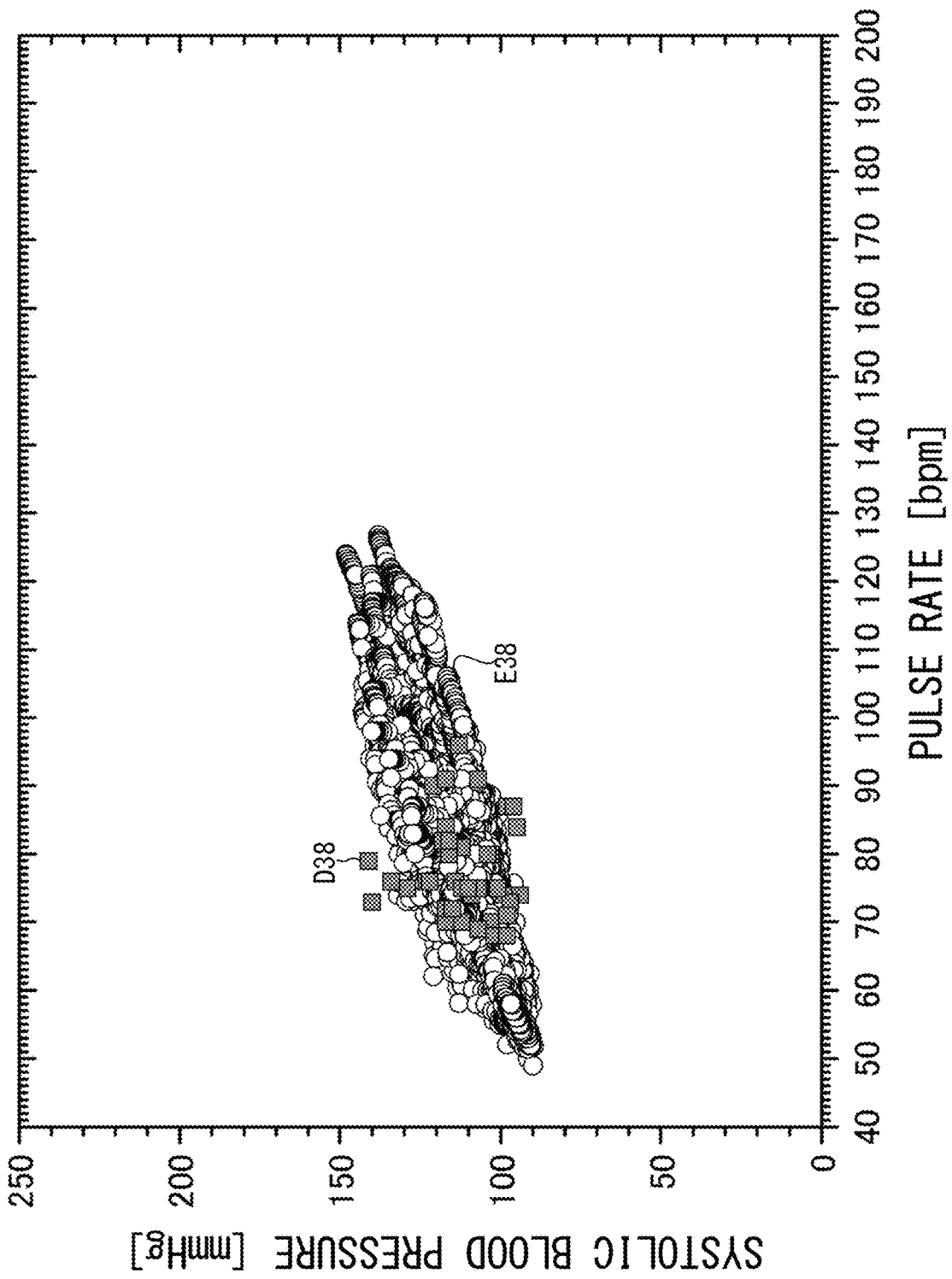
FIG. 22 is a graph illustrating an example of a relationship between the systolic blood pressure estimated by a processing unit of the first modification to the first embodiment and a pulse rate detected by a detecting unit of the first modification to the first embodiment.

FIGS. 20-22 is examples of a result of estimation by the blood pressure estimating apparatus 1 in cases where the pulse rate detected by the blood pressure estimating apparatus 1 changes as illustrated in FIG. 11.

The circles D32, D33, and D34 of FIG. 20 express the systolic blood pressure, the diastolic blood pressure, and the average blood pressure, respectively, measured by a blood pressure measuring apparatus serving as a comparative example. In the present modification, the blood pressure measuring apparatus measures a blood pressure using a cuff.

The circles E32, E33, and E34 in FIG. 20 represent the systolic blood pressure, the diastolic blood pressure, and the average blood pressure estimated by the blood pressure estimating apparatus 1, respectively. As exhibited in FIG. 20, the blood pressure estimating apparatus 1 of the first modification to the first embodiment can precisely estimate the blood pressure.

Curves E35 and E36 of FIG. 21 represent the target value $g_4$ of the resistance $R_4$ against the fourth communication pipe FC4, and the resistance $R_4$ against the fourth communication pipe FC4, respectively.

The square D38 in FIG. 22 represents the systolic blood pressure measured by a blood pressure measuring apparatus serving as a comparative example. The circle E38 in FIG. 22 represents the systolic blood pressure estimated by the blood pressure estimating apparatus 1. As exhibited in FIG. 22, the blood pressure estimating apparatus 1 of the first modification to the first embodiment can precisely estimate the relationship between a systolic blood pressure and a pulse rate.

Figure 23:
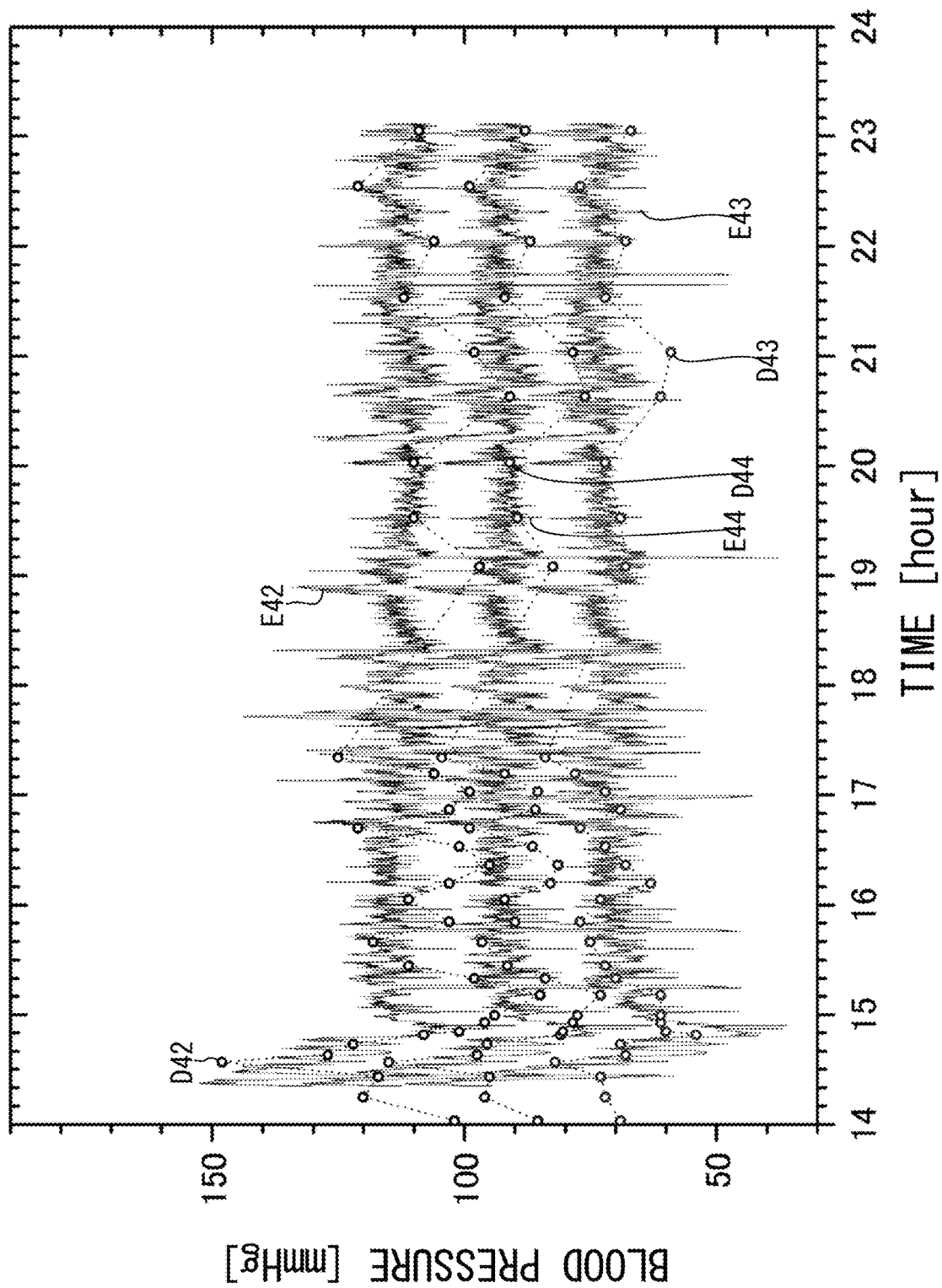
FIG. 23 is a graph illustrating an example of a change of blood pressure estimated by a processing unit of the first modification to the first embodiment with respect to time.
Figure 24:
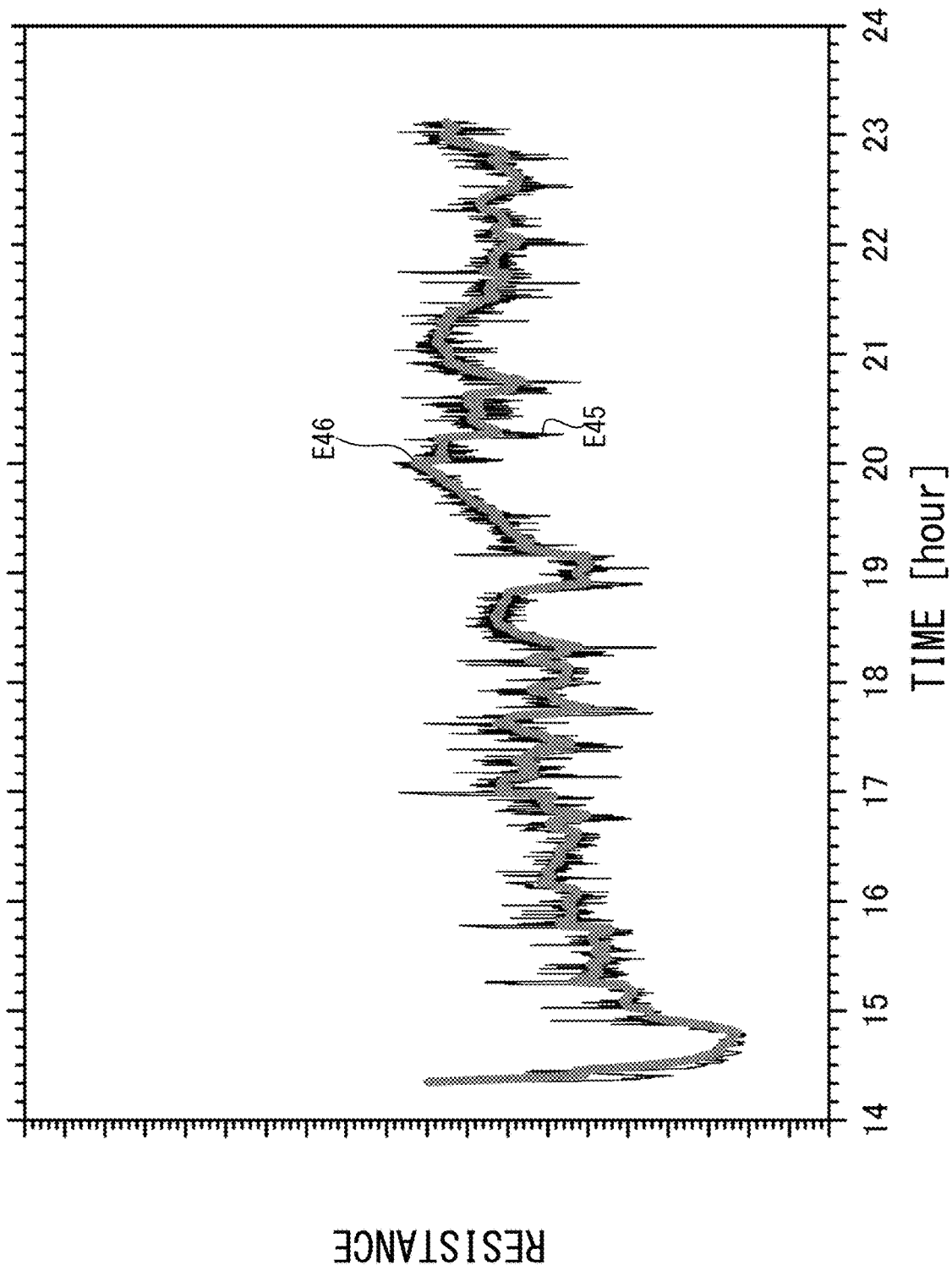
FIG. 24 is a graph illustrating a change of a resistance determined by a processing unit of the first modification to the first embodiment with respect to time.
Figure 25:
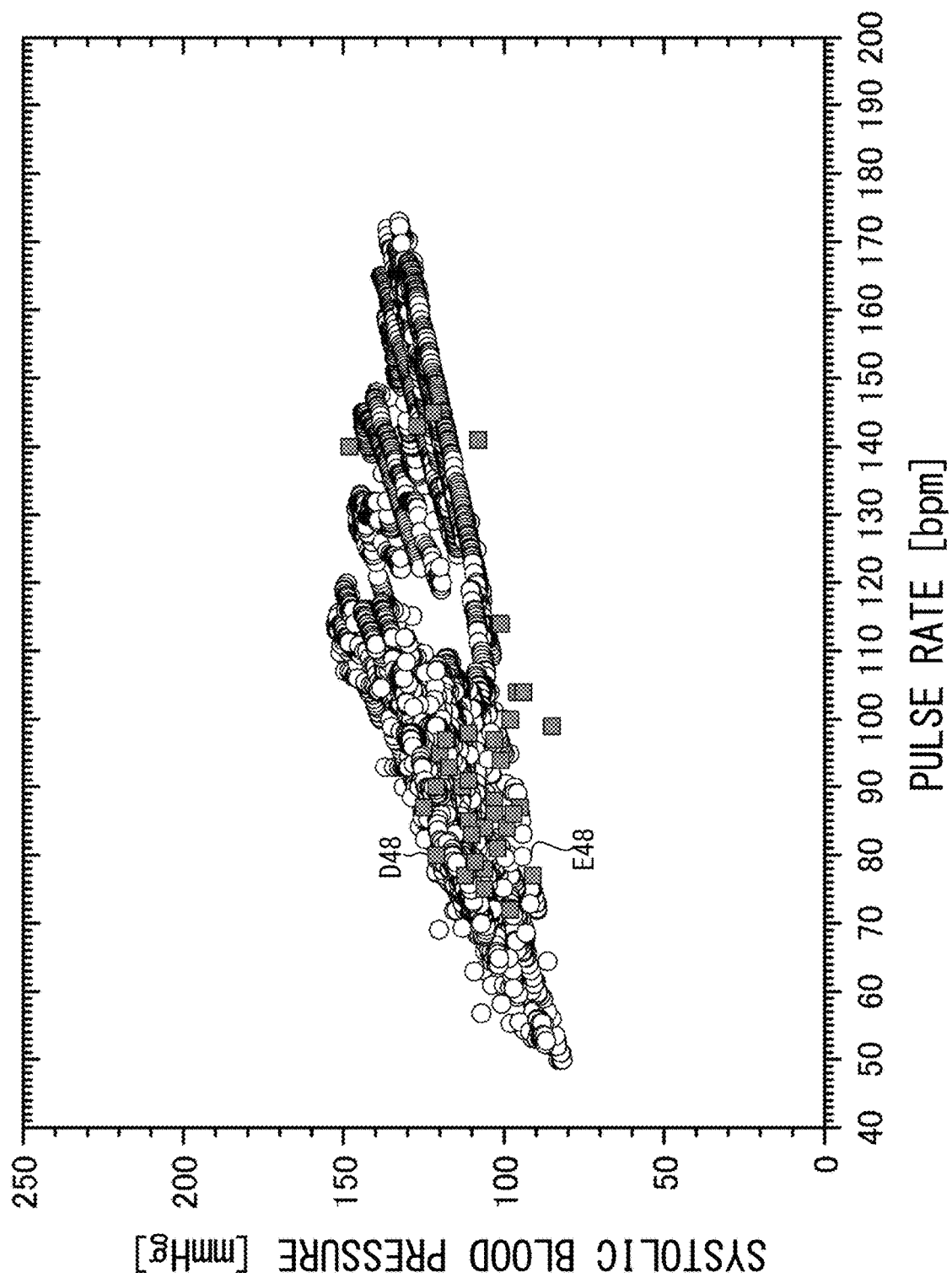
FIG. 25 is a graph illustrating an example of a relationship between the systolic blood pressure estimated by a processing unit of the first modification to the first embodiment and a pulse rate detected by a detecting unit of the first modification to the first embodiment.

FIGS. 23-25 is examples of a result of estimation by the blood pressure estimating apparatus 1 in cases where the pulse rate detected by the blood pressure estimating apparatus 1 changes as illustrated in FIG. 15.

The circles D42, D43, and D44 of FIG. 23 express the systolic blood pressure, the diastolic blood pressure, and the average blood pressure measured by a blood pressure measuring apparatus serving as a comparative example, respectively. In the present modification, the blood pressure measuring apparatus measures a blood pressure using a cuff.

The circles E42, E43, and E44 in FIG. 23 represent the systolic blood pressure, the diastolic blood pressure, and the average blood pressure estimated by the blood pressure estimating apparatus 1, respectively. As exhibited in FIG. 23, the blood pressure estimating apparatus 1 of the first modification to the first embodiment can precisely estimate the blood pressure.

Curves E45 and E46 of FIG. 24 represent the target value $g_4$ of the resistance $R_4$ against the fourth communication pipe FC4, and the resistance $R_4$ against the fourth communication pipe FC4, respectively.

The square D48 in FIG. 25 represents the systolic blood pressure measured by a blood pressure measuring apparatus serving as a comparative example. The circle E48 in FIG. 25 represents the systolic blood pressure estimated by the blood pressure estimating apparatus 1. As exhibited in FIG. 25, the blood pressure estimating apparatus 1 of the first modification to the first embodiment can precisely estimate the relationship between a systolic blood pressure and a pulse rate.

Second Modification to First Embodiment

Next, description will now be made in relation to a blood pressure estimating apparatus according to a second modification to the first embodiment. The blood pressure estimating apparatus according to the second modification to the first embodiment is different from the blood pressure estimating apparatus according of the first modification to the first embodiment in the point of calculating a reference target resistance $g_{i,0}$, a reference target resistance ratio $\gamma_i$, the resistance $R_{4,0}$ against the fourth communication pipe FC4 when the living body is resting, and a coefficient $E_4$ associated with the fourth vessel FV4, using a predetermined function. The following description will focus on the difference. Like reference numbers used in the first modification to the first embodiment designate the same or substantially similar elements also in the second modification to the first embodiment.

The processing unit 20 stores a function to calculate a reference target resistance ratio $\gamma_i$ in place of storing the reference target resistance ratio $\gamma_i$. In the present modification, the processing unit 20 stores the function indicated by Expression 29 as a function to calculate a reference target resistance ratio $\gamma_i$. The processing unit 20 calculates a reference target resistance ratio $\gamma_i$ on the basis of Expression 29.

$$\gamma_i\left(\frac{a(t)}{a_0}\right) = \frac{1}{\left(\frac{a(t)}{a_0}\right)}, \text{ where } i = 4, 8 \qquad \text{[Expression 29]}$$

The processing unit 20 stores a function to calculate a reference target resistance $g_{i,0}$ in place of storing the reference target resistance $g_{i,0}$. In the present modification, the processing unit 20 stores the function indicated by Expression 30 as a function to calculate a reference target resistance $g_{i,\,0}$. The processing unit 20 calculates a reference target resistance $g_{i,\,0}$ on the basis of Expression 30.

$$g_{i,0}\left(\frac{b(t)}{b_0}\right) = \begin{cases} R_{i,0} & \text{if } b(t) \le b_0 \\ \dfrac{R_{i,0}}{\left(\dfrac{b(t)}{b_0}\right)} & \text{if } b(t) < b_0 \end{cases} \quad \text{[Expression 30]}$$

where $i = 4, 8$

The term $R_{i,\,0}$ represents the resistance against the i-th communication pipe FCi while the living body is resting. In the present modification, the processing unit 20 calculates the resistance $R_{4,\,0}$ against the fourth communication pipe FC4 while the living body is resting on the basis of the reference value $b_0$ of the pulse rate b, the systolic blood pressure $P_{smax}$ measured while the living body is resting, the diastolic blood pressure $P_{smin}$ measured while the living body is resting, a predetermined coefficient $\alpha$, and Expression 31. For example, the reference value $b_0$ of the pulse rate b is a pulse rate measured while the living body is resting. The coefficient $\alpha$ may be changed each time the estimation of a blood pressure is carried out. The coefficient $\alpha$ may be set to a value according to the living body.

$$R_{4,0} = \alpha \frac{P_{smax} + P_{smin}}{b_0} \quad \text{[Expression 31]}$$

In the present modification, the processing unit 20 calculates a coefficient $E_4$ associated with the fourth vessel FV4 on the basis of the systolic blood pressure $P_{smax}$ measured while the living body is resting, the diastolic blood pressure $P_{smin}$ measured while the living body is resting, a predetermined coefficient $\beta$, and Expression 32. The coefficient $\beta$ may be changed each time the estimation of a blood pressure is carried out. The coefficient $\beta$ may be set to a value according to the living body.

$$E_4 = \beta(P_{smax} - P_{smin}) \quad \text{[Expression 32]}$$

In the present embodiment, the processing unit 20 uses a fixed value (i.e., a value commonly used for multiple different living bodies) as a resistance $R_{8,\,0}$ against the eighth communication pipe FC8. The resistance $R_{8,\,0}$ against the eighth communication pipe FC8 may be changed each time the estimation of the blood pressure is carried out. The resistance $R_{8,\,0}$ against the eighth communication pipe FC8 may be set to a value according to the living body.

In the present modification, the processing unit 20 uses a fixed value as a coefficient $E_j$ associated with the j-th vessel FV$_j$. The symbol j represents each of integers of one to eight except for four. The coefficient E associated with the j-th vessel FV$_j$ may be changed each time the estimation of a blood pressure is carried out. The coefficient $E_j$ associated with the j-th vessel FV$_j$ may be set to a value according to the living body.

The blood pressure estimating apparatus 1 of the second modification to the first embodiment brings the same effects and advantages as those of the blood pressure estimating apparatus 1 of the first modification to the first embodiment.

FIGS. 26-29 are examples of results of estimation by the blood pressure estimating apparatus 1 in cases where the pulse rate detected by the blood pressure estimating apparatus 1 changes as illustrated in FIG. 11.

Figure 26:
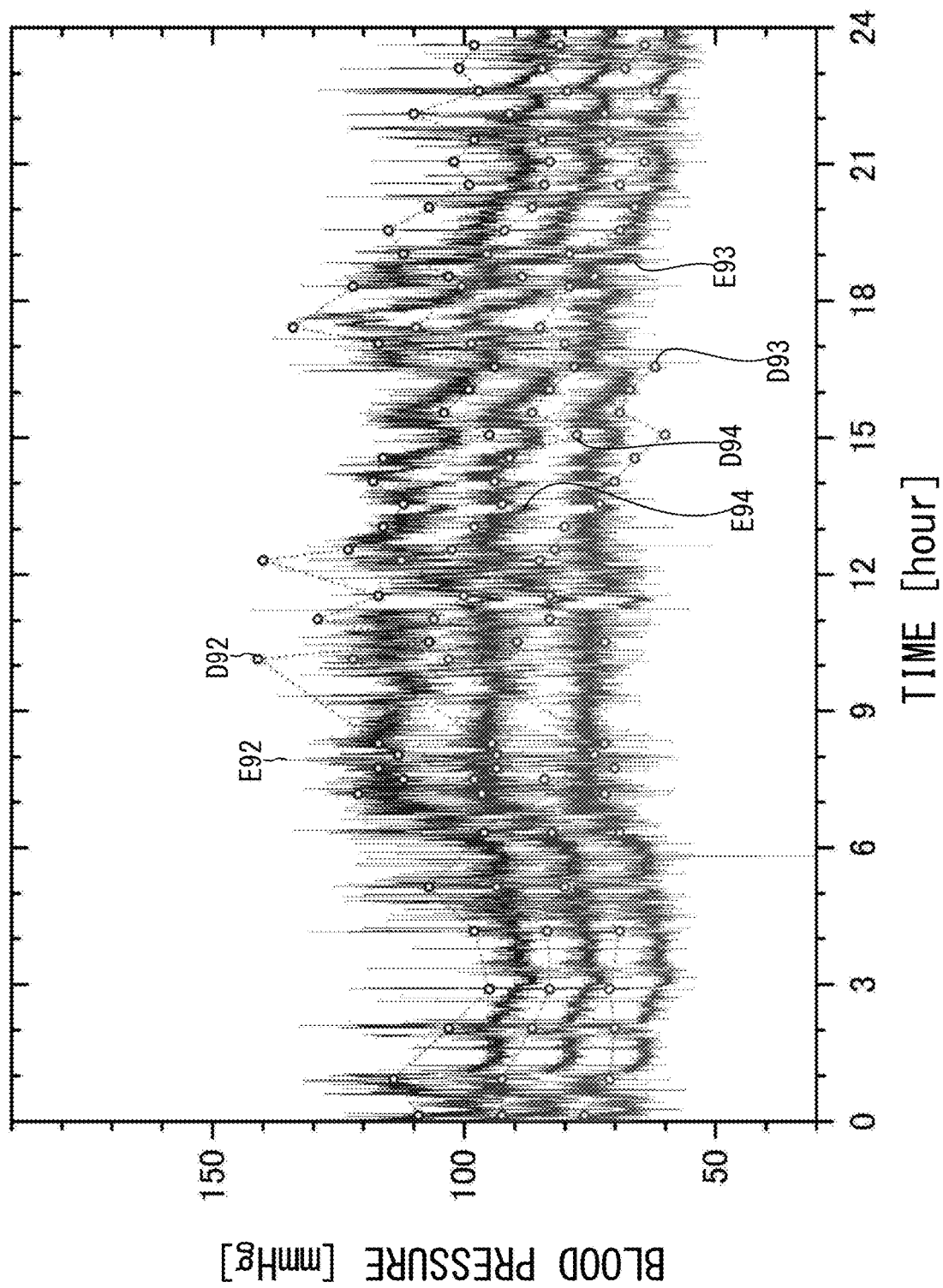
FIG. 26 is a graph illustrating an example of a change of blood pressure estimated by a processing unit of a second modification to the first embodiment with respect to time.

The circles D92, D93, and D94 of FIG. 26 express the systolic blood pressure, the diastolic blood pressure, and the average blood pressure measured by a blood pressure measuring apparatus serving as a comparative example, respectively. In the present modification, the blood pressure measuring apparatus measures a blood pressure using a cuff.

The circles E92, E93, and E94 in FIG. 26 represent the systolic blood pressure, the diastolic blood pressure, and the average blood pressure estimated by the blood pressure estimating apparatus 1, respectively. As exhibited in FIG. 26, the blood pressure estimating apparatus 1 of the second modification to the first embodiment can precisely estimate a blood pressure.

Figure 27:
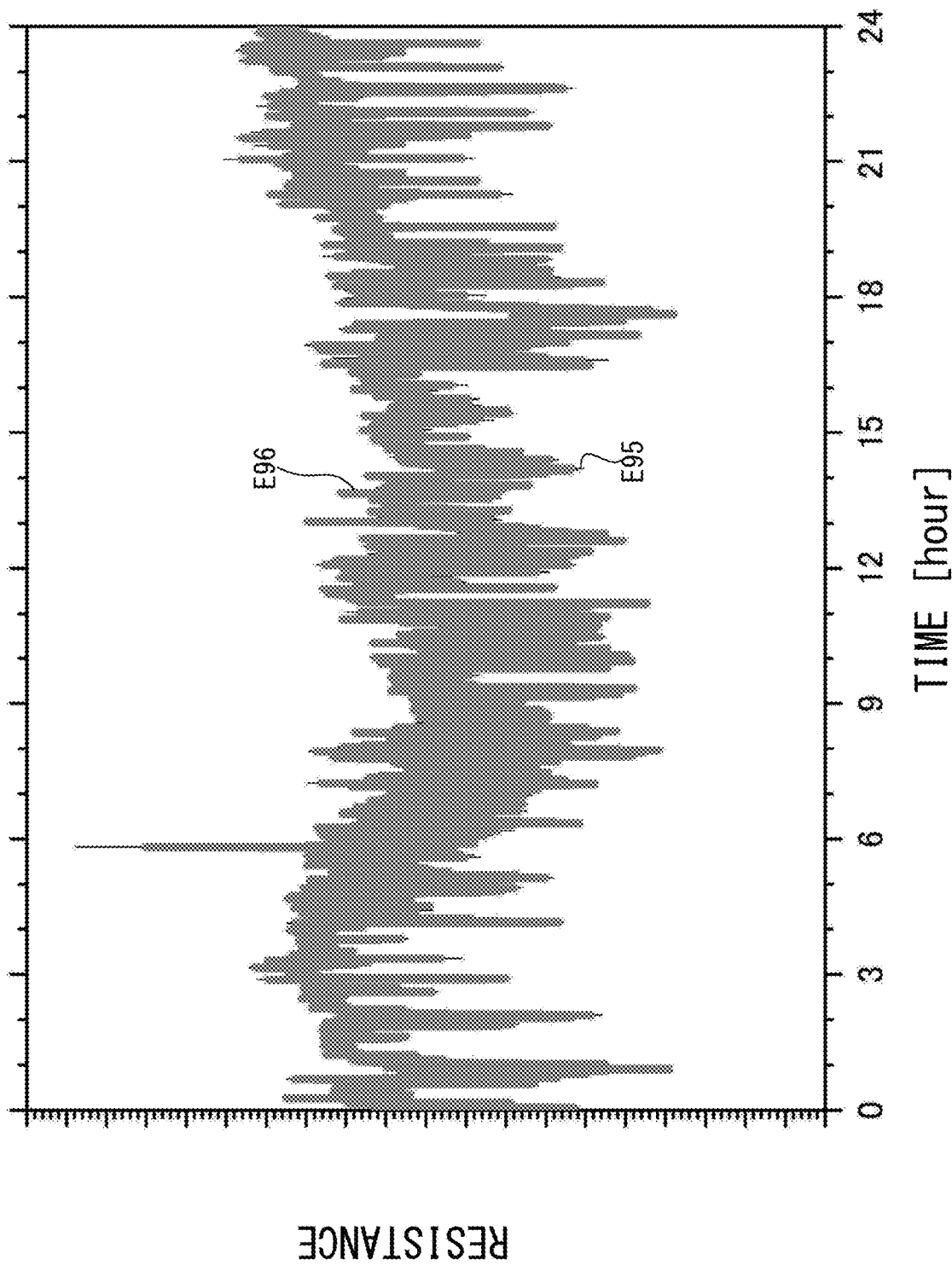
FIG. 27 is a graph illustrating a change of a resistance determined by a processing unit of the second modification to the first embodiment with respect to time.

The curves E95 and E96 of FIG. 27 represent the target value $g_4$ of the resistance $R_4$ against the fourth communication pipe FC4, and the resistance $R_4$ against the fourth communication pipe FC4, respectively.

Figure 28:
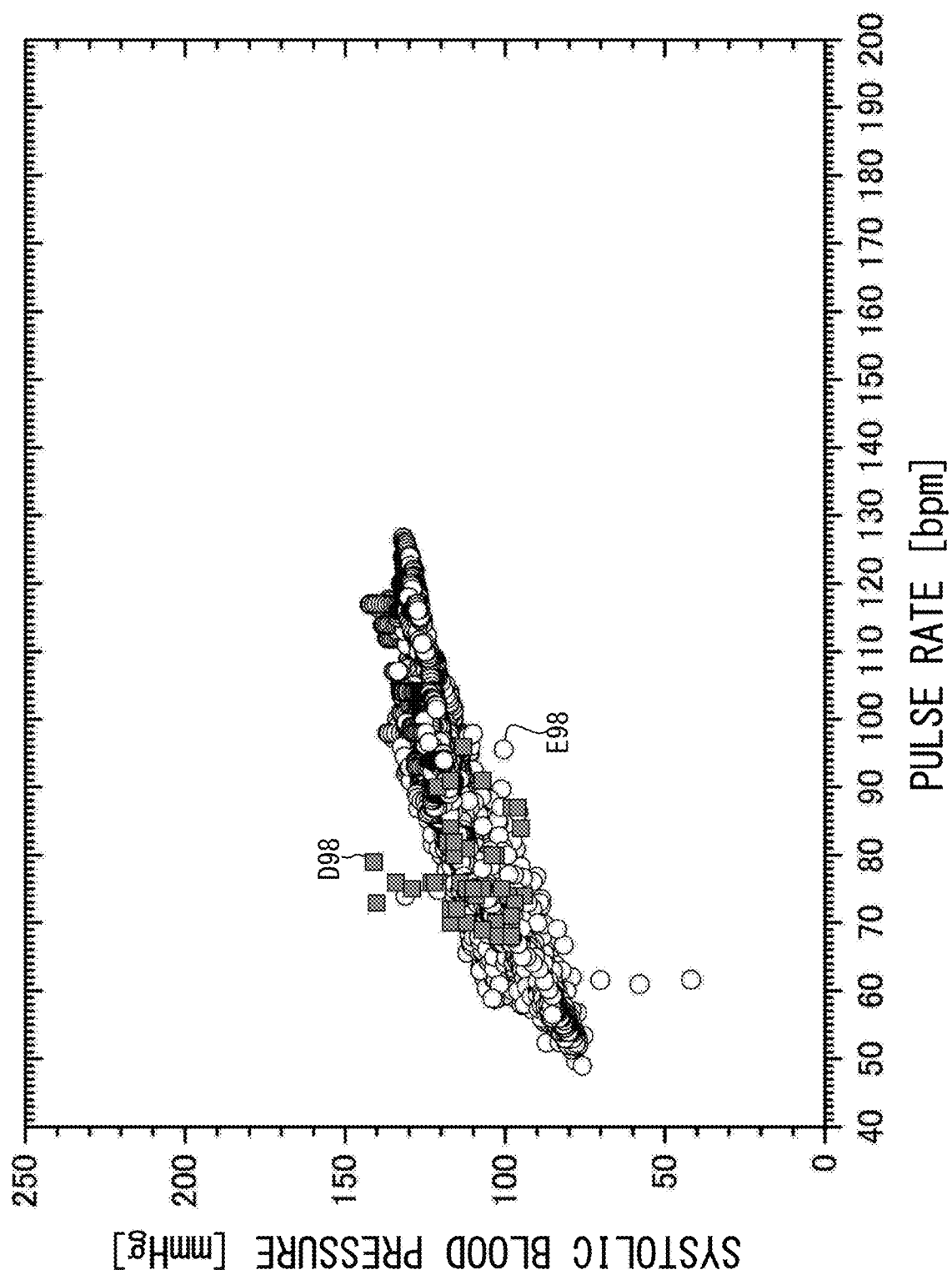
FIG. 28 is a graph illustrating an example of a relationship between the systolic blood pressure estimated by a processing unit of the second modification to the first embodiment and a pulse rate detected by a detecting unit of the second modification to the first embodiment.

The square D98 in FIG. 28 represents the systolic blood pressure measured by a blood pressure measuring apparatus serving as a comparative example. The circle E98 in FIG. 28 represents the systolic blood pressure estimated by the blood pressure estimating apparatus 1. As exhibited in FIG. 28, the blood pressure estimating apparatus 1 of the second modification to the first embodiment can precisely estimate the relationship between a systolic blood pressure and a pulse rate.

Figure 29:
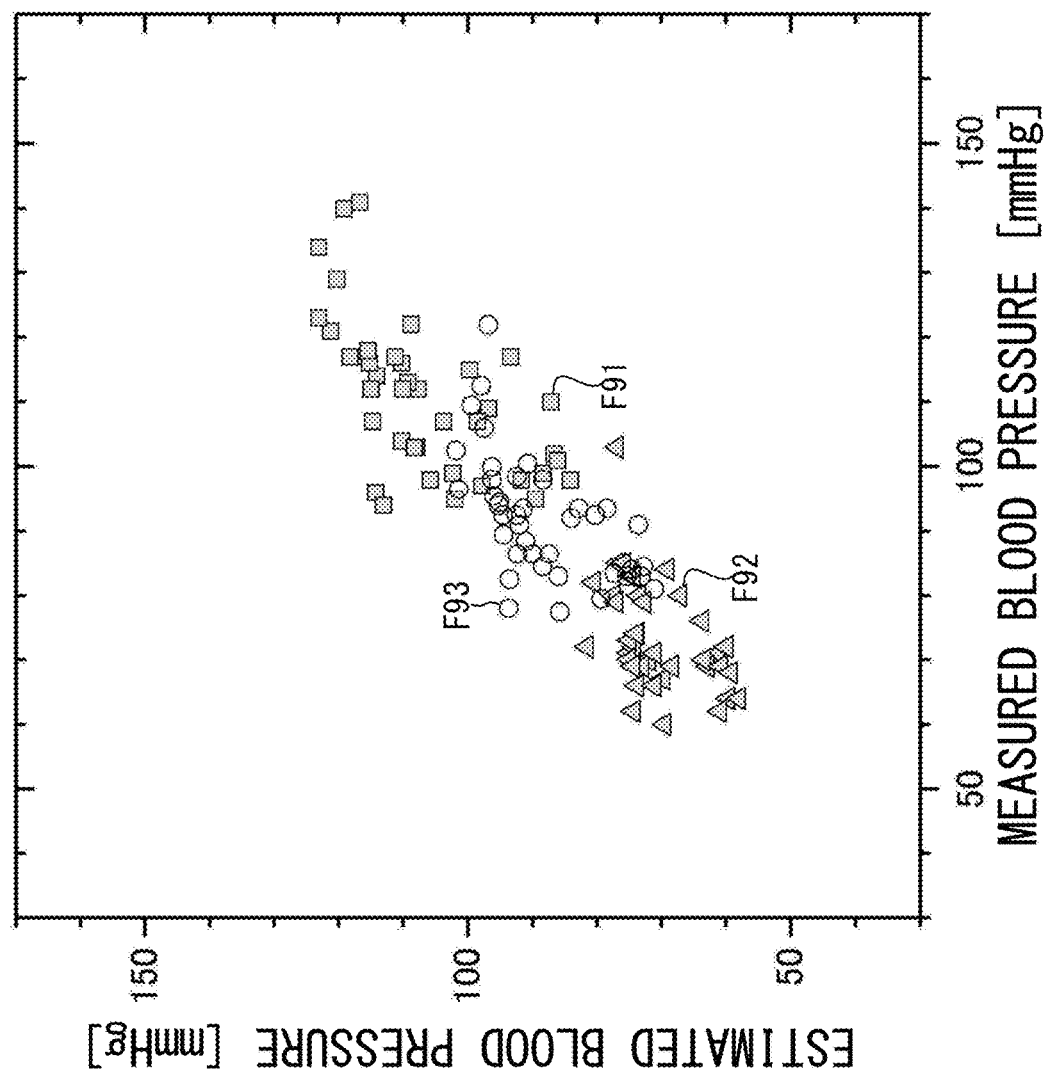
FIG. 29 is a graph illustrating an example of a relationship between blood pressure estimated by a processing unit of the second modification to the first embodiment and blood pressure measured by a blood pressure measuring apparatus serving as a comparative example.

A blood pressure measured by the blood pressure measuring apparatus is represented by "measured blood pressure" and a blood pressure estimated by the blood pressure estimating apparatus 1 is represented by "estimated blood pressure" in FIG. 29. The square F91 in FIG. 29 represents relationship between a systolic blood pressure measured by a blood pressure measuring apparatus serving as a comparative example and a systolic blood pressure estimate by the blood pressure estimating apparatus 1. The triangle F92 in FIG. 29 represents a relationship between a diastolic blood pressure measured by the blood pressure measuring apparatus serving as a comparative example and a diastolic blood pressure estimate by the blood pressure estimating apparatus 1. The circle F93 in FIG. 29 represents a relationship between an average pressure measured by the blood pressure measuring apparatus serving as a comparative example and an average blood pressure estimate by the blood pressure estimating apparatus 1. As exhibited in FIG. 29, the blood pressure estimating apparatus 1 of the second modification to the first embodiment can precisely estimate a systolic blood pressure, a diastolic blood pressure, and an average blood pressure.

Third Modification to First Embodiment

Next, description will now be made in relation to a blood pressure estimating apparatus according to a third modification to the first embodiment. The blood pressure estimating apparatus according to the third modification to the first embodiment is different from the blood pressure estimating apparatus according of the first embodiment in the point of estimating a blood pressure not based on a second parameter representing the magnitude of a heartbeat. The following description will focus on the difference. Like reference numbers used in the first embodiment designate the same or substantially similar elements also in the third modification to the first embodiment.

The processing unit 20 uses the reference value $a_0$ of the pulse amplitude a in place of the pulse amplitude $a(t)$ at the time t. In other words, the present modification expresses the no-load volumes $f_2$ and $f_6$ of the second and the sixth vessels FV2 and FV6 with Expression in place of Expression 3.

$$f_i(a_0, b(t), \tau(t)) = f_{i,0}\left(\frac{b(t)}{b_0}\tau(t)\right), \quad \text{[Expression 33]}$$

where $i = 2, 6$

The target values $g_4$ and $g_8$ of the resistances $R_4$ and $R_8$ against the fourth and eighth communication pipes FC4 and FC8 are indicated by Expression 34 in place of Expression 9.

$$g_i(a_0, b(t)) = g_{i,0}\left(\frac{b(t)}{b_0}\right), \quad \text{[Expression 34]}$$

where $i = 4, 8$

In the present modification, the detecting unit 10 does not have to detect a second parameter representing the magnitude of a heartbeat of the living body.

The blood pressure estimating apparatus 1 of the third modification to the first embodiment brings the same effects and advantages as those of the blood pressure estimating apparatus 1 of the first embodiment.

Figure 30:
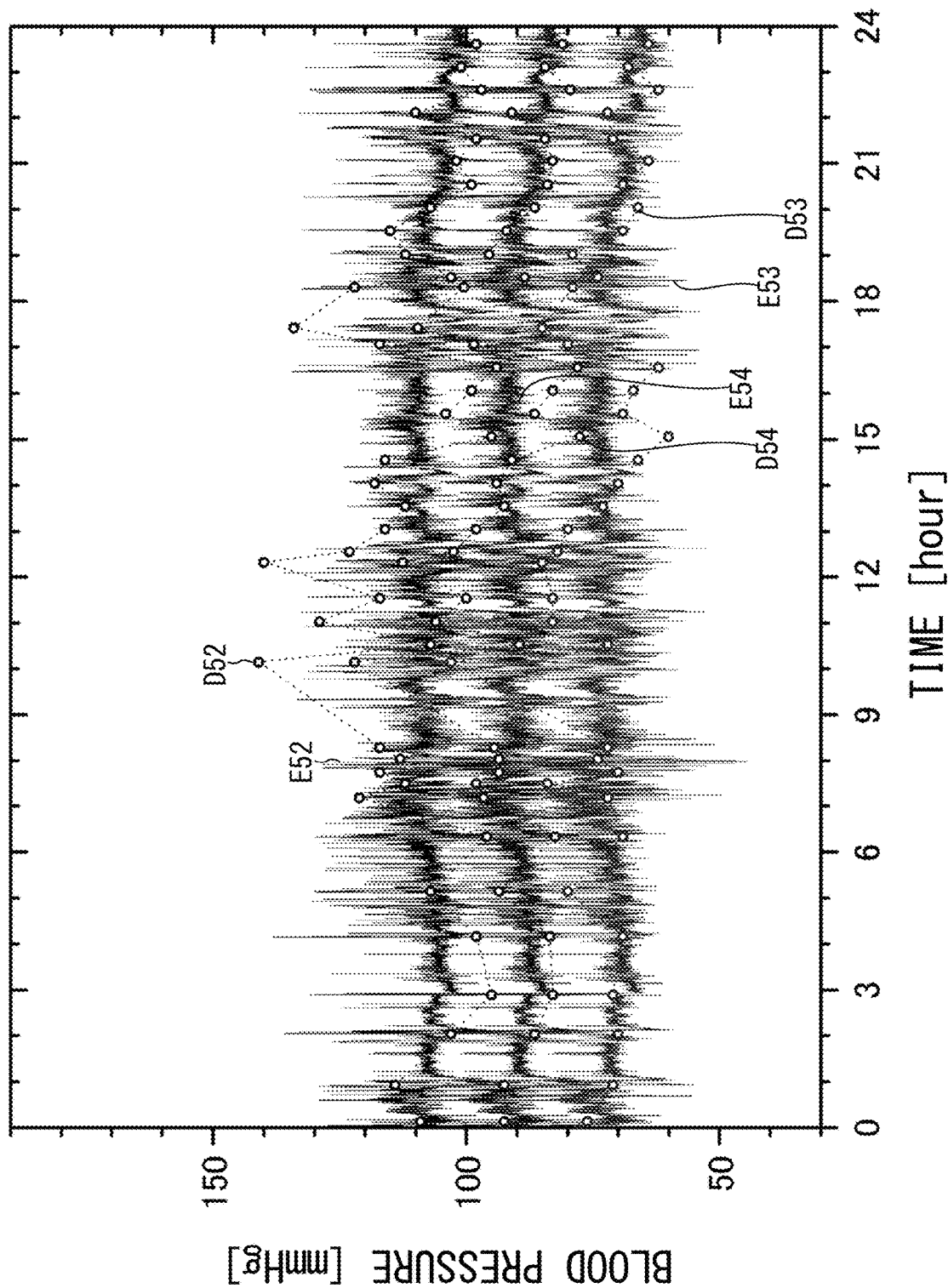
FIG. 30 is a graph illustrating an example of a change of blood pressure estimated by a processing unit of a third modification to the first embodiment with respect to time.
Figure 31:
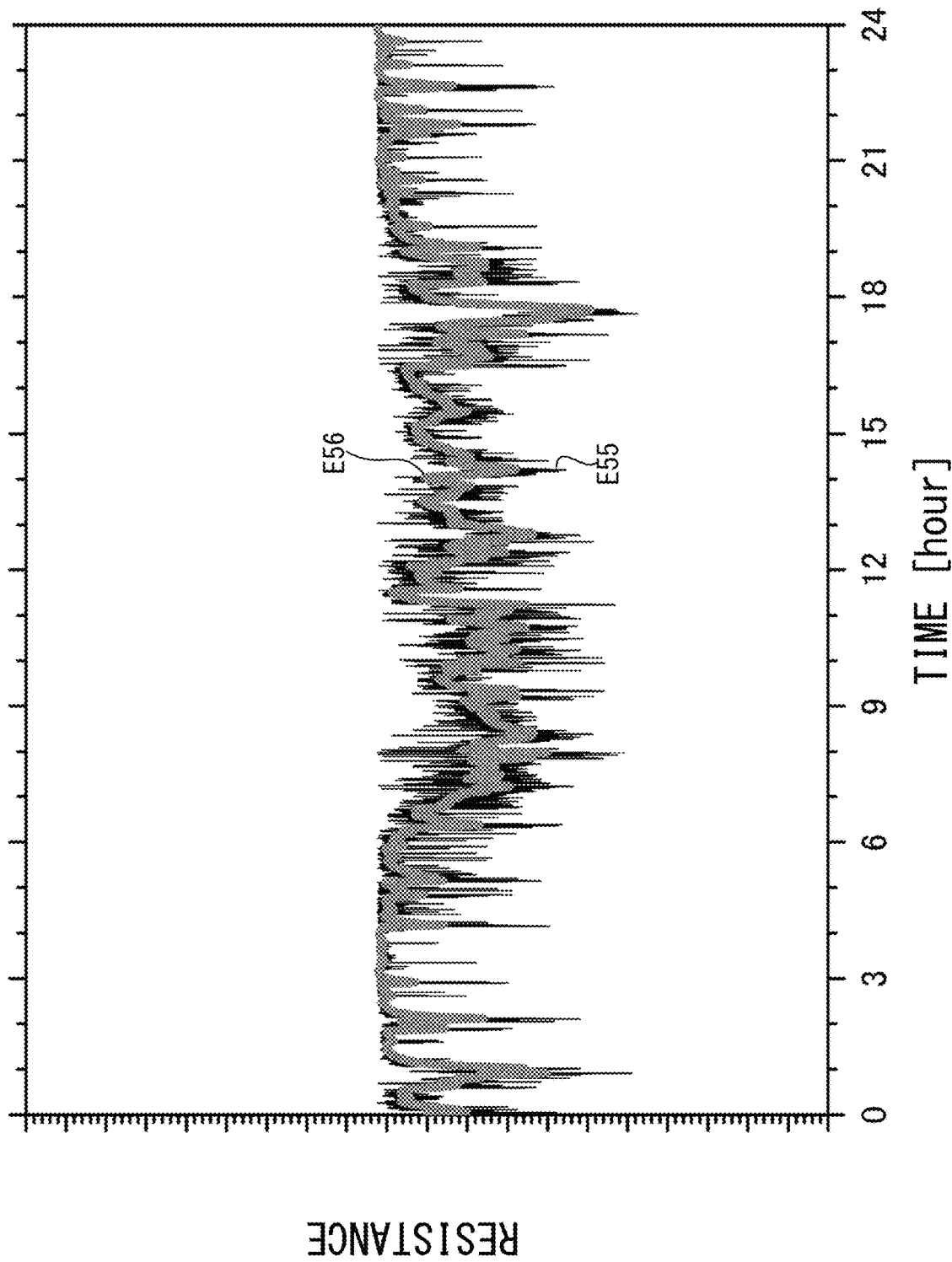
FIG. 31 is a graph illustrating a change of a resistance determined by a processing unit of the third modification to the first embodiment with respect to time.
Figure 32:
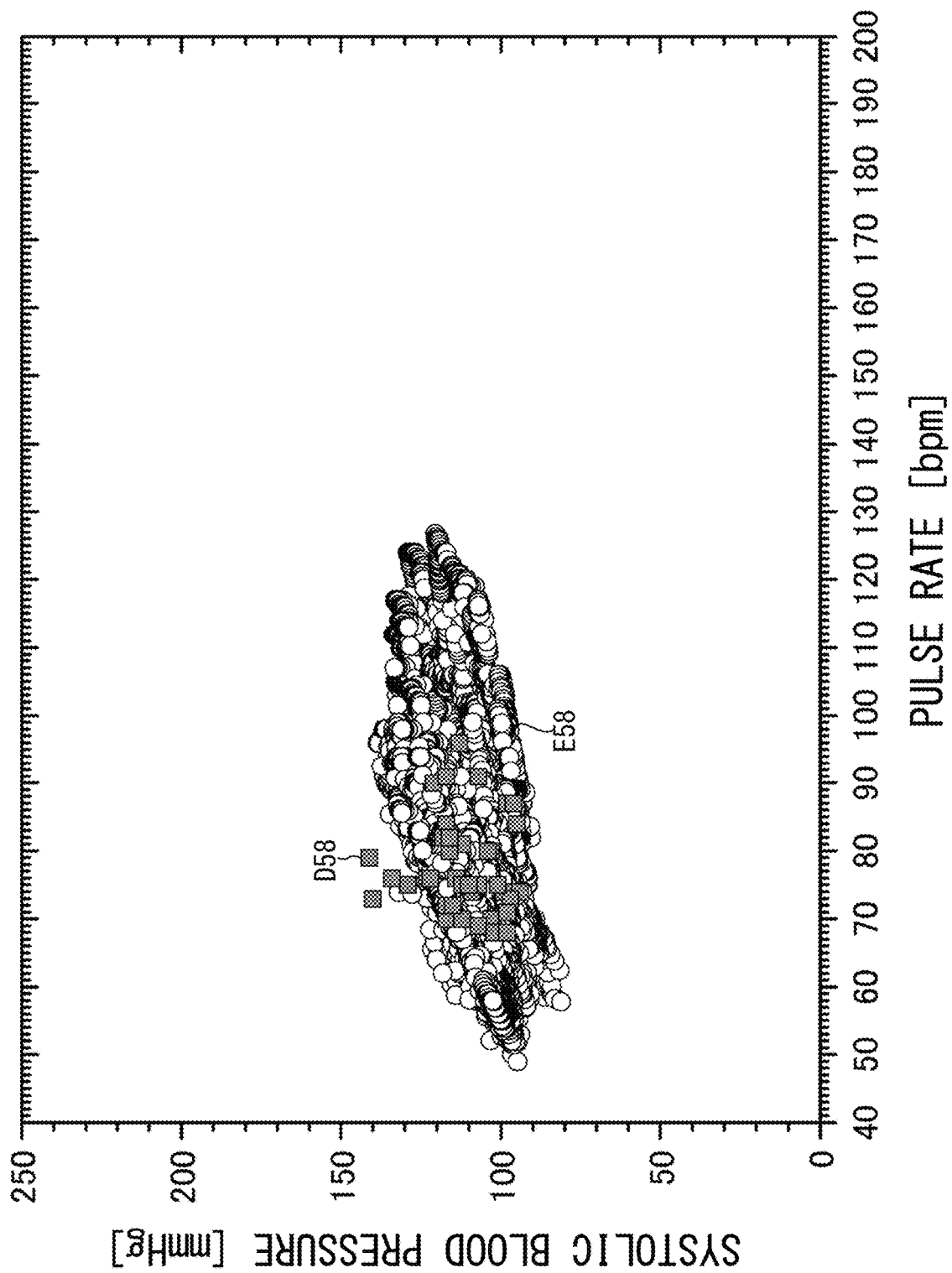
FIG. 32 is a graph illustrating an example of a relationship between the systolic blood pressure estimated by a processing unit of the third modification to the first embodiment and a pulse rate detected by a detecting unit of the third modification to the first embodiment.

FIGS. 30-32 are examples of results of estimation by the blood pressure estimating apparatus 1 in cases where the pulse rate detected by the blood pressure estimating apparatus 1 changes as illustrated in FIG. 11.

The circles D52, D53, and D54 of FIG. 30 express the systolic blood pressure, the diastolic blood pressure, and the average blood pressure measured by a blood pressure measuring apparatus of a comparative example, respectively. In the present modification, the blood pressure measuring apparatus measures a blood pressure using a cuff.

The circles E52, E53, and E54 in FIG. 30 represent the systolic blood pressure, the diastolic blood pressure, and the average blood pressure estimated by the blood pressure estimating apparatus 1, respectively. As exhibited in FIG. 30, the blood pressure estimating apparatus 1 of the third modification to the first embodiment can precisely estimate the blood pressure.

The curves E55 and E56 of FIG. 31 represent the target value $g_4$ of the resistance R4 against the fourth communication pipe FC4, and the resistance R4 against the fourth communication pipe FC4, respectively.

The square D58 in FIG. 32 represents the systolic blood pressure measured by a blood pressure measuring apparatus serving as a comparative example. The circle E58 in FIG. 32 represents the systolic blood pressure estimated by the blood pressure estimating apparatus 1. As exhibited in FIG. 32, the blood pressure estimating apparatus 1 of the third modification to the first embodiment can precisely estimate the relationship between a systolic blood pressure and a pulse rate.

Figure 33:
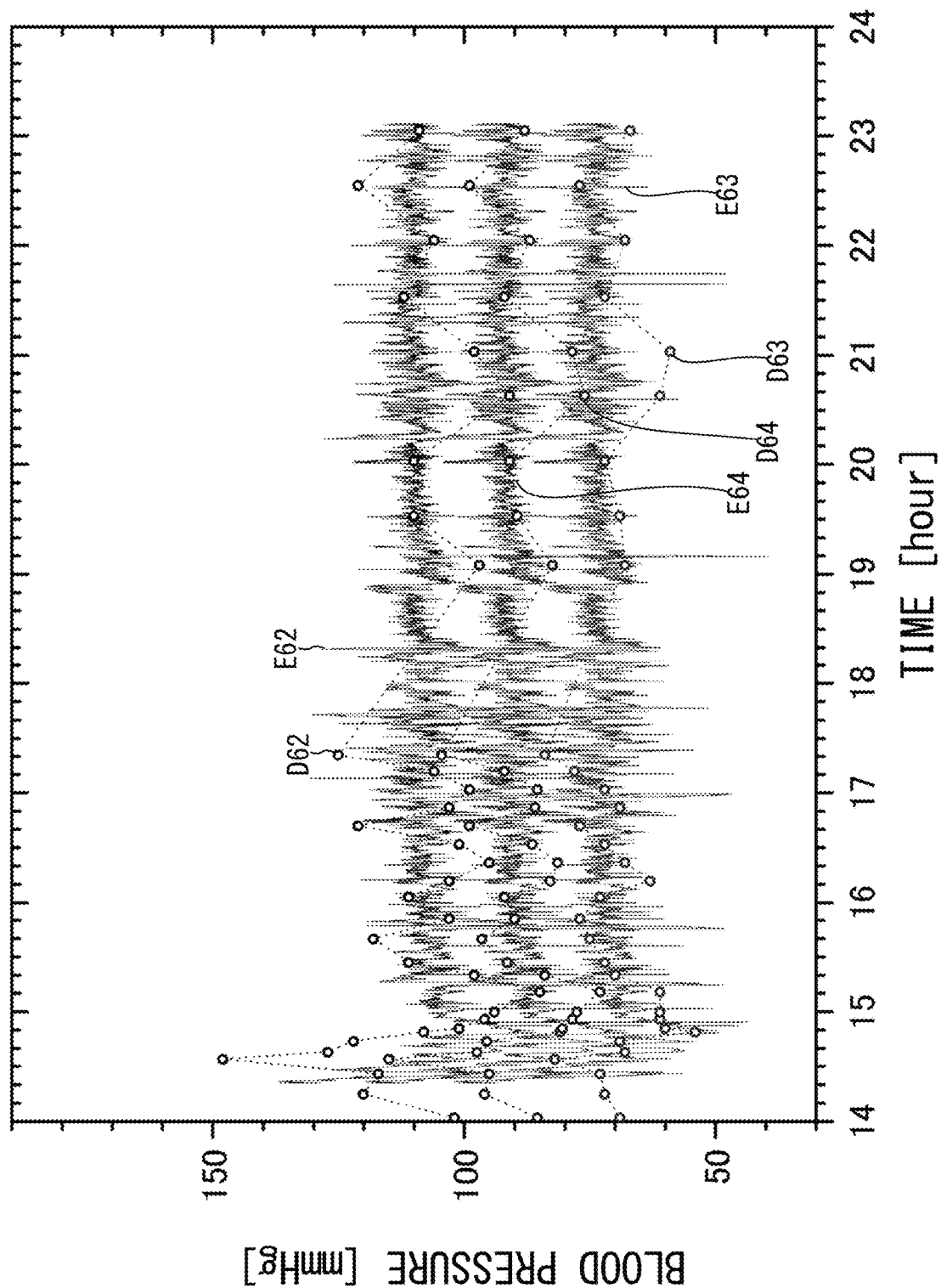
FIG. 33 is a graph illustrating an example of a change of blood pressure estimated by a processing unit of the third modification to the first embodiment with respect to time.
Figure 34:
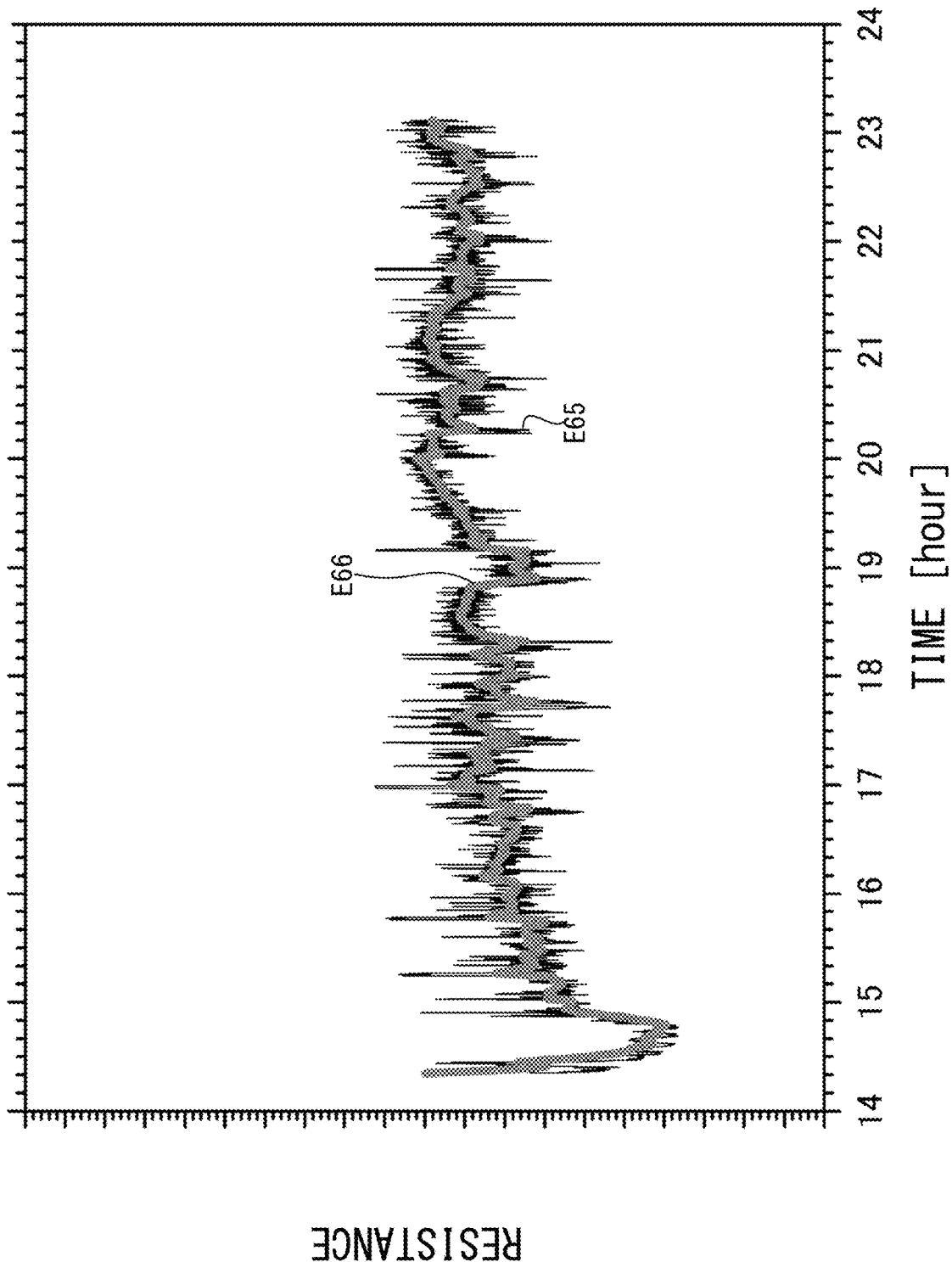
FIG. 34 is a graph illustrating a change of a resistance determined by a processing unit of the third modification to the first embodiment with respect to time.
Figure 35:
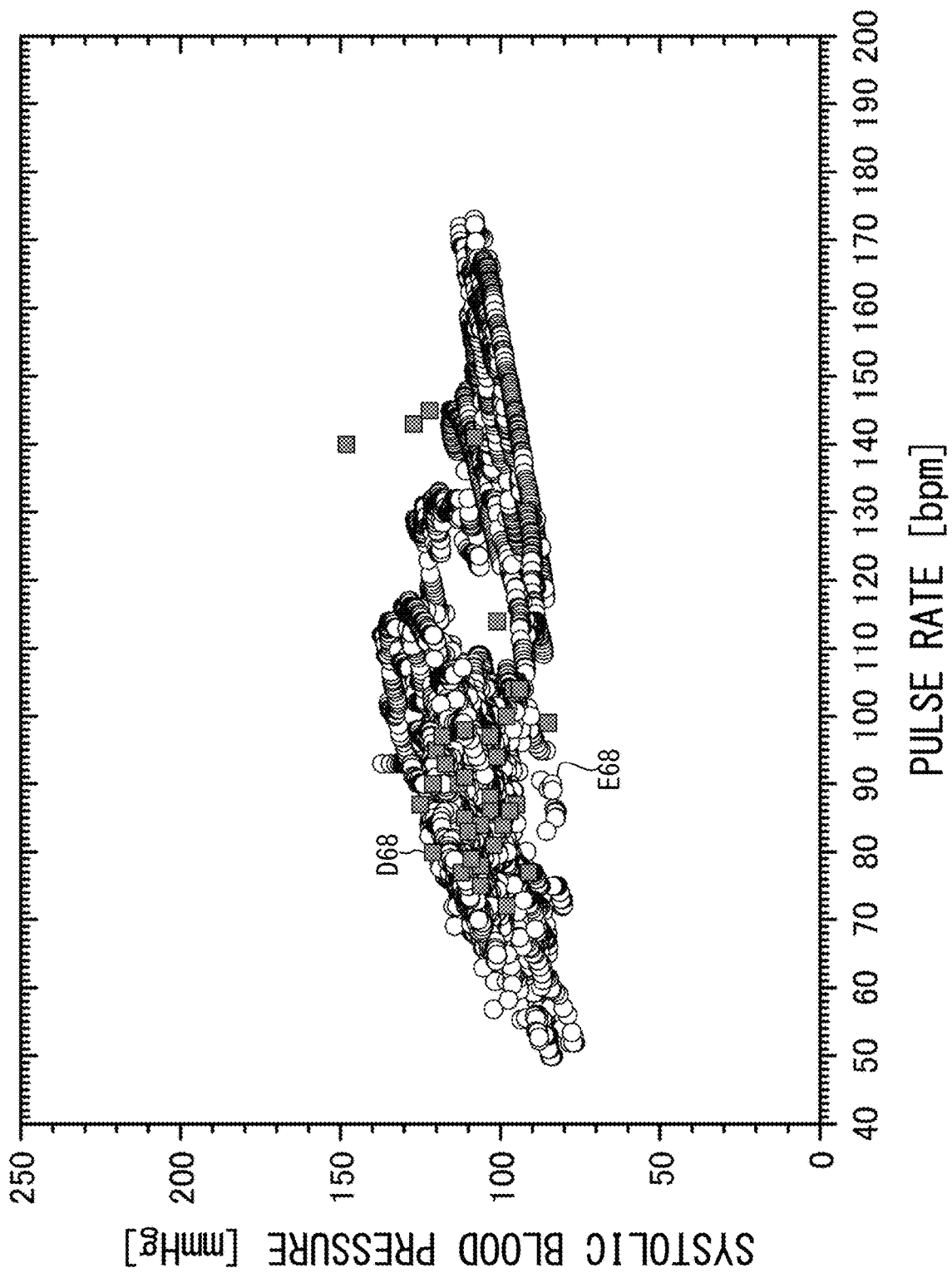
FIG. 35 is a graph illustrating an example of a relationship between the systolic blood pressure estimated by a processing unit of the third modification to the first embodiment and a pulse rate detected by a detecting unit of the third modification to the first embodiment.

FIGS. 33-35 are examples of results of estimation by the blood pressure estimating apparatus 1 in cases where the pulse rate detected by the blood pressure estimating apparatus 1 changes as illustrated in FIG. 15.

The circles D62, D63, and D64 of FIG. 33 express the systolic blood pressure, the diastolic blood pressure, and the average blood pressure measured by a blood pressure measuring apparatus serving as a comparative example, respectively. In the present modification, the blood pressure measuring apparatus measures a blood pressure using a cuff.

The circles E62, E63, and E64 in FIG. 33 represent the systolic blood pressure, the diastolic blood pressure, and the average blood pressure estimated by the blood pressure estimating apparatus 1, respectively. As exhibited in FIG. 33, the blood pressure estimating apparatus 1 of the third modification to the first embodiment can precisely estimate the blood pressure.

The curves E65 and E66 of FIG. 34 represent the target value $g_4$ of the resistance R4 against the fourth communication pipe FC4, and the resistance R4 against the fourth communication pipe FC4, respectively.

The square D68 in FIG. 35 represents the systolic blood pressure measured by a blood pressure measuring apparatus serving as a comparative example. The circle E68 in FIG. 35 represents the systolic blood pressure estimated by the blood pressure estimating apparatus 1. As exhibited in FIG. 35, the blood pressure estimating apparatus 1 of the third modification to the first embodiment can precisely estimate the relationship between a systolic blood pressure and a pulse rate.

Fourth Modification to First Embodiment

Description will now be made in relation to a blood pressure estimating apparatus according to a fourth modification to the first embodiment. The blood pressure estimating apparatus according to the fourth modification to the first embodiment is different from the blood pressure estimating apparatus according of the third modification to the first embodiment in the point of estimating a blood pressure using the resistance not being changed with respect to time. The following description will focus on the difference. Like reference numbers used in the first embodiment designate the same or substantially similar elements also in the fourth modification to the first embodiment.

The processing unit 20 sets the resistances $R_4$ and $R_8$ against the fourth and the eighth communication pipes FC4 and FC8 to the respective initial values $R_{4,\,ini}$ and $R_{8,\,ini}$, and does not change the resistances $R_4$ and $R_8$ with respect to time.

The blood pressure estimating apparatus 1 of the fourth modification to the first embodiment brings the same effects and advantages as those of the blood pressure estimating apparatus 1 of the first embodiment.

Figure 36:
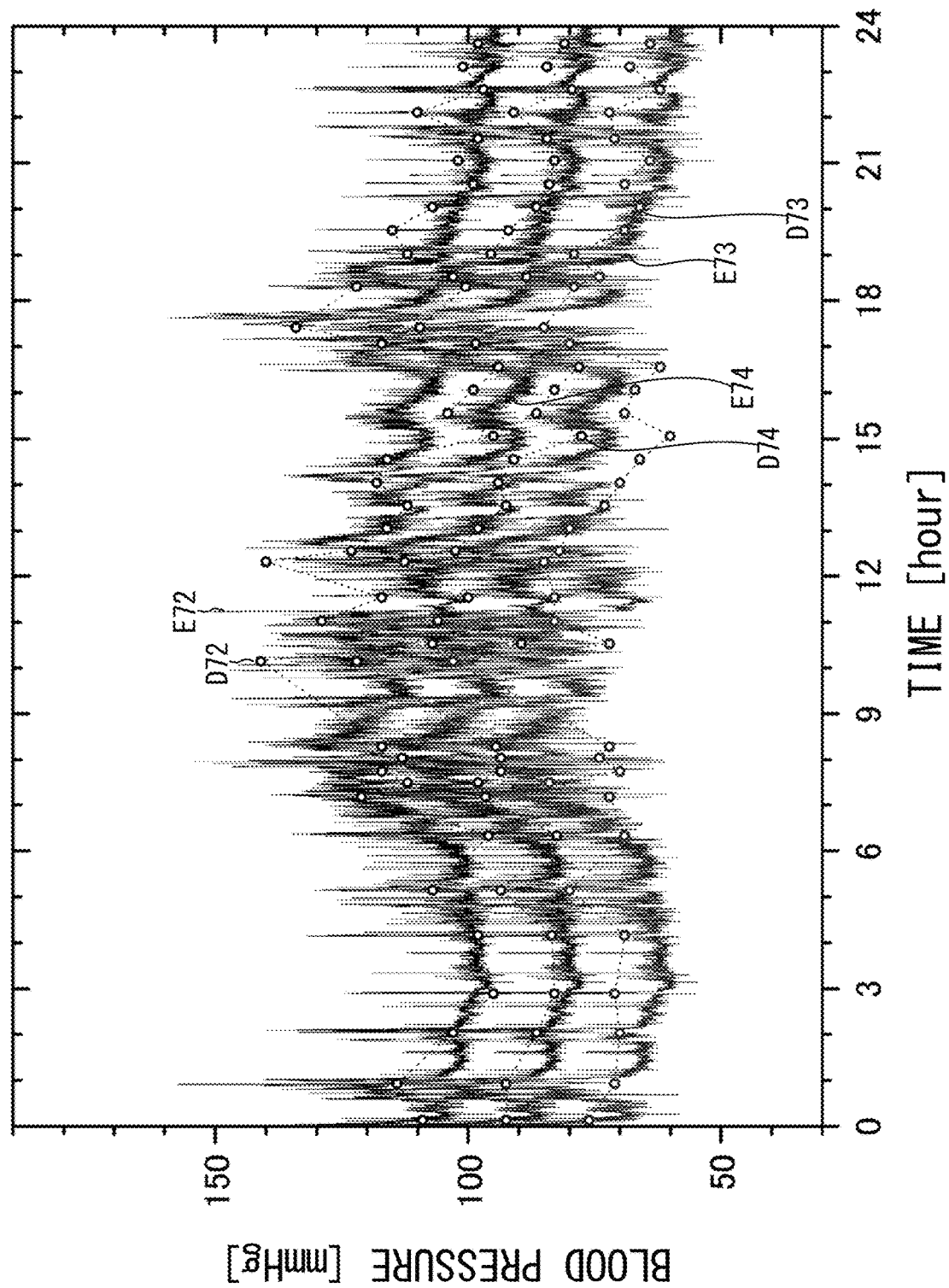
FIG. 36 is a graph illustrating an example of a change of blood pressure estimated by a processing unit of a fourth modification to the first embodiment with respect to time.
Figure 37:
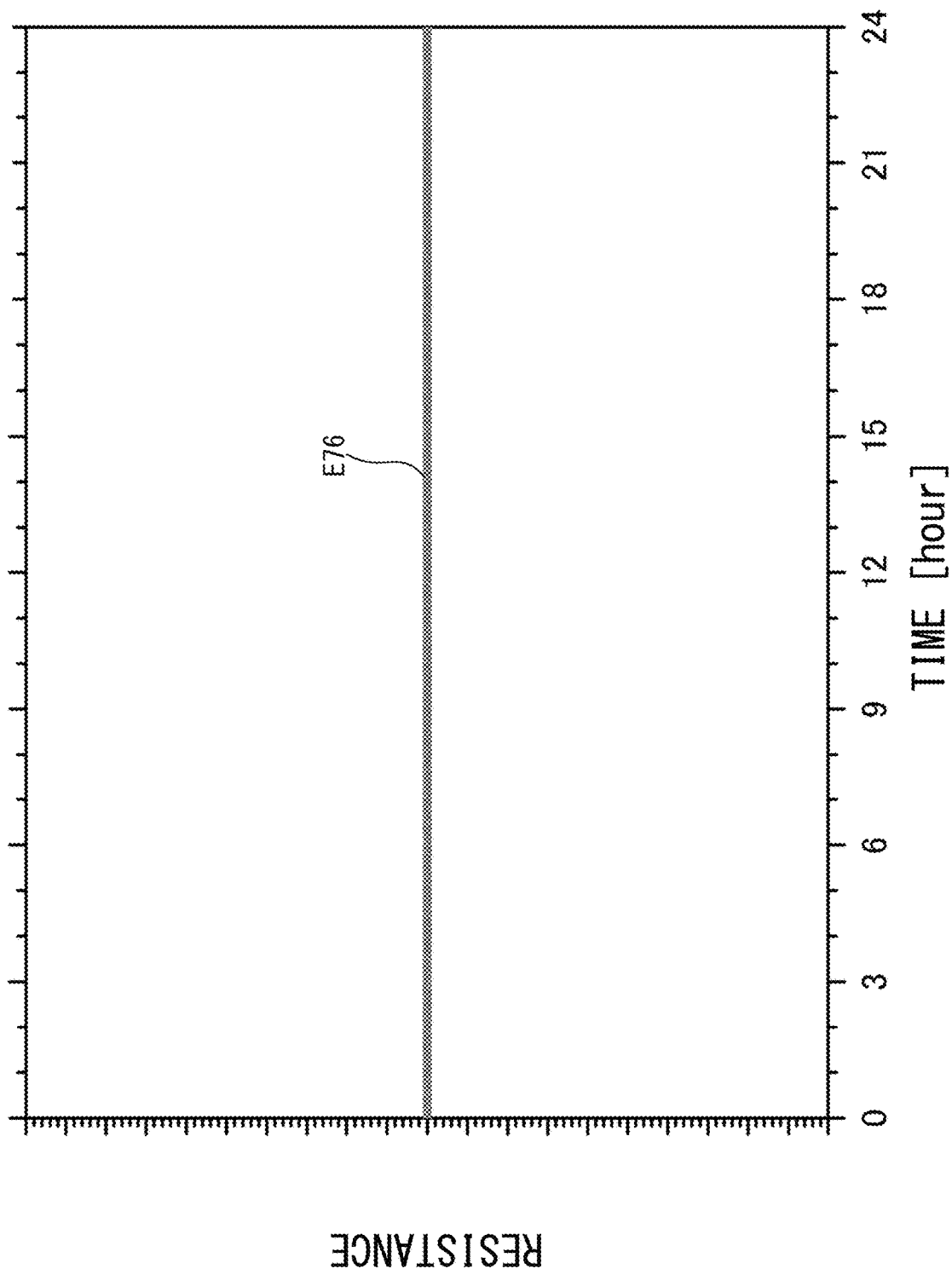
FIG. 37 is a graph illustrating a change of a resistance determined by a processing unit of the fourth modification to the first embodiment with respect to time.
Figure 38:
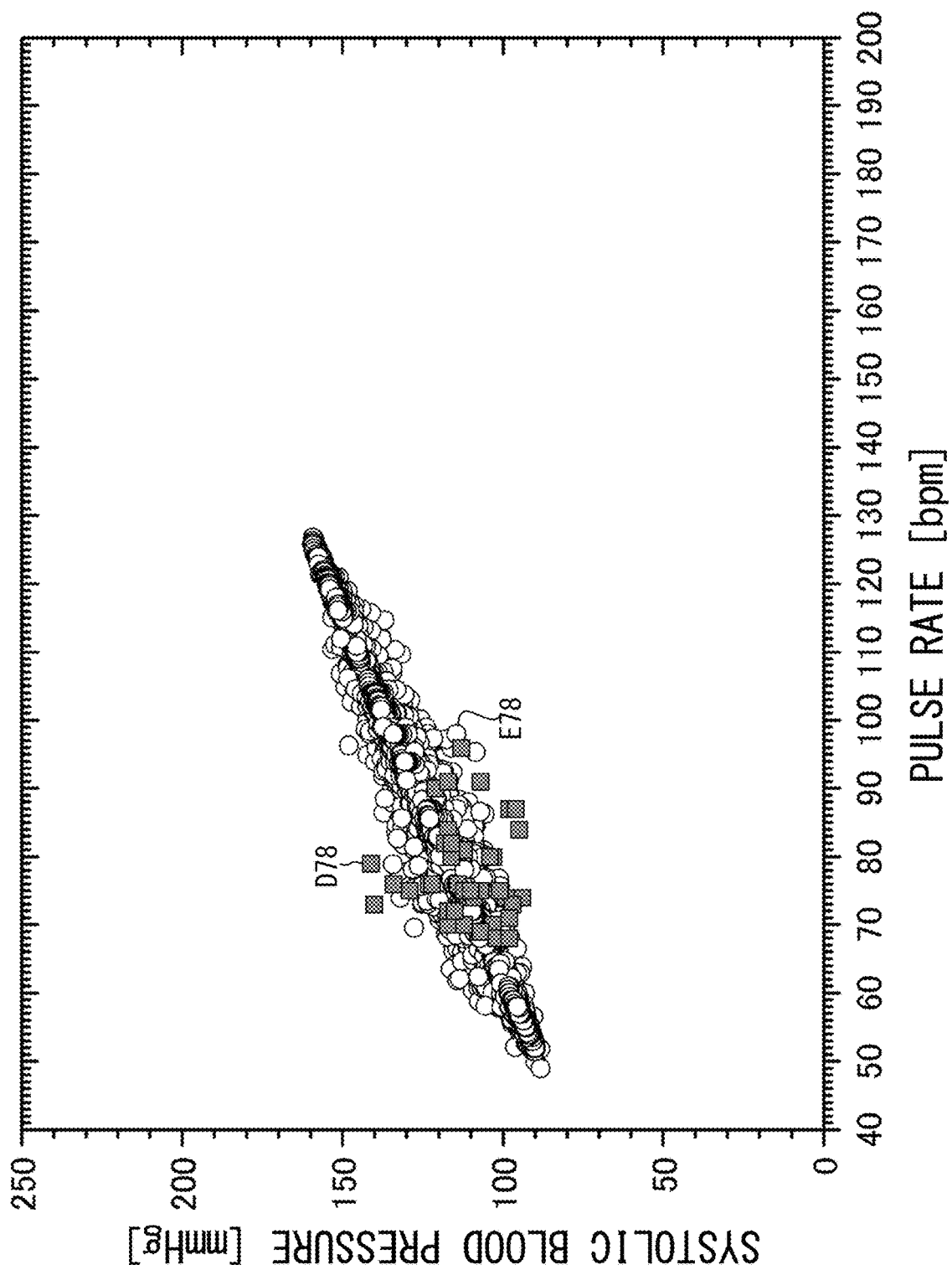
FIG. 38 is a graph illustrating an example of a relationship between the systolic blood pressure estimated by a processing unit of the fourth modification to the first embodiment and a pulse rate detected by a detecting unit of the fourth modification to the first embodiment.

FIGS. 36-38 is examples of a result of estimation by the blood pressure estimating apparatus 1 in cases where the pulse rate detected by the blood pressure estimating apparatus 1 changes as illustrated in FIG. 11.

The circles D72, D73, and D74 of FIG. 36 express the systolic blood pressure, the diastolic blood pressure, and the average blood pressure measured by a blood pressure measuring apparatus serving as a comparative example, respectively. In the present modification, the blood pressure measuring apparatus measures a blood pressure using a cuff.

The circles E72, E73, and E74 in FIG. 36 represent the systolic blood pressure, the diastolic blood pressure, and the average blood pressure estimated by the blood pressure estimating apparatus 1, respectively. As exhibited in FIG. 36, the blood pressure estimating apparatus 1 of the fourth modification to the first embodiment can precisely estimate the blood pressure.

The curve E76 in FIG. 37 represents the resistance R4 against the fourth communication pipe FC4.

The square D78 in FIG. 38 represents the systolic blood pressure measured by a blood pressure measuring apparatus serving as a comparative example. The circle E78 in FIG. 38 represents the systolic blood pressure measured by the blood pressure estimating apparatus 1. As indicated in FIG. 38, the blood pressure estimating apparatus 1 of the fourth modification to the first embodiment can precisely estimate the relationship between a systolic blood pressure and a pulse rate.

Figure 39:
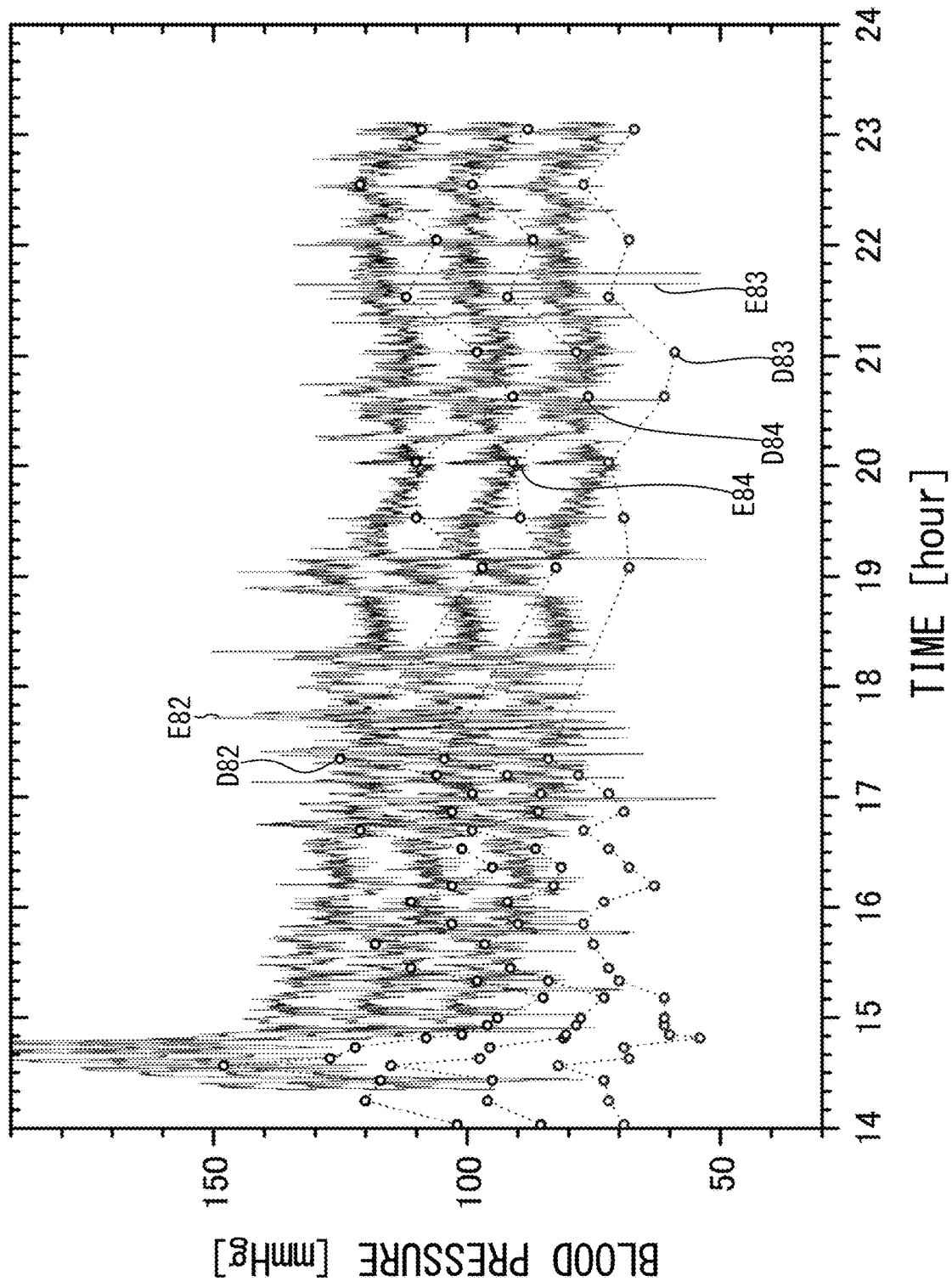
FIG. 39 is a graph illustrating an example of a change of blood pressure estimated by a processing unit of the fourth modification to the first embodiment with respect to time.
Figure 40:
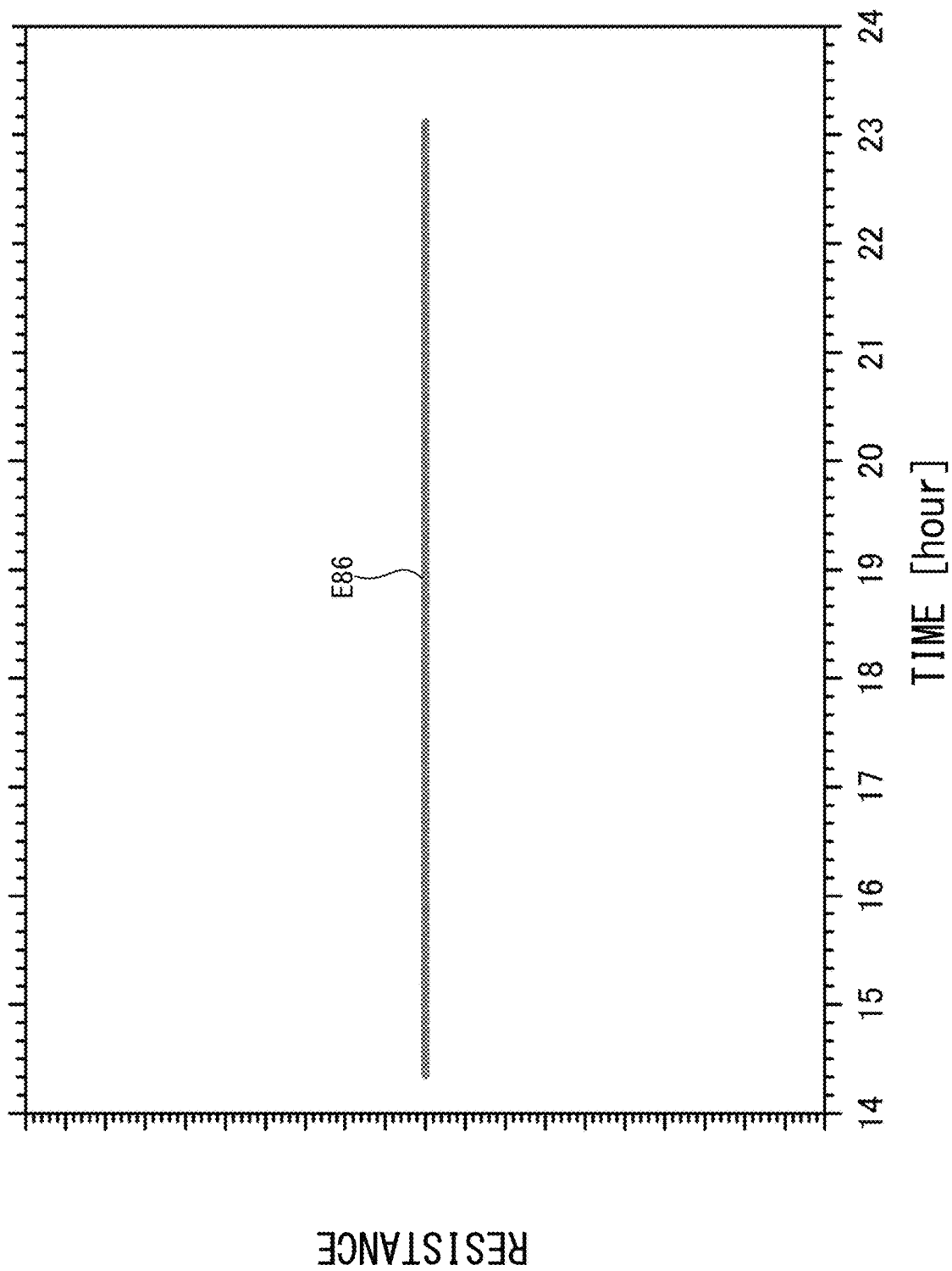
FIG. 40 is a graph illustrating a change of a resistance determined by a processing unit of the fourth modification to the first embodiment with respect to time.
Figure 41:
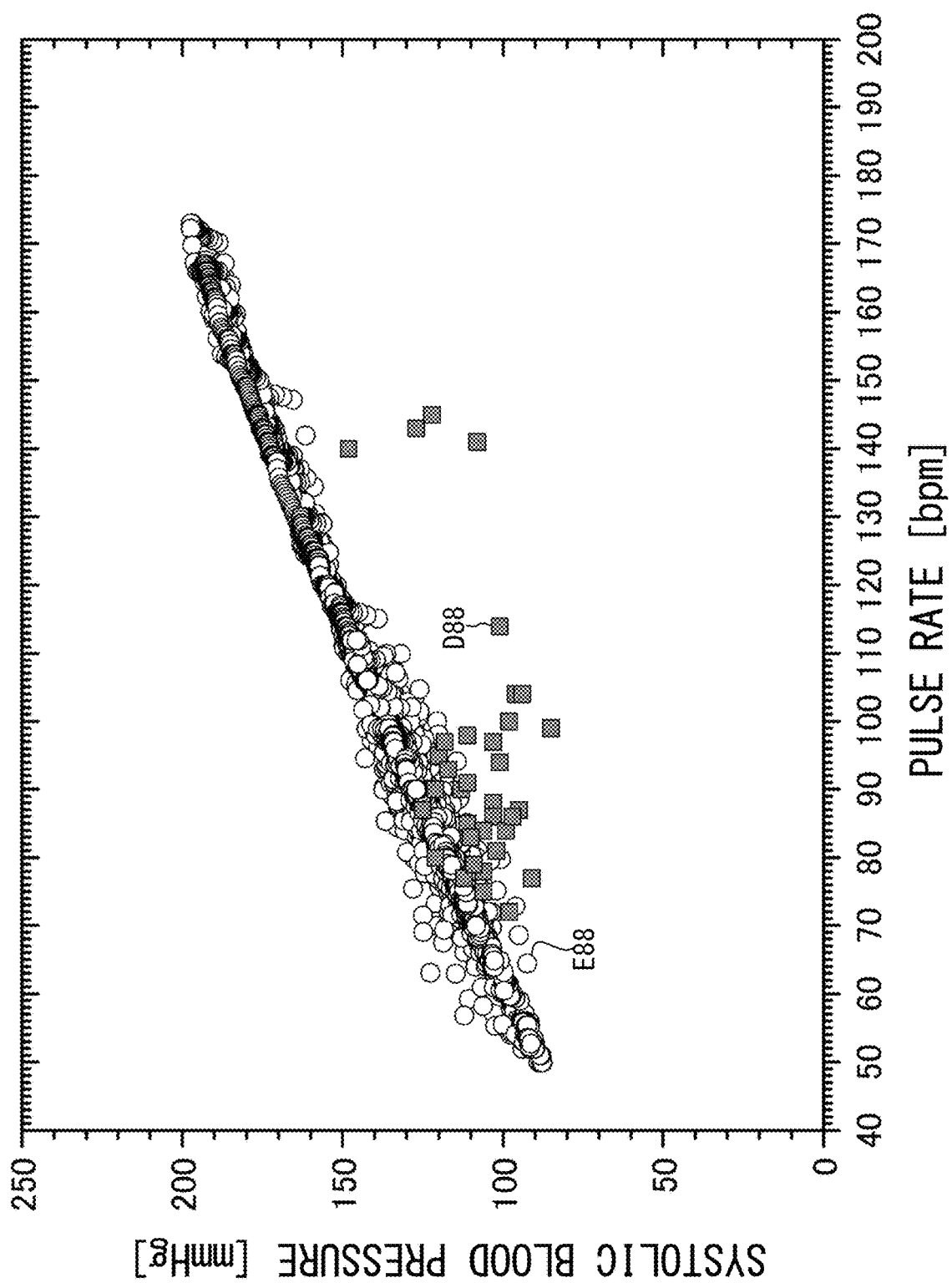
FIG. 41 is a graph illustrating an example of a relationship between the systolic blood pressure estimated by a processing unit of the fourth modification to the first embodiment and a pulse rate detected by a detecting unit of the fourth modification to the first embodiment.

FIGS. 39-41 are examples of results of estimation by the blood pressure estimating apparatus 1 in cases where the pulse rate detected by the blood pressure estimating apparatus 1 changes as illustrated in FIG. 15.

The circles D82, D83, and D84 of FIG. 39 express the systolic blood pressure, the diastolic blood pressure, and the average blood pressure measured by a blood pressure measuring apparatus serving as a comparative example, respectively. In the present modification, the blood pressure measuring apparatus measures a blood pressure using a cuff.

The circles E82, E83, and E84 in FIG. 39 represent the systolic blood pressure, the diastolic blood pressure, and the average blood pressure, respectively. As exhibited in FIG. 39, the blood pressure estimating apparatus 1 of the fourth modification to the first embodiment can precisely estimate the blood pressure.

The curve E86 in FIG. 40 represents the resistance R4 against the fourth communication pipe FC4.

The square D88 in FIG. 41 represents the systolic blood pressure measured by a blood pressure measuring apparatus serving as a comparative example. The circle E88 in FIG. 41 represents the systolic blood pressure estimated by the blood pressure estimating apparatus 1. As exhibited in FIG. 41, the blood pressure estimating apparatus 1 of the fourth modification to the first embodiment can precisely estimate the relationship between a systolic blood pressure and a pulse rate.

According to the above-described technologies, it is possible to precisely estimate blood pressure.

All examples and conditional language provided herein are intended for pedagogical purposes to aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiment(s) of the present invention have been described in detail, it should be understood that the various changes, substitutions, and alterations could be made hereto without departing from the spirit and scope of the invention.

What is claimed is:

1. A blood pressure estimating apparatus comprising:
a detector configured to detect a pulse rate from a heartbeat of a living body;
processor circuitry configured to estimate pressure of each of a plurality of vessels containing fluid therein and being resiliently deformable based on an expression derived from a mathematical model, the mathematical model expressing a circulatory system of the living body by the plurality of vessels, communication pipes annularly connecting the plurality of vessels, and a valve preventing backflow of the fluid, changing a no-load volume of each of a subset of vessels of the plurality of vessels with respect to time, not changing a no-load volume of each of the remaining vessels within the plurality of vessels with respect to time, changing a resistance of each of a subset of communication pipes of the communication pipes with respect to time, and not changing a resistance of each of the remaining communication pipes within the communication pipes with respect to time, wherein
the processor circuitry comprising:
a memory configured to store information related to a reference no-load volume for each of the vessels, wherein a subset of the reference no-load volumes can be determined from the pulse rate and a time from a time point when a pulse starts in a period of the heartbeat, and information related to a reference target resistance for each of the communication pipes, wherein a subset of the reference target resistances values can be determined from the pulse rate;
an estimator configured to set initial values of a time, pressure of each of the plurality of vessels, and a resistance of each of the communication pipes, configured to obtain a pulse rate at the set time based on the pulse rate detected by the detector, configured to calculate a target resistance based on the reference target resistance and the obtained pulse rate at the set time, and configured to calculate a period length and an intra-period time at the set time based on the obtained pulse rate at the set time;
a determiner configured to calculate, based on the reference no-load volumes, the expression, and the pulse rate at the set time obtained by the estimator, a change of the no-load volume of each of the subset of the plurality of vessels, wherein the reference no-load volumes are determined based on the pulse rate and an estimated pulse amplitude, the estimated pulse amplitude being calculated by setting an initial value of the estimated pulse amplitude in a differential equation including the pulse rate, target amplitude, and a time constant of the estimated pulse amplitude; and
the processer circuitry calculates the pressure of each of the plurality of vessels after a step time from the expression and the change of the no-load volumes calculated by the determiner.

2. The blood pressure estimating apparatus according to claim 1, wherein the reference target resistance is determined from a resistance of the communication pipes while the living body is resting, the pulse rate at the set time, and a reference value of the pulse rate.

3. The blood pressure estimating apparatus according to claim 1, wherein
the detector further detects a detected pulse amplitude;
the reference no-load is determined from the pulse rate, the time from when the pulse starts in a period of the heartbeat, and the detected pulse amplitude, and the reference target resistance is determined from the pulse rate and the detected pulse amplitude; and
the target resistance of the estimator is calculated from the reference target resistance, and the obtained pulse rate and a pulse amplitude at the set time obtained by setting the initial values of the time, the pressure of each of the plurality of vessels, and the resistance of each of the communication pipes, and obtaining the pulse rate and the pulse amplitude at the time based on the detected pulse rate and the detected pulse amplitude.

4. The blood pressure estimating apparatus according to claim 3, wherein the reference target resistance is determined, based on the pulse amplitude and a reference value of the pulse amplitude.

5. The blood pressure estimating apparatus according to claim 3, wherein the detected pulse amplitude is detected by the detector, and the detected pulse amplitude detected by the detector is used to determine the reference no-load instead of the estimated pulse amplitude.

6. The blood pressure estimating apparatus according to claim 1, wherein the plurality of vessels are vessels that are one of resiliently deformed vessels like each of a left atrium, a left ventricle, an aorta and an artery on a downstream side of the aorta, a vena cava and a vein on an upstream side of the vena cava, a right atrium, a right ventricle, a pulmonary artery, and a pulmonary vein.

7. The blood pressure estimating apparatus according to claim 6, wherein:
the part of the plurality of vessels each having a no-load volume changing with respect to time correspond to the left ventricle and the right ventricle;
the part of the communication pipes having a resistance changing with respect to time in accordance with the pulse rate is a communication pipe that connects the artery and the vein and a communication pipe that connects the pulmonary artery and the pulmonary vein.

8. The blood pressure estimating apparatus according to claim 1,
wherein the pressure of each of a plurality of vessels is estimated based on the pulse rate and a pulse amplitude that is directly or indirectly obtained from the heartbeat of the living body as well as the expression derived from the mathematical model;
wherein the pulse amplitude that is directly obtained from the heartbeat is detected by the detector; and
wherein the pulse amplitude that is indirectly obtained from the heartbeat is calculated, by the processor circuitry, based on the pulse rate.

9. A method for estimating blood pressure comprising:
detecting pulse rate from a heartbeat of a living body;
setting an expression derived from a mathematical model, the mathematical model expressing a circulatory system of the living body by a plurality of vessels containing fluid therein and being resiliently deformable, communication pipes annularly connecting the plurality of vessels, and a valve preventing backflow of the fluid, changing a no-load volume of each of a subset of vessels of the plurality of vessels with respect to time, not changing a no-load volume of each of the remaining vessels within the plurality of vessels with respect to time, changing a resistance of each of a subset of communication pipes of the communication pipes with respect to time, and not changing a resistance of each of the remaining communication pipes within the communication pipes with respect to time;
setting information related to a reference no-load volume for each of the vessels, wherein a subset of the reference no-load volumes can be determined from the pulse rate and a time from a time point when a pulse starts in a period of the heartbeat, and information related to a reference target resistance for each of the communication pipes, wherein a subset of the reference target resistances values can be determined from the pulse rate;
setting initial values of a time, pressure of each of the plurality of vessels, and a resistance of each of the communication pipes;
obtaining a pulse rate at the set time based on the detected pulse rate;
calculating a target resistance based on the reference target resistance and the obtained pulse rate at the set time, and calculating a period length and an intra-period time at the set time based on the obtained pulse rate at the set time; and
calculating, based on the set reference no-load volumes, the expression, and the obtained pulse rate at the set time, a change of the no-load volume of each of the subset of the plurality of vessels, wherein the reference no-load volumes are determined based on the pulse rate and an estimated pulse amplitude, the estimated pulse amplitude being calculated by setting an initial value of the estimated pulse amplitude in a differential equation including the pulse rate, target amplitude, and a time constant of the estimated pulse amplitude to be estimated; and
calculating the pressure of each of the plurality of vessels after a step time from the expression and the calculated change of the no-load volumes.

10. A non-transitory computer-readable recording medium having stored therein a program for estimating blood pressure, the program causing a computer to execute a process comprising:
setting an expression derived from a mathematical model, the mathematical model expressing a circulatory system of the living body by a plurality of vessels containing fluid therein and being resiliently deformable, communication pipes annularly connecting the plurality of vessels, and a valve preventing backflow of the fluid, changing a no-load volume of each of a subset of vessels of the plurality of vessels with respect to time, not changing a no-load volume of each of the remaining vessels within the plurality of vessels with respect to time, changing a resistance of each of a subset of communication pipes of the communication pipes with respect to time, and not changing a resistance of each of the remaining communication pipes within the communication pipes with respect to time;
setting information related to a reference no-load volume for each of the vessels, wherein a subset of the reference no-load volumes can be determined from the pulse rate and a time from a time point when a single pulse starts in a period of the heartbeat, and information related to a reference target resistance for each of the communication pipes, wherein a subset of the reference target resistances values can be determined from the pulse rate;
setting initial values of a time, pressure of each of the plurality of vessels, and a resistance of each of the communication pipes;
obtaining a pulse rate at the set time based on a detected pulse rate;
calculating a target resistance based on the reference target resistance and the obtained pulse rate at the set time, and calculating a period length and an intra-period time at the set time based on the obtained pulse rate at the set time; and
calculating, based on the set reference no-load volumes, the expression, and the obtained pulse rate at the set time, a change of the no-load volume of each of the subset of the plurality of vessels, wherein the reference no-load volumes are determined based on the pulse rate and an estimated pulse amplitude, the estimated pulse amplitude being calculated by setting an initial value of the estimated pulse amplitude in a differential equation including the pulse rate, target amplitude, and a time constant of the estimated pulse amplitude; and
calculating the pressure of each of the plurality of vessels after a step time from the expression and the change of the calculated no-load volumes.

* * * * *